US012576191B2

(12) United States Patent
Tzahor et al.

(10) Patent No.: US 12,576,191 B2
(45) **Date of Patent: *Mar. 17, 2026**

(54) METHOD OF INDUCING CARDIOMYOCYTES PROLIFERATION AND TREATING HEART DISEASES

(71) Applicant: Yeda Research and Development Co. Ltd., Rehovot (IL)

(72) Inventors: Eldad Tzahor, Rehovot (IL); Elad Bassat, Rehovot (IL)

(73) Assignee: YEDA RESEARCH AND DEVELOPMENT CO. LTD., Rehovot (IL)

( * ) Notice: Subject to any disclaimer, the term of this patent is extended or adjusted under 35 U.S.C. 154(b) by 0 days.

This patent is subject to a terminal disclaimer.

(21) Appl. No.: 18/368,332

(22) Filed: Sep. 14, 2023

(65) Prior Publication Data

US 2024/0042104 A1 Feb. 8, 2024

Related U.S. Application Data

(63) Continuation of application No. 16/746,878, filed on Jan. 19, 2020, now Pat. No. 11,786,640, which is a continuation of application No. 15/772,065, filed as application No. PCT/IL2016/051165 on Oct. 27, 2016, now Pat. No. 10,589,132.

(30) Foreign Application Priority Data

Oct. 29, 2015 (IL) .......................................... 242380

(51) Int. Cl.
| | |
|---|---|
| *A61K 38/17* | (2006.01) |
| *A61L 27/54* | (2006.01) |
| *A61P 9/10* | (2006.01) |
| *C07K 14/47* | (2006.01) |
| *C12N 5/077* | (2010.01) |

(52) U.S. Cl.
CPC .......... *A61L 27/54* (2013.01); *A61K 38/1709* (2013.01); *A61P 9/10* (2018.01); *C07K 14/4725* (2013.01); *C12N 5/0657* (2013.01); *A61L 2300/252* (2013.01); *C12N 2501/998* (2013.01)

(58) Field of Classification Search
None
See application file for complete search history.

(56) References Cited

U.S. PATENT DOCUMENTS

| | | | |
|---|---|---|---|
| 5,814,478 | A | 9/1998 | Valenzuela et al. |
| 6,413,740 | B1 | 7/2002 | Valenzuela et al. |
| 6,852,838 | B2 | 2/2005 | Valenzuela et al. |
| 8,685,915 | B2 | 4/2014 | Hettwer et al. |
| 10,589,132 | B2 | 3/2020 | Tzahor et al. |
| 2006/0216279 | A1 | 9/2006 | Glass et al. |
| 2007/0014773 | A1 | 1/2007 | Matheny |
| 2007/0014869 | A1 | 1/2007 | Matheny |
| 2007/0014871 | A1 | 1/2007 | Matheny |
| 2010/0095387 | A1 | 4/2010 | Smith et al. |
| 2018/0318612 | A1 | 11/2018 | Tzahor et al. |
| 2020/0139162 | A1 | 5/2020 | Tzahor et al. |
| 2020/0306343 | A1 | 10/2020 | Tzahor et al. |

FOREIGN PATENT DOCUMENTS

| | | |
|---|---|---|
| EP | 2 295 068 A1 | 3/2011 |
| WO | WO-97/21811 A2 | 6/1997 |
| WO | WO-2007/011682 A2 | 1/2007 |
| WO | WO-2008/021896 A2 | 2/2008 |
| WO | WO-2017/072772 A1 | 5/2017 |
| WO | WO-2019/106680 A1 | 6/2019 |

OTHER PUBLICATIONS

Babbitt et al. "Intracoronary adenosine administered after reperfusion limits vascular injury after prolonged ischemia in the canine model", Circulation, 80,5 (1989):1388-1399, 1989.

Bassat et al. "The Extracellular Matrix Protein Agrin Promotes Heart Regenerationin Mice", Nature, XP055565028, 547(7662): 179-184, Jul. 13, 2017.

Cahill et al. "Heart Failure After Myocardial fufarction in the Era of PrimaryPercutaneous Coronary Intervention: Mechanism, Incidence and Identification of Patients at Risk", World Journal of Cardiology, 9(5): 407-415, May 26, 2017.

Campanelli et al. "Alternative RNA Splicing That Determines Agrin Activity Regulates Binding to Heparin and Alpha-Dystroglycan", Development, XP0'.55336413, 122: 1663-1672, May 1, 1996. Abstract, p. 1663, 1-h col., Para 1—p. 1671, r-h col., Para 4.

Communication Pursuant to Article 94(3) EPC Dated Feb. 9, 2021 From the European Patent Office Re. Application No. 16794758.9. (4 Pages).

Communication Pursuant to Article 94(3) EPC Dated Feb. 26, 2020 From the European Patent Office Re. Application No. 16794758.9. (6 Pages).

Eroglu et al. "Heart Regeneration 4.9: Matrix Medicine", Developmental Cell, XP085124219, 42(1): 7-8, Jul. 10, 2017.

Final Office Action Dated Jul. 27, 2021 from the US Patent and Trademark Office Re. U.S. Appl. No. 16/891,165 (26 pages).

Gesemann et al. "Alternative Splicing of angrin alters Its Binding to Heparin, Dystroglycan, and the Putative Agrin Receptor", Neuron, 16(4): 755-767, Apr. 1996. Fig.I.

Glass et al. "Agrin Acts via a MuSK Receptor Complex", Cell, 85(4): 513-523, May 17, 1996.

Herzog et al. "Short-term low dose intracoronary diltiazen administered at the onset of reperfusion reduces myocardial infarct size", International journal of cardiology, 59 (1997): 21-27, 1997.

Hiigenberg et al. "Agrin Regulation of a3 Sodium-Potassium ATPase Activity Modulates Cardiac Myocyte Contraction", Journal of Biological Chemistry, 284(25): 16956-16965, Jun. 19, 2009.

Hinkel et al. "Inhibition of Micro RN A-92a Protects Against Ischemia/Reperfusion Injury in a Large-Animal Model", Circulation, 128(10): 1066-1075, Published Online Jul. 29, 2013.

(Continued)

*Primary Examiner* — Daniel C Gamett
(74) *Attorney, Agent, or Firm* — Foley & Lardner LLP

(57) ABSTRACT

An Agrin peptide which induces proliferation of cardiomyocytes for treating a heart disease is provided.

19 Claims, 21 Drawing Sheets

Figures 1N, 1O, 1P:
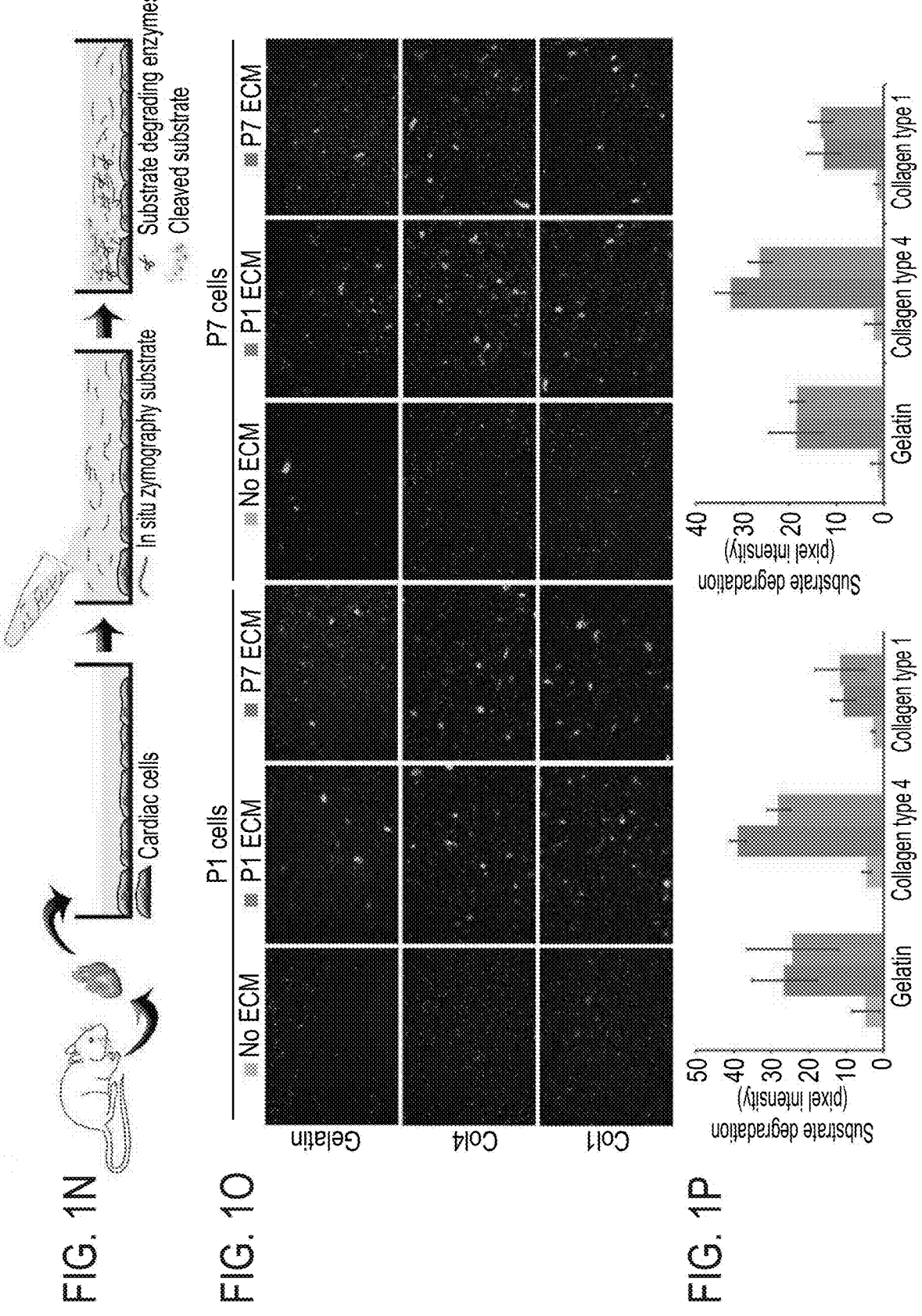

Specification includes a Sequence Listing.

(56) References Cited

OTHER PUBLICATIONS

Hohenester et al. "The Crystal Structure of a Laminin G-Like Module Reveals the Molecular Basis of Alpha-Dystroglycan Binding to Laminins, Perlecan, and Agrin", Molecular Cell, 4(5): 783-792, Nov. 1999.

Hoover et al. "The COOR-Terminal Domain of Agrin Signals via a Synaptic Receptor in Central Nervous System Neurons", The Journal of Cell Biology, XP055336430, 161(5): 923-932, Jun. 9, 2003.

Hopf et al. "Agrin Binding to Alpha-Dystroglycan. Domains of Agrin Necessary to Induce Acetylcholine Receptor Clustering Are Overlapping But Not Identical to the Alpha-Dystroglycan-Binding Region", The Journal of Biological Chemistry, 271(9): 5231-5236, Mar. 1, 1996. Figs.1, 6.

International Preliminary Report on Patentability Dated May 11, 2018 From the International Bureau of WIPO Re. Application No. PCT/IL2016/051165. (9 Pages).

International Preliminary Report on Patentability Dated Jun. 18, 2020 From the International Bureau of WIPO Re. Application No. PCT/IL2018/051323. (8 Pages).

International Search Report and the Written Opinion Dated Feb. 1, 2017 From the International Searching Authority Re. Application No. PCT/IL2016/051165. (15 Pages).

International Search Report and the Written Opinion Dated Mar. 21, 2019 From the International Searching Authority Re. Application No. PCT/IL2018/051323. (16 Pages).

Kondo et al. "Impact of a Single Intracoronary Administration of Adiponectin on Myocardial Ischemia/Reperfusion Injury in a Pig Model", Circulation: Cardiovascular Interventions, 3(2): 166-173, Apr. 2010.

Laskey "Cardiovascular Device Development: Drug-Eluting Stents and Implantable Devices for the Treatment of Heart Failure—The View From the Circulatory System Advisory Panel", American Journal of Therapeutics, 12(2): 179-182, Mar.-Apr. 2005.

Margeta et al. "Cardiac Pathology Exceeds Skeletal Muscle Pathology in Two Cases of Limb-Girdle Muscular Dystrophy Type 21", Muscle Nerve, 40(5): 883-889, Published Online Aug. 24, 2009.

Notice of Allowance Dated Nov. 20, 2019 From the US Patent and Trademark Office Re. U.S. Appl. No. 15/772,065. (15 pages).

Notification of Office Action and Search Report Dated Mar. 1, 2021 From the State Intellectual Property Office of the People's Republic of China Re. Application No. 201680077347.3 and Its Pending Claims in English. (11 Pages).

Notification of Office Action and Search Report Dated Mar. 1, 2021 From the State Intellectual Property Office of the People's Republic of China Re. Application No. 201680077347.7 (9 Pages).

Official Action Dated Mar. 9, 2021 From the US Patent and Trademark Office Re. U.S. Appl. No. 16/891,165. (20 Pages).

Official Action Dated Nov. 19, 2021 from US Patent and Trademark Office Re. U.S. Appl. No. 16/891,165. (9 pages).

Official Action Dated Apr. 29, 2022 from US Patent and Trademark Office Re. U.S. Appl. No. 16/891,165. (10 pages).

Official Action Dated Oct. 29, 2020 From the US Patent and Trademark Office Re. U.S. Appl. No. 16/891,165. (30 Pages).

Request for Examination and Search Report Dated Feb. 12, 2020 From the Federal Service for Intellectual Property, Federal Government Budgetary Institution, Federal Institute of Industrial Property, FIPS of the Russian Federation Re. Application No. 2018119359 and Its Translation of Request for Examination Into English. (12 Pages).

Sasse et al. "Perlecan Is Critical for Heart Stability", Cardiovascular Research, 80(3): 435-444, Published Online Aug. 10, 2008. Abstract, p. 440-441, Section 3.4.

Search Report—ILPO Dated May 26, 2016 From the Israel Patent Office Re. Application No. 242380.

Sharma et al. "Local Drug Delivery for Percutaneous Coronary Intervention", Pharmacology & Therapeutics, 129(3): 260-266, Published Online Nov. 25, 2010.

Singhai et al. "Role of Extracellular Matrix Proteins and Their Receptors in the Development of the Vertebrate Neuromuscular Junction". Developmental Neurobiology 71(11):982-1005, Nov. 2011.

Translation Dated Jun. 20, 2021 of Notification of Office Action and Search Report Dated Mar. 1, 2021 From the National Intellectual Property Administration of the People's Republic of China Re. Application No. 201680077347.7. (10 Pages).

Xu et al. "A Murine Model of Myocardial Ischemia-Reperfusion Injury through Ligation of the Left Anterior Descending Artery", Journal of Visualized Experiments, 86: e51329-I-e51329-7, 2014.

Yurchenco et al. "Recombinant Laminin G Domain Mediates Myoblast Adhesion and Heparin Binding", The Journal of Biological Chemistry, 268( 11 ): 8356-8365. Apr. 15, 1993. Abstract.

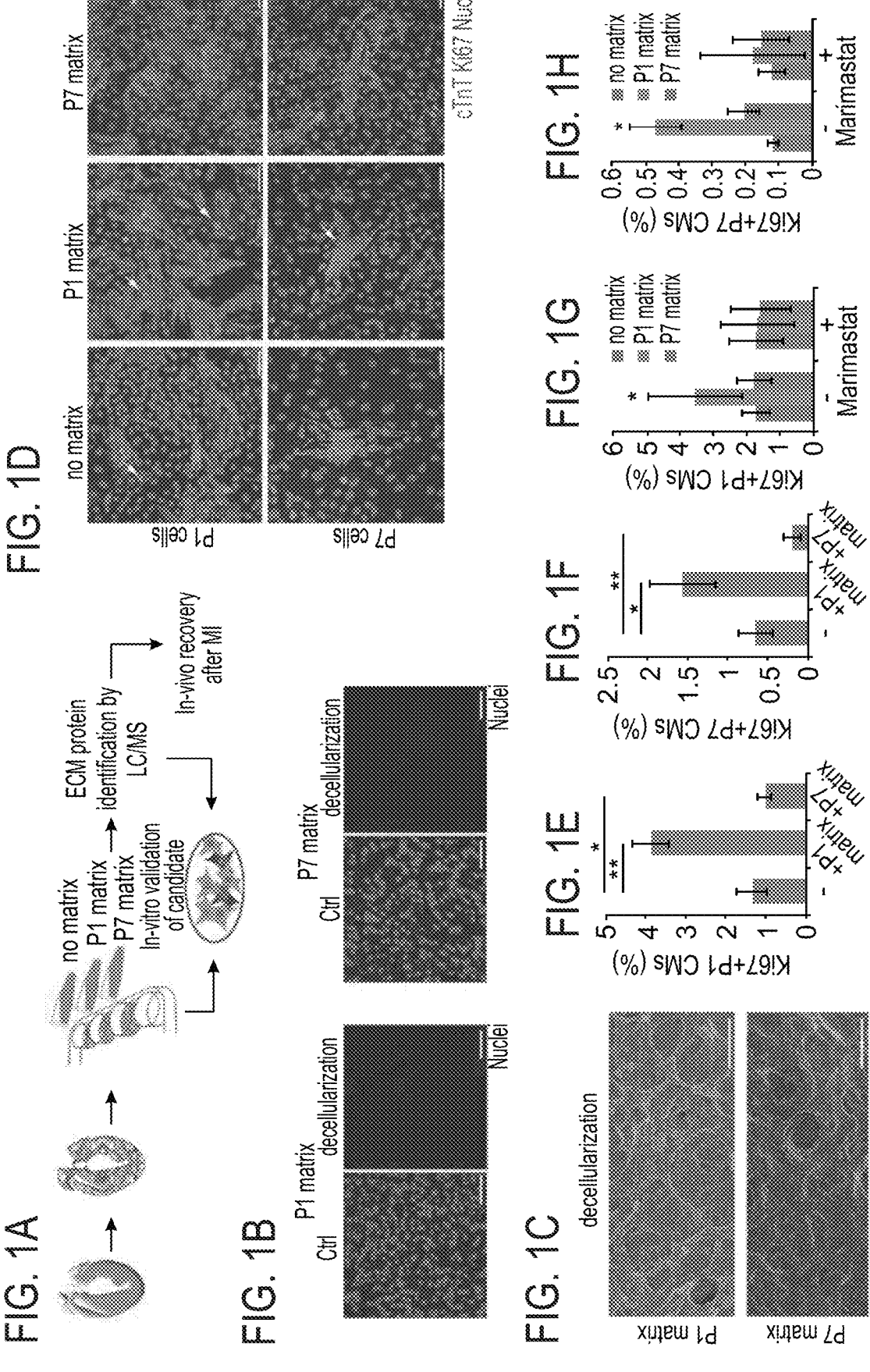

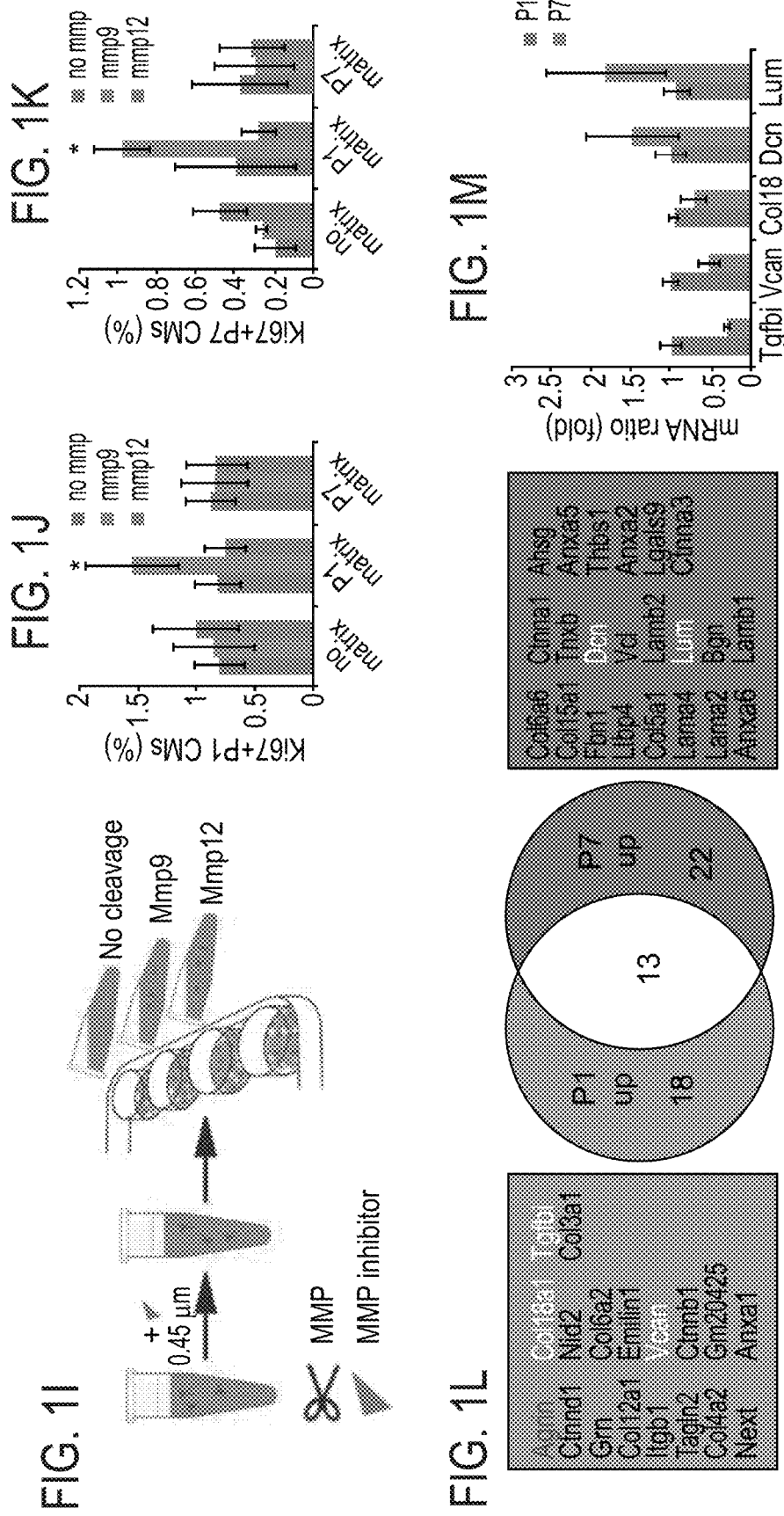

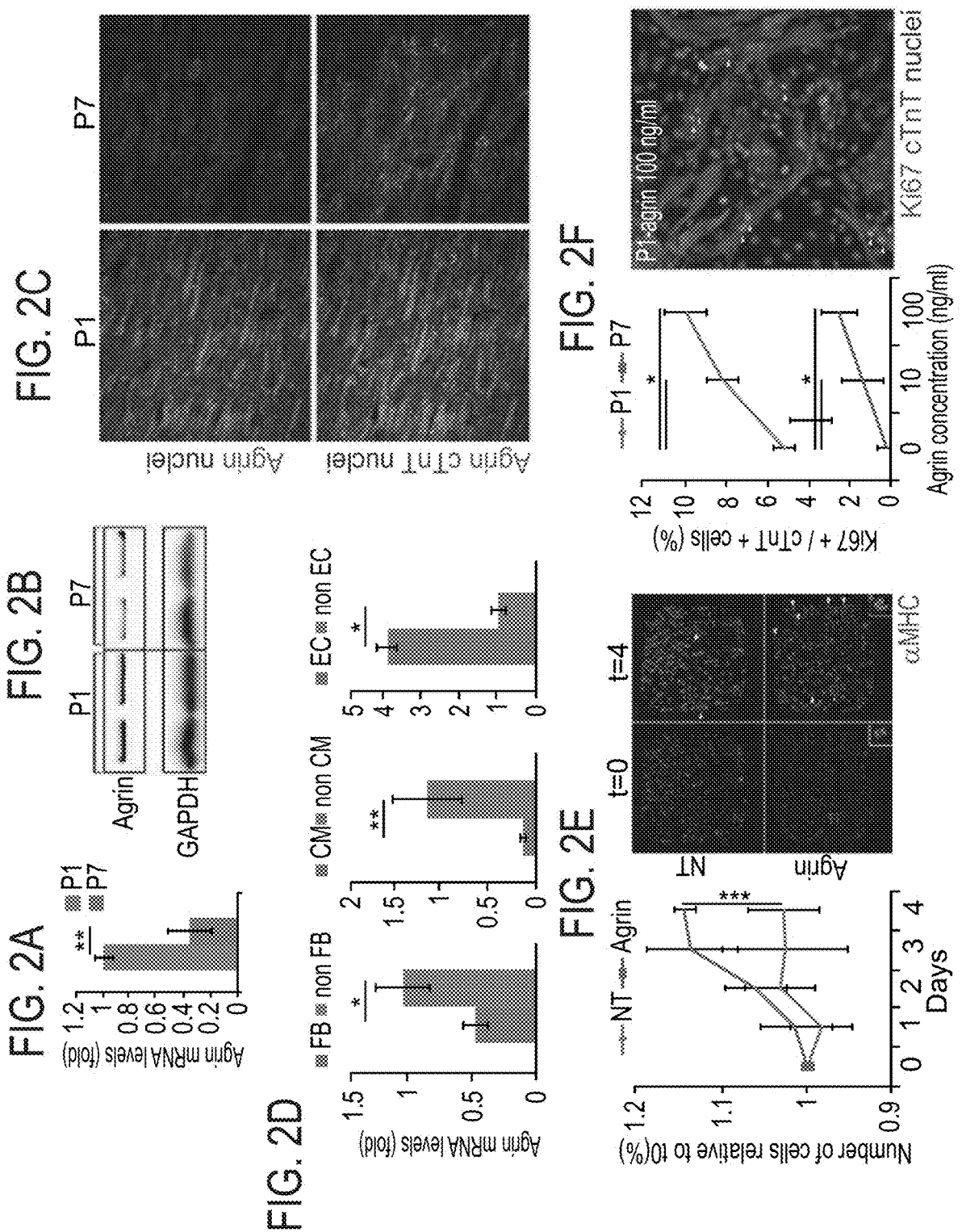

Resection    Proliferation analysis    Fibrosis analysis

P1    P7    p28

Apical resection

None (scar=0%)
Moderate (scar<1%)
Large (scar>1%)

WT    cKO

WT    cKO

Scarring (%/LV wall)

WT    cKO

Ki67+ CMs (%)

cTnT Ki67 Nuclei

Aim1 CMs (%)

Aim1 cTnI Nuclei

Adult MI

FIG. 4G
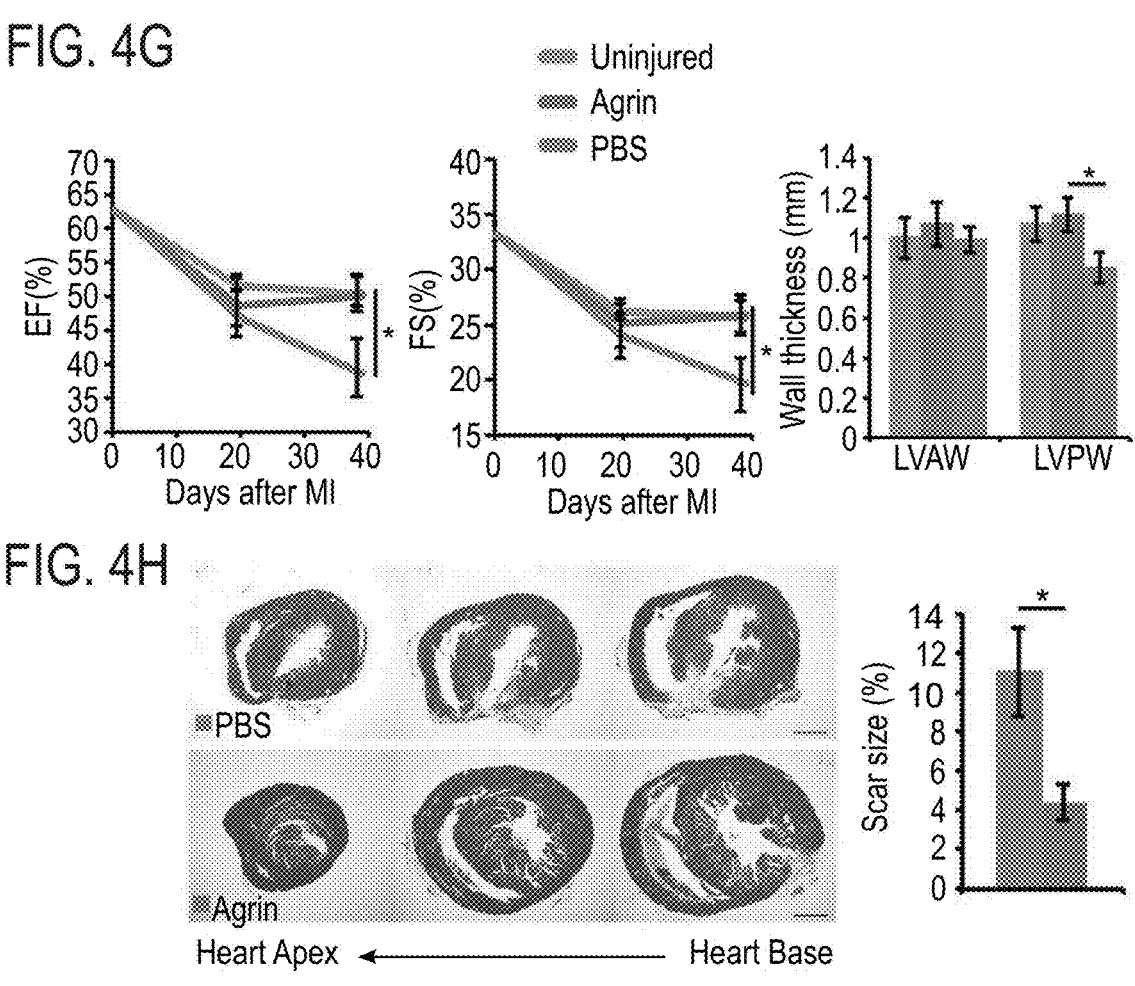
FIG. 4H
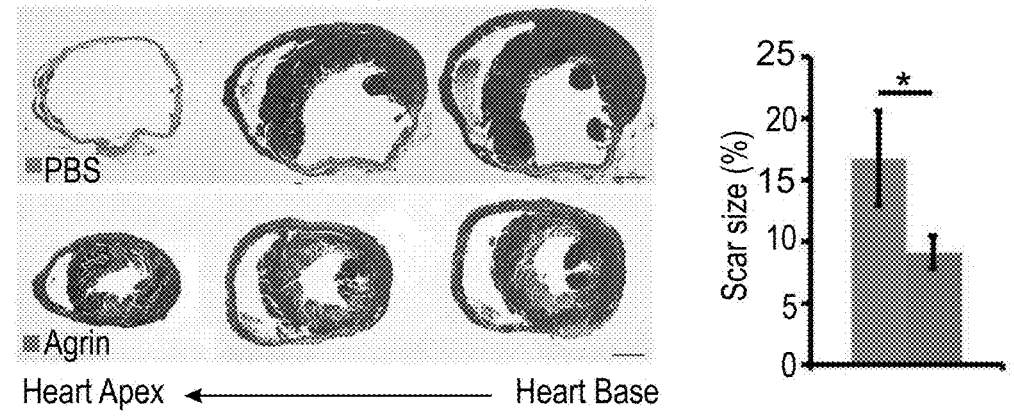
FIG. 4I

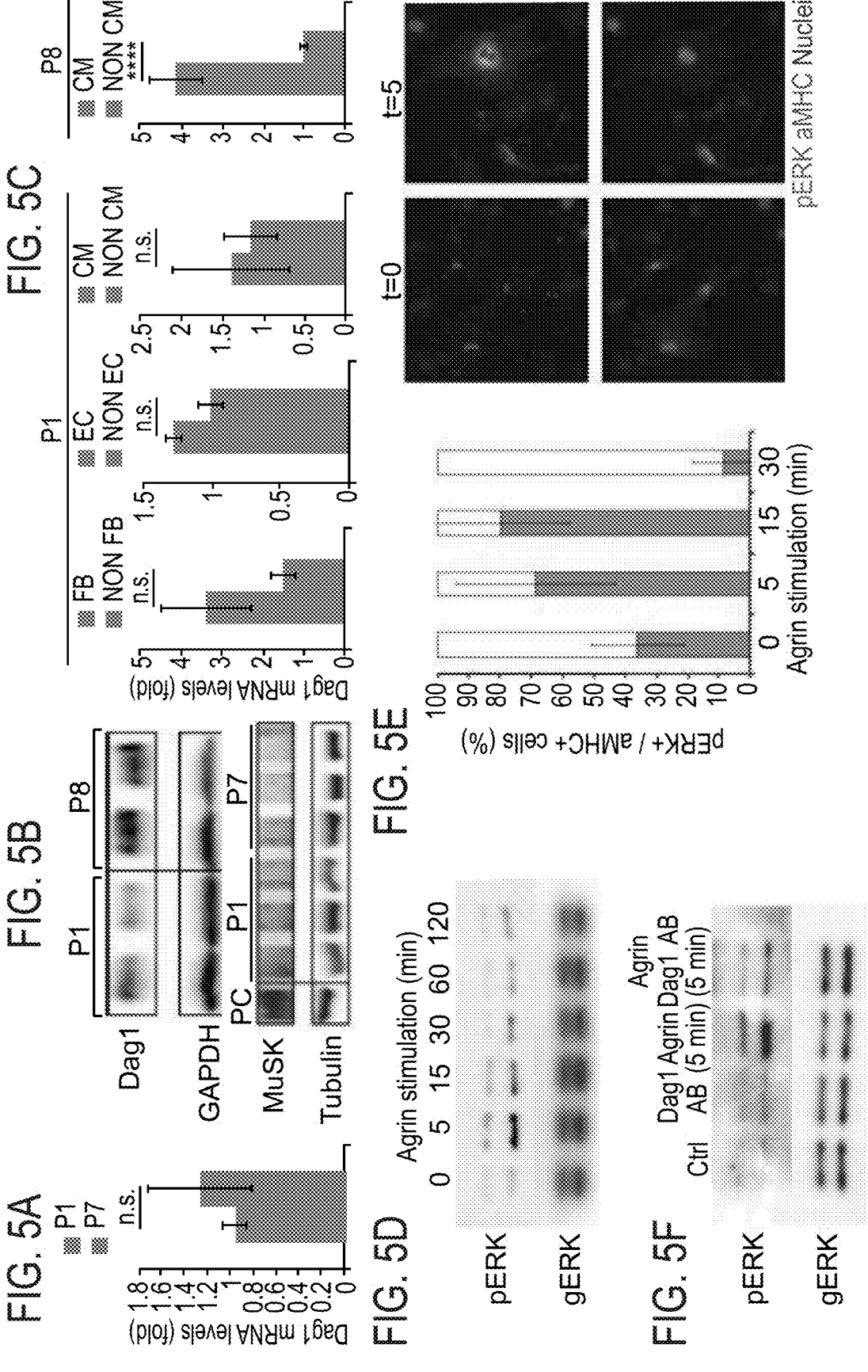

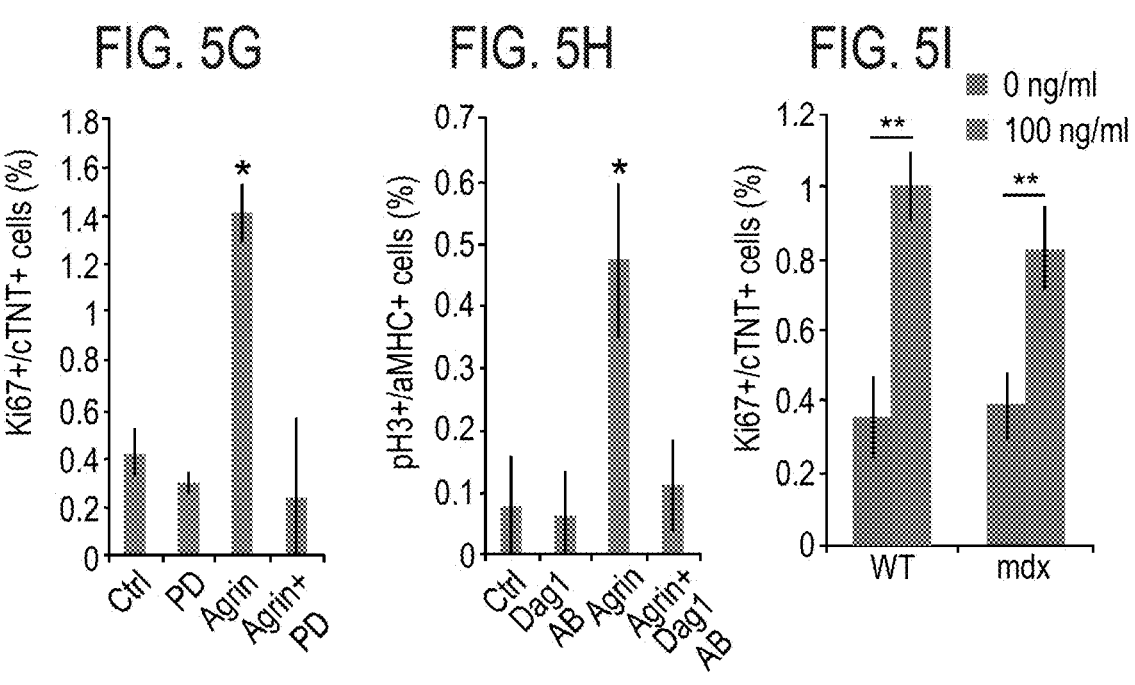
FIG. 5G
FIG. 5H
FIG. 5I
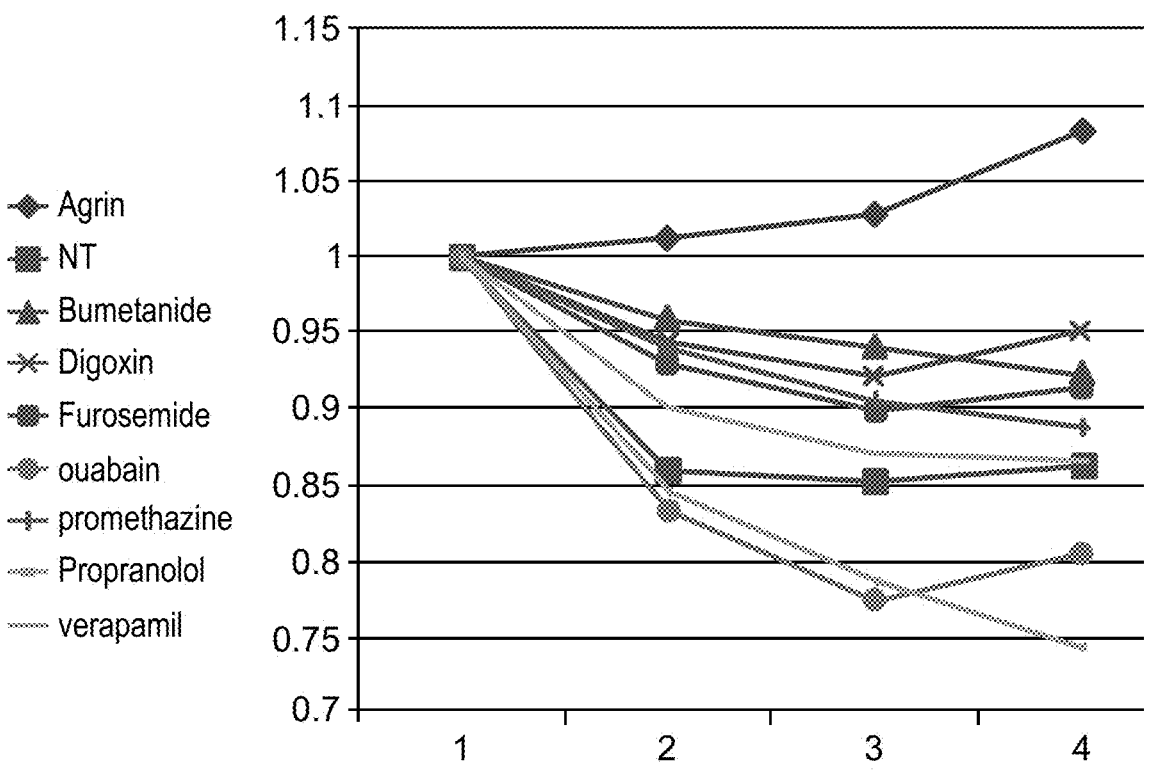
FIG. 5J

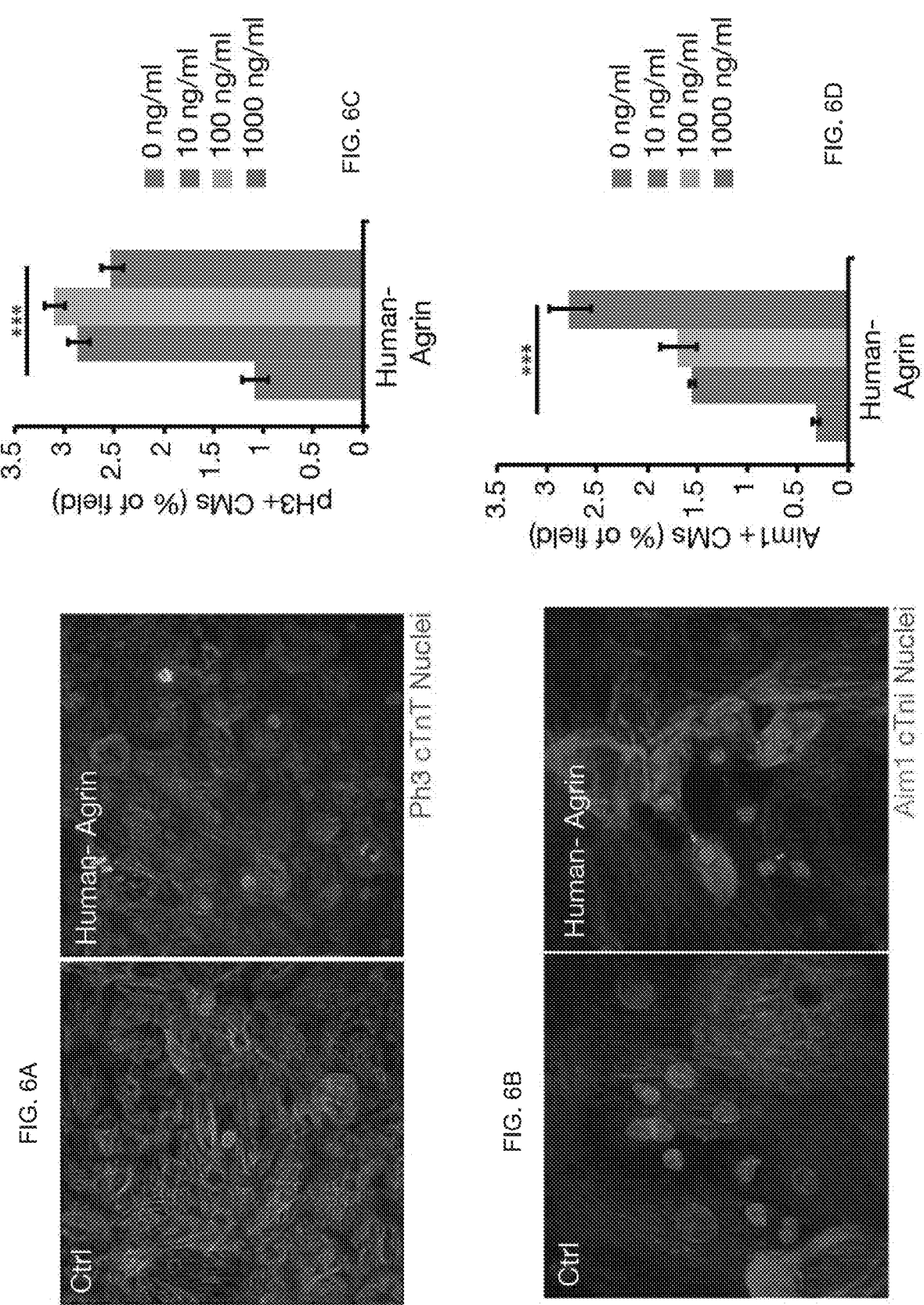

| | | |
|---|---|---|
| Human_Agrin | MAGRSHPGPLRPLLPLLVVAACVLPGAGGTCPERALERREEEANVVLTGTVEEILNVDPV | 60 |
| Rat_Agrin | ------------------------------------------------------------ | 0 |
| Recombinat_Agrin | ------------------------------------------------------------ | 0 |
| | | |
| Human_Agrin | QHTYSCKVRVWRYLKGKDLVARESLLDGGNKVVISGFGDPLICDNQ--VSTGDT--RIFF | 115 |
| Rat_Agrin | -------------------------------------MPPLPLEHRPRQEPGASMLVRYF | 23 |
| Recombinat_Agrin | ------------------------------------------------------------ | 0 |
| | | |
| Human_Agrin | VNPAPPYLWPAHKNELMLNSSLMRITLRNLEEVEFCVEDKPGTHFTPVPPTPPDACRGML | 176 |
| Rat_Agrin | -------MIPCNICLI-----LLATSTLGFAVLLFLSNYKPGIHFTPAPPTPPDVCRGML | 71 |
| Recombinat_Agrin | ------------------------------------------------------------ | 0 |
| | | |
| Human_Agrin | CGFGAVCEPNAEGPGRASCVCKKSPCPSVVAPVCGSDASTYSNECELQRAQCSQQRRIRL | 236 |
| Rat_Agrin | CGFGAVCEPSVEDPGRASCVCKKNACPATVAPVCGSDASTYSNECELQRAQCNQQRRIRL | 131 |
| Recombinat_Agrin | ------------------------------------------------------------ | 0 |
| | | |
| Human_Agrin | LSRGPCGSRDPCSNVTCSFGSTCARSADGLTASCLCPATCRGAPEGTVCGSDGADYPGEC | 296 |
| Rat_Agrin | LRQGPCGSRDPCANVTCSFGSTCVPSADGQTASCLCPTTCFGAPDGTVCGSDGVDYPSEC | 191 |
| Recombinat_Agrin | ------------------------------------------------------------ | 0 |
| | | |
| Human_Agrin | QLLRRACARQENVFKKFDGPCDPCQGALPDPSRSCRVNPRTRRPEMLLRPESCPARQAPV | 356 |
| Rat_Agrin | QLLSHACASQEIHFKKFNGPCDPCQGSMSDLNHICRVNPRTRHPEMLLRPENCPAQHTPI | 251 |
| Recombinat_Agrin | ------------------------------------------------------------ | 0 |
| | | |
| Human_Agrin | CGDDGVTYENDCVMGRSGAARGLLLQKVREGQCQGRDQCPEPCRFNAVCLSRRGRPRCSC | 416 |
| Rat_Agrin | CGDDGVTYENDCVMSRIGATRGLLLQKVRSGQCQTRDQCPETCQFNSVCLSRRGRPHCSC | 311 |
| Recombinat_Agrin | ------------------------------------------------------------ | 0 |
| | | |
| Human_Agrin | DRVTCDGAYRPVCAQDGRTYDSDCWRQQAECRQQRAIPSKHQGPCDQAPSPCLGVQCAFG | 476 |
| Rat_Agrin | DRVTCDGSYRPVCAQDGHTYNNDCWRQQAECRQQRAIPSKHQGPCDQTPSPCHGVQCAFG | 371 |
| Recombinat_Agrin | ------------------------------------------------------------ | 0 |
| | | |
| Human_Agrin | ATCAVKNGDAACECLQACSSLYDPVCGSDGVTYGSACELEATACTLGREIQVARKGPCDR | 536 |
| Rat_Agrin | AVCTVKNGKAECECQRVCSGIYDPVCGSDGVTYGSVCELESMACTLGREIQVARRGPCDP | 431 |
| Recombinat_Agrin | ------------------------------------------------------------ | 0 |
| | | |
| Human_Agrin | CGQCRFGALCEAETGRCVCPSECVALAQPVCGSDGHTYPSECMLHVHACTHQISLHVASA | 596 |
| Rat_Agrin | CGQCRFGSLCEVETGRCVCPSECVESAQPVCGSDGHTYASECELHVHACTHQISLYVASA | 491 |
| Recombinat_Agrin | ------------------------------------------------------------ | 0 |
| | | |
| Human_Agrin | GPCETCGDAVCAFGAVCSAGQCVCPRCEHPPPGPVCGSDGVTYGSACELREAACLQQTQI | 656 |
| Rat_Agrin | GHCQTCGEAVCAFGAVCSAGQCVCPRCEHPPPGPVCGSDGVTYLSACELREAACQQQVQI | 551 |
| Recombinat_Agrin | ------------------------------------------------------------ | 0 |
| | | |
| Human_Agrin | EEARAGPCEQAECGSGGSGSGEDGDCEQELCRQRGGIWDEDSEDGPCVCDFSCQSVPGSP | 716 |
| Rat_Agrin | EEAHAGPCEPAECGSGGSGSGEDDECEQELCRQRGGIWDEDSEDGPCVCDFSCQSVPGSP | 611 |
| Recombinat_Agrin | ------------------------------------------------------------ | 0 |

FIG. 7B

```
Human_Agrin       VCGSDGVTYSTECELKKARCESQRGLYVAAQGACRGPTFAPLPPVAPLHCAQTPYGCCQD     776
Rat_Agrin         VCGSDGVTYSTECELKKARCESQRGLYVAAQGACRGPTFAPLPPVAPLHCAQTPYGCCQD     671
Recombinat_Agrin  ------------------------------------------------------------     0

Human_Agrin       NITAARGVGLAGCPSACQCNPHGSYGGTCDPATGQGSCRPGVGGLRCDRCEPGFWNFRGI     836
Rat_Agrin         NITAARGVGLAGCPSACQCNPHGSYGGTCDPATGQGSCRPGVGGLRCDRCEPGFWNFRGI     731
Recombinat_Agrin  ------------------------------------------------------------     0

Human_Agrin       VTDGRSGCTPCSCDPQGAVRDDCEQMTGLCSCKPGVAGPKCGQCPDGRALGPAGCEADAS     896
Rat_Agrin         VTDGHSGCTPCSCDPQGAVRDDCEQMTGLCSCRPGVAGPKCGQCPDGQVLGHLGCEADPM     791
Recombinat_Agrin  ------------------------------------------------------------     0

Human_Agrin       APATCAEMRCEFGARCVEESGSAHCVCPMLTCPEANATKVCGSDGVTYGNECQLKTIACR     956
Rat_Agrin         TPVTCVEIHCEFGASCVEKAGFAQCICPTLTCPEANSTKVCGSDGVTYGNECQLKAIACR     851
Recombinat_Agrin  ------------------------------------------------------------     0

Human_Agrin       QGLQISIQSLGPCQEAVAPSTHPTSASVTVTTPGLLLSQALPAPPGALPLAPSSTAHSQT     1016
Rat_Agrin         QRLDISTQSLGPCQESVTPGASPTSASM--TTPRHILSKTLPFPHNSLPLSPGSTTHDWP     909
Recombinat_Agrin  ------------------------------------------------------------     0

Human_Agrin       TPPPSSRPRTTASVPRTTVWPVLTVPPTAPS-PAPSLVASAFGESGSTDGSSDEELSGDQ     1075
Rat_Agrin         TPLPI-SPHTTVSIPRSTVWPVLTVPPTAAASDVTSLATSIFSESGSANGSGDEELSGDE     968
Recombinat_Agrin  ------------------------------------------------------------     0

Human_Agrin       EASGGGSGGLEPLEGSSVATPGPPVERASCYNSALGCCSDGKTPSLDAEGSNCPATKVFQ     1135
Rat_Agrin         EASGGGSGGLEPPVGSIVVTHGPPIERASCYNSPLGCCSDGKTPSLDSEGSNCPATKAFQ     1028
Recombinat_Agrin  ------------------------------------------------------------     0

Human_Agrin       GVLELEGVEGQELFYTPEHADPKSELFGETARSIESTLDDLFRNSDVKKDFRSVRLRDLG     1195
Rat_Agrin         GVLELEGVEGQELFYTPEMADPKSELFGETARSIESTLDDLFRNSDVKKDFWSVRLRELG     1088
Recombinat_Agrin  ------------------------------------------------------------     0

Human_Agrin       PGKSVRAIVDVHFDPTTAFRAPDVARALLRQIQVSRRRSLGVRRPLQEHVRFMDFCWFPA     1255
Rat_Agrin         PGKLVRAIVDVHFDPTTAFQASDVGQALLRQIQVSRPWALAVRRPLQEHVRFLDFDWFPT     1148
Recombinat_Agrin  ------------------------------------------------------------     0

Human_Agrin       FITGATSGAIAAGATARATTASRLPSSAVTPRAPHPSHTSQPVAKTTAAPTTRRPPTTAP     1315
Rat_Agrin         FFTGAATGTTAAMATARATTVSRLPASSVTPRV-YPSHTSRPVGRTTAAPTTRRPPTTAT     1207
Recombinat_Agrin  ----AATGTTAAMATARATTVSRLPASAVTPRV-YPSHTSRPVGRTTAPPTTRRPPTTAT     55
                  *..*. ** *******.****.*.****.  .*****.** .*** **********
```

FIG. 7B Continuous

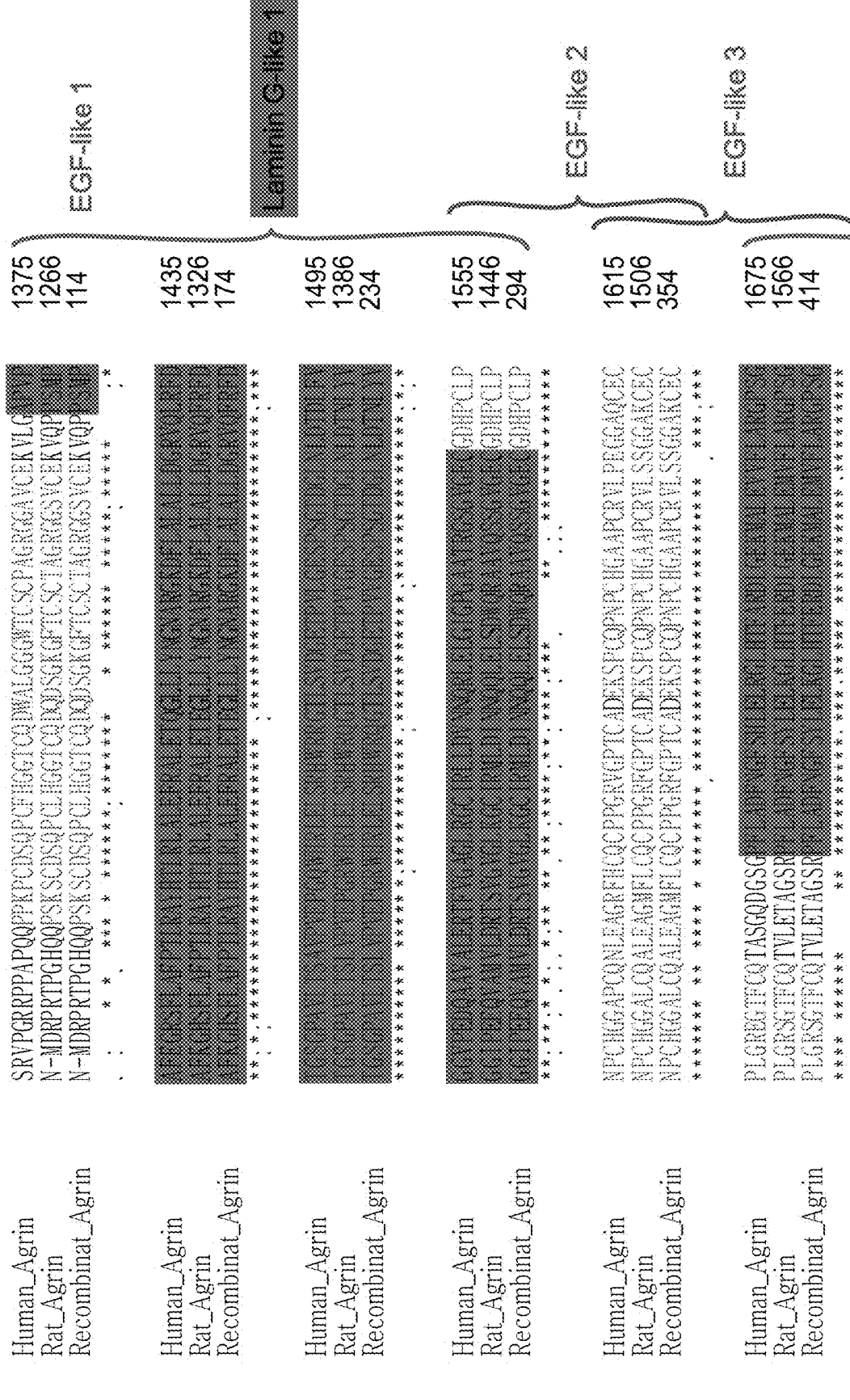
FIG. 7B Continuous

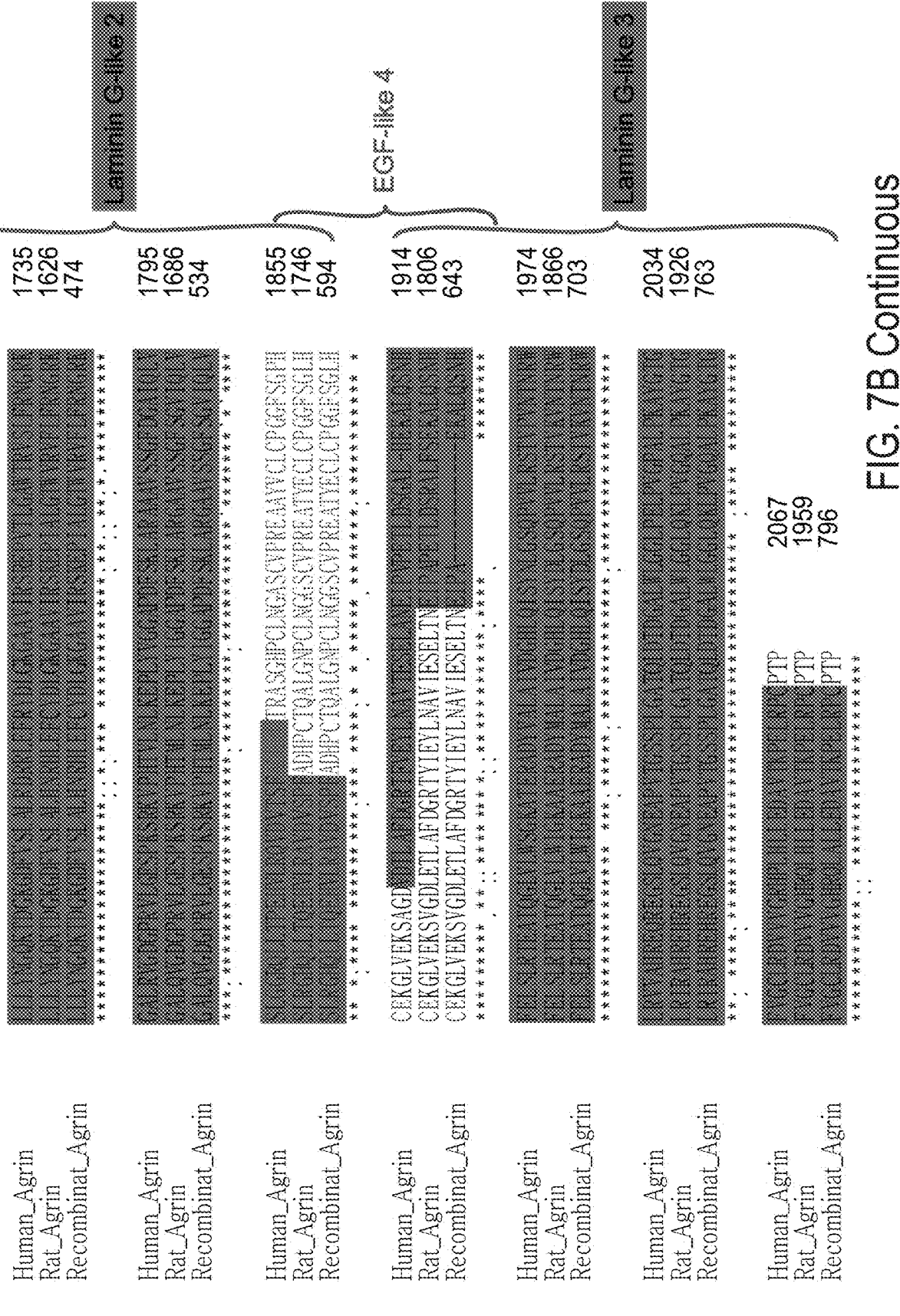
FIG. 7B Continuous

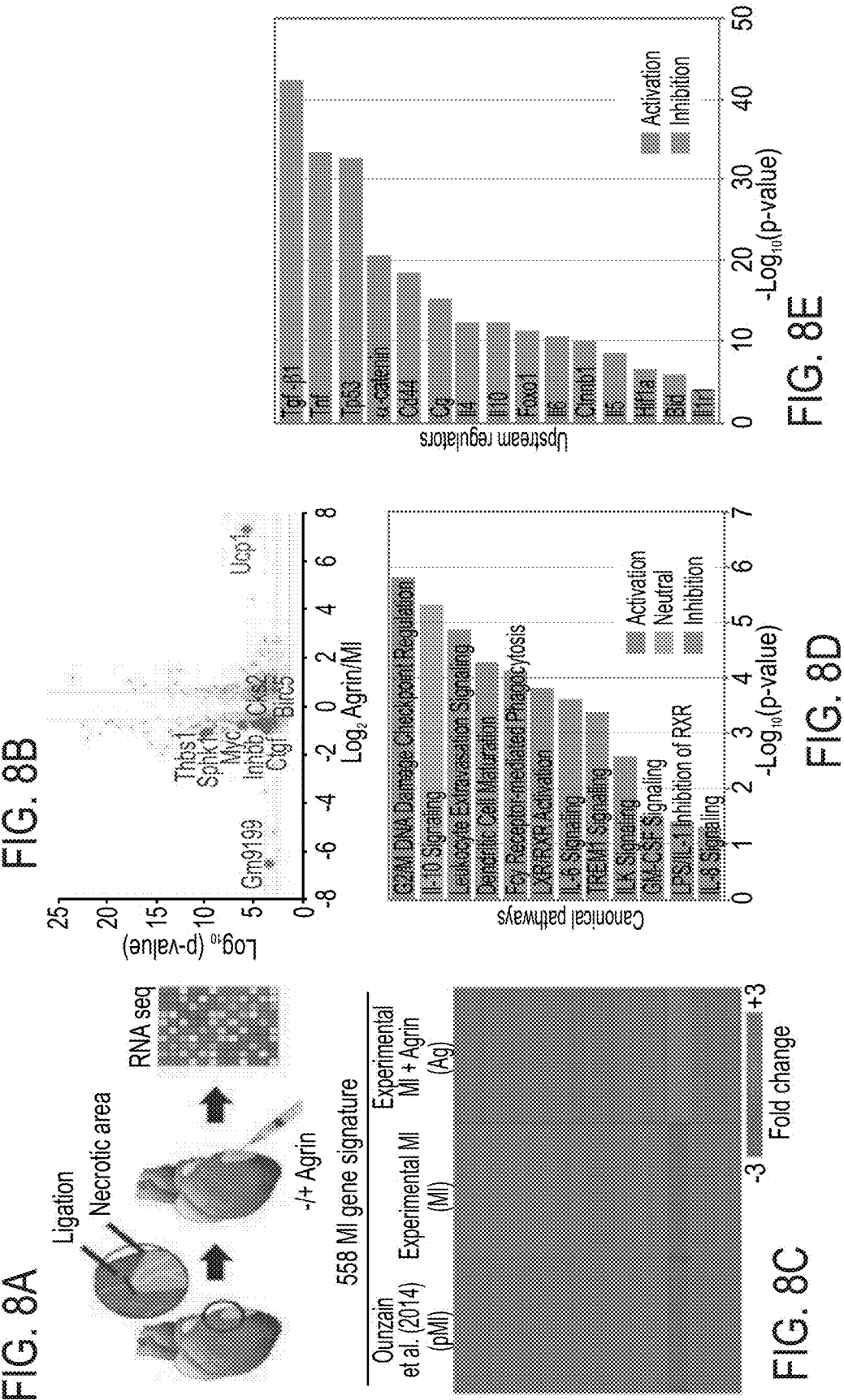

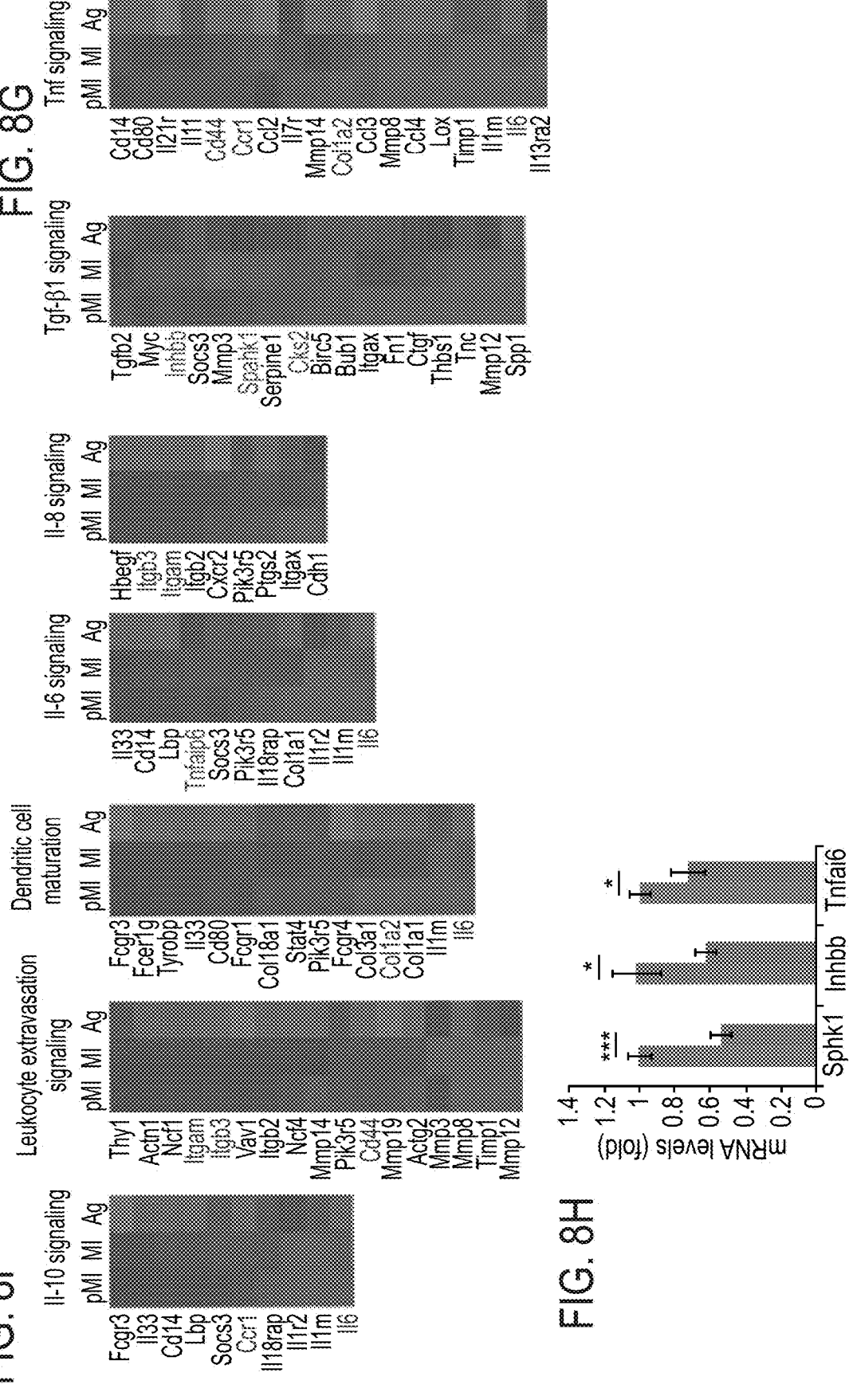

METHOD OF INDUCING CARDIOMYOCYTES PROLIFERATION AND TREATING HEART DISEASES

RELATED APPLICATIONS

This application is a continuation of U.S. patent application Ser. No. 16/746,878, filed Jan. 19, 2020, which application is a continuation of U.S. patent application Ser. No. 15/772,065 filed on Apr. 29, 2018, which is a national phase of PCT Patent Application No. PCT/IL2016/051165 having International Filing Date of Oct. 27, 2016, which claims the benefit priority of Israel Patent Application No. 242380 filed on Oct. 29, 2015. The contents of the above applications are all incorporated by reference as if fully set forth herein in their entirety.

SEQUENCE LISTING STATEMENT

The XML file, entitled 133567-0220_SL.xml, created on Feb. 10, 2025, comprising 72,527 bytes, submitted concurrently with the filing of this application is incorporated herein by reference. The contents of the sequence listing submitted herewith is identical to the contents of the sequence listing forming part of the international application.

FIELD AND BACKGROUND OF THE INVENTION

The present invention, in some embodiments thereof, relates to methods of inducing proliferation of cardiomyocytes and methods of treating heart diseases.

Heart disease and in particular myocardial infarction (MI), is the leading cause of death in the world. The severity of heart disease is due to the post-mitotic nature of mammalian adult cardiac muscle cells—the cardiomyocytes (CMs) {Bergmann, 2009 #9; Senyo, 2013 #86} and their limited capacity to replenish damaged tissue {Poss, 2007 #30; Auson, 2009 #17}. In contrast, extensive CM proliferation and subsequently robust cardiac regeneration occurs in lower vertebrates such as newt {Ausoni, 2009 #17} and zebrafish {Poss, 2007 #30; Jopling, 2010 #68; Ausoni, 2009 #17}. Similarly, neonatal murine CM turnover is sufficient to repair damaged myocardium following injury; however this ability is greatly diminished during the first week after birth {Porrello, 2011 #11; Porrello, 2012 #38}. During this time, there is a transition in CM ploidy from mono to bi-nucleation, concurrent with a switch from hyperplasia (increase in cell number) to hypertrophy (increase in cell size) {Li, 1996 #61; Soonpaa, 1998 #89}. Induced cardiac injury in mice at the day of birth results in nearly complete regeneration however this capacity is diminished by day 7. At this time point fibrotic scar dominates the replenishment of muscle tissue through CM proliferation {Porrello, 2011 #11} therefore leading to impaired cardiac function {Weisman, 1988 #90}. Many studies focus on the proliferation of endogenous CMs in order to contribute to heart regeneration. Recently, it was shown that adult CMs can re-enter the cell cycle and proliferate by modulating several pathways such as: FGF1 accompanied with P38 inhibition {Engel, 2006 #127}, extracellular Periostin {Kuhn, 2007 #28}. NRG1 via Erbb2 {D'Uva, 2015 #99; Bersell, 2009 #128} Hippo inhibition {Heallen, 2013 #100} and inhibition of the cell cycle regulator Meis1 {Mahmoud, 2013 #80}.

Heart pathologies, primarily MI, are often accompanied by ECM remodeling, mainly deposition of a rigid scar which reduces heart function {Weisman, 1988 #90; Baum, 2011 #12; Bayomy, 2012 #3}. Alterations in ECM structure following injury are attributed to activity of matrix metalloproteases (MMPs) {Phatharajaree, 2007 #92}, mainly the gelatinase family, MMP2 and MMP9 {DeCoux, 2014 #91}. Deletion of either MMP2 {Hayashidani, 2003 #94} or MMP9 {Ducharme, 2000 #93} following MI attenuated ECM remodeling and improved overall heart function. Despite the adverse effects of ECM remodeling following cardiac injury. ECM plays an integral role in cellular migration {Ridley, 2003 #95; Berk, 2007 #97}, differentiation {Shamis, 2011 #18; Streuli, 1999 #96} and proliferation {Berk, 2007 #97} of any cell type.

Through utilization of ECM decellularization and acid solubilization of fetal, neonatal and adult cardiac ECM, cardiac ECM was shown to significantly contribute to the regulation of CM proliferation {Williams, 2014 #84}. Seeded on neonatal cells. ECM derived from fetal and neonatal ages displayed higher proliferation levels compared to adult derived ECM {Williams, 2014 #84}. Although manipulation of CM intrinsic factors was shown to expand the proliferative capacity of the mammalian heart {D'Uva, 2015 #99; Mahmoud, 2013 #80; Heallen, 2013 #100}, the roles of the extracellular environment or its components in cardiac regeneration remain unclear.

Agrin is an extracellular heparan sulfate proteoglycan (HSPG) with a core protein size of 210 kDa {Williams, 2008 #71}. The neural form of Agrin (n-Agrin) has been extensively researched due to its involvement in the aggregation of acetylcholine receptors (AChRs) via the muscle specific kinase (MuSK)-Lrp4 receptor complex {Burden, 2013 #76}. Elevated expression of non-neuronal Agrin has been correlated with several types of carcinoma {Theocharis, 2010 #102} and more recently has been implicated in the progression of hepatocellular carcinoma (HCC) by controlling motility and proliferation of cells through interaction with Lrp4 {Chakraborty, 2015 #101}. Additionally, a small fragment of Agrin (the c-terminal 22 kDa peptide CAF22) has been shown to hind and inhibit Na+ K+ channels that modulate CM beating {Hilgenberg, 2009 #103}, similarly to Digoxin, a drug commonly taken after various cardiac episodes {Hilgenberg, 2009 #103; Schwinger, 2003 #104}. A recent study focused on the interaction of Agrin with the dystroglycan complex as a key component in processes of innate immunity, and is required for monocyte and macrophage differentiation through interaction with Grb2 and subsequent ERK activation {Mazzon, 2012 #73}.

Dystroglycan is comprised of two units ($\alpha$ and $\beta$) {Henry, 1996 #105} and acts as a transmembrane bridge connecting ECM components (such as Agrin, Laminin and Perlecan) with the muscle cell inner myoskeleton by interacting with Dystrophin and its associated complex {Henry, 1996 #105; Davies, 2006 #106; Ervasti, 1990 #108}. Interruption of Dystrophin complex is the leading cause for various muscular dystrophies including Duchenne muscular dystrophy {Davies, 2006 #106; Campbell, 1989 #107; Ervasti, 1990 #108}. Mice lacking Dystrophin (Mdx), present elevated CM turnover in non-ischemic cardiomyopathy model {Richardson, 2015 #110}; In contrast, a recent study that employed post-natal day 1 heart resection on Mdx mice revealed impaired regenerative response and elevated fibrosis relative to wildtype mice {Morikawa, 2015 #109}. Nonetheless, the role of Agrin. Dystroglycan and their downstream elements has never been studied in the context of cardiac regeneration.

Additional background art includes:

U.S. Application Number 20070014871

U.S. Application Number 20100095387
U.S. Application Number 20060223753
U.S. Application Number 20140377212
U.S. Application Number 20110104120
U.S. Application Number 20070014733

SUMMARY OF THE INVENTION

According to an aspect of some embodiments of the present invention there is provided use of a therapeutically effective amount of an Agrin peptide which induces proliferation of cardiomyocytes in the manufacture of a medicament for treating a heart disease.

According to an aspect of some embodiments of the present invention there is provided use of an agent which inhibits the Dystroglycan complex on cardiomyocytes in the manufacture of a medicament for treating a heart disease.

According to an aspect of some embodiments of the present invention there is provided a method of inducing proliferation of cardiomyocytes, the method comprising contacting the cardiomyocytes with an effective amount of an Agrin peptide which induces proliferation of the cardiomyocytes.

According to an aspect of some embodiments of the present invention there is provided a method of inducing proliferation of cardiomyocytes, the method comprising contacting the cardiomyocytes with an agent which inhibits the Dystroglycan complex on the cardiomyocytes, thereby inducing proliferation of cardiomyocytes.

According to some embodiments of the invention, the agent is selected from the group consisting of a small molecule and a peptide and a polynucleotide.

According to some embodiments of the invention, the agent comprises an agrin peptide which induces proliferation of the cardiomyocytes.

According to some embodiments of the invention, the agent induces Erk activation.

According to some embodiments of the invention, the agent inhibits sarcomerogenesis.

According to an aspect of some embodiments of the present invention there is provided a method of treating a heart disease in a subject in need thereof, the method comprising administering to the subject a therapeutically effective amount of an Agrin peptide which induces proliferation of cardiomyocytes, thereby treating the heart disease.

According to an aspect of some embodiments of the present invention there is provided an implantable device comprising an Agrin peptide which induces proliferation of cardiomyocytes.

According to some embodiments of the invention, the Agrin peptide is not a part of a fusion polypeptide.

According to some embodiments of the invention, the Agrin peptide is in a soluble form.

According to some embodiments of the invention, the Agrin peptide comprises a Laminin G-like 1 domain (G1) and a Laminin G-like 2 domain (G2).

According to some embodiments of the invention, the Agrin peptide is 90-110 KDa.

According to some embodiments of the invention, the Agrin peptide comprises a fragment of human Agrin.

According to some embodiments of the invention, the cardiomyocytes are selected from the group consisting of adult cardiomyocytes, juvenile cardiomyocytes and neonatal cardiomyocytes.

According to some embodiments of the invention, the method is effected in vivo.

According to some embodiments of the invention, the method is effected ex vivo.

According to some embodiments of the invention, the method is effected in vitro.

According to some embodiments of the invention, the cardiomyocytes are comprised in a tissue.

According to some embodiments of the invention, the heart disease is an ischemic heart disease.

According to an aspect of some embodiments of the present invention there is provided an isolated peptide comprising Laminin G-like 2 (G2) domain the peptide being no more than 200 amino acids in length.

According to some embodiments of the invention, the peptide is as set forth in SEQ ID NO: 8.

According to an aspect of some embodiments of the present invention there is provided a pharmaceutical composition comprising the peptide.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL
VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 1A-1M show that P1 cardiac ECM increases CM cell cycle reentry in an MMP dependent manner. (FIG. 1A) Experimental design for ECM contribution to CM cell cycle reentry in P1 and P7 cultures. (FIG. 1B) Heart sections were stained with DAPI in order to assess the removal of cells. (FIG. 1C) Sections were Imaged by SEM, treated samples are free of cellular components. (FIG. 1D) Representative fields of heart cultures stained with DAPI (blue) cTNT (green) and Ki67 (red). White arrows display Ki67+/cTNT+ cells. (FIGS. 1E-1F) P1 (FIG. 1E) or P7 (FIG. 1F) percent of proliferating CMs in response to day 1 and day 7 ECM. (FIGS. 1G-1H) P1 (FIG. 1G) or P7 (FIG. 1H) percent of proliferating CM (Ki67+/cTNT+) cells in response to day 1 and day 7 ECM with or without broad MMP inhibitor (marimastat), (FIG. 1I) Scheme of MMP derived ECM fragments contribution to CM cell cycle activity. (FIGS. 1J-1K) Percent of P1 (FIG. 1J) or P7 (FIG. 1K) proliferating CMs in response to the presence of MMP9/12 cleaved substrates of day 1 and day 7 ECM fragments. (FIG. 1I) Van diagram presenting the LC/MS results. (FIG. 1M) Quantitative PCR (qPCR) analysis of genes obtained from the LC/MS in P1 and P7 whole heart lysates.

FIGS. 1N-1P show that P1 and P7 ECM promote elevated gelatinase activity. (FIG. 1N) A schematic diagram in situ zymography (ISZ) assay. (FIG. 1O) Immunofluorescence evaluation of Col1, Col4 and gelatin degradation in response to P1 and P7 ECM. (FIG. 1P) Quantification of ISZ assay.

Figures 2G, 2H, 2I:
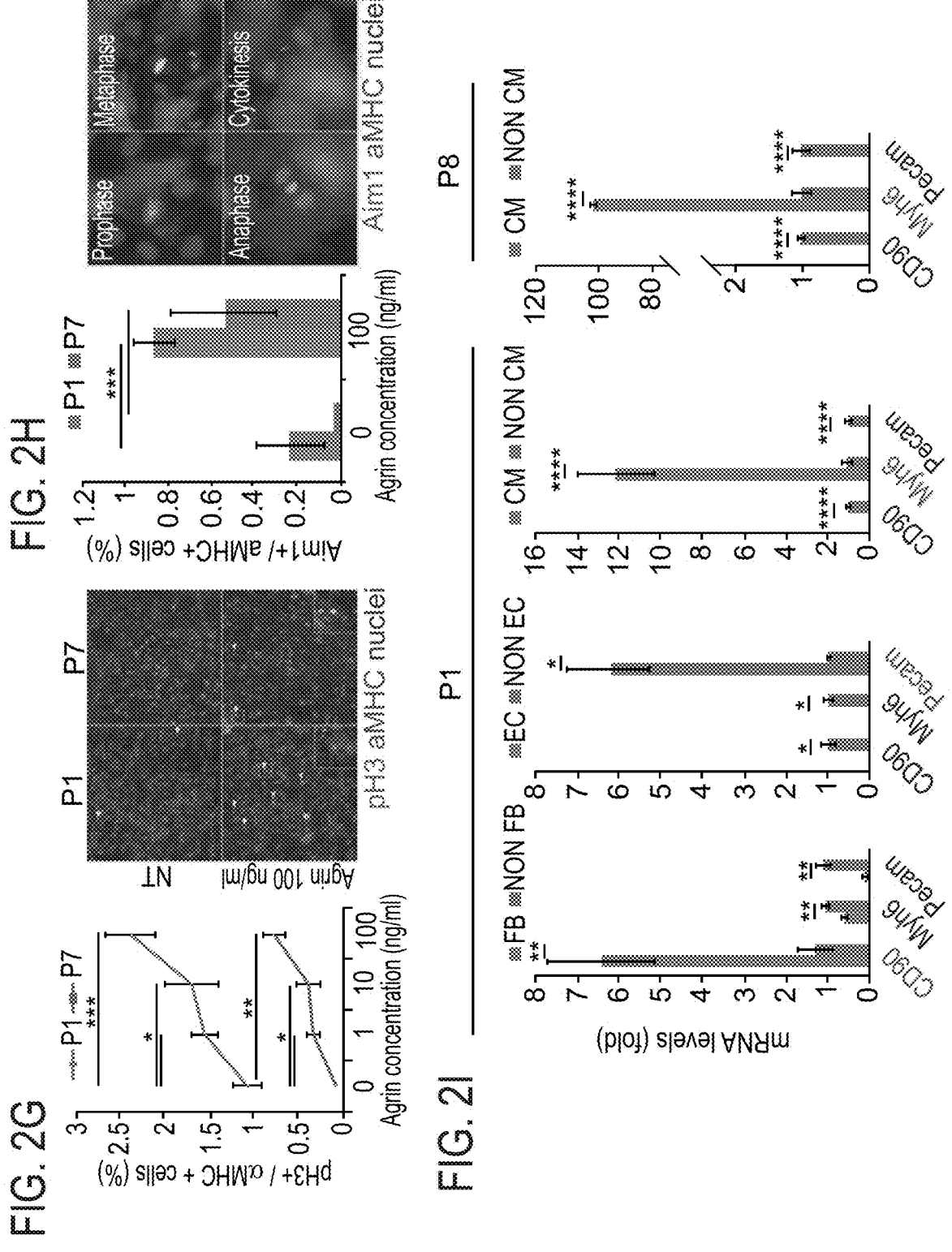

FIGS. 2A-2I show that endocardial derived Agrin promotes CM proliferation. (FIG. 2A) qPCR of Agrin gene from P1 and P7 heart lysates. (FIG. 2B) Western blot analysis of Agrin from P1 and P7 heart lysates. (FIG. 2C) Images of P1 and P7 heart sections stained for Agrin (green) cTnT (red) and counterstained with DAPI (blue). (FIG. 2D) qPCR analysis of 6 cell populations (FB, non-FB, CM, non-CM, EC, non-EC) for Agrin. Immunofluorescence evaluation of P1 and P7 CM (cTnT or tomato-$\alpha$MHC) number (FIG. 2E), cell cycle (Ki67; FIG. 2F) mitosis (pH3; FIG. 2G) or cytokinesis (Aim1; FIG. 2H) in response to Agrin administration in vitro. (FIG. 2I) qPCR of genes from P1 and P8 heart lysate, qPCR analysis of 6 cell populations (FB, non-FB, CM, non-CM, EC, non-EC) for CD90 (FB marker), $\alpha$MHC (CM marker) and Pecam (EC marker).

Figures 3A, 3B, 3C, 3D, 3E, 3F, 3G:
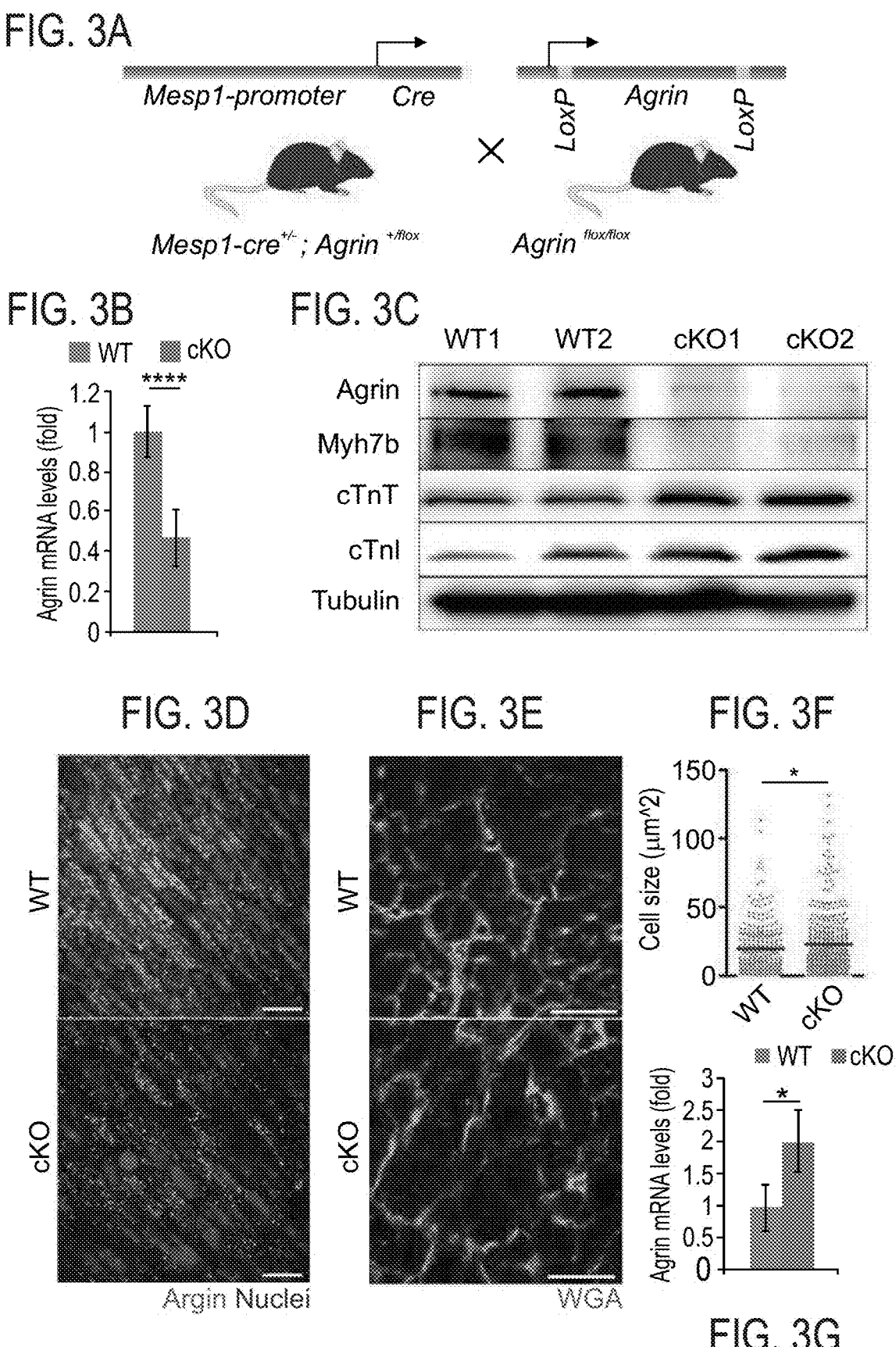
Figures 3H, 3I:
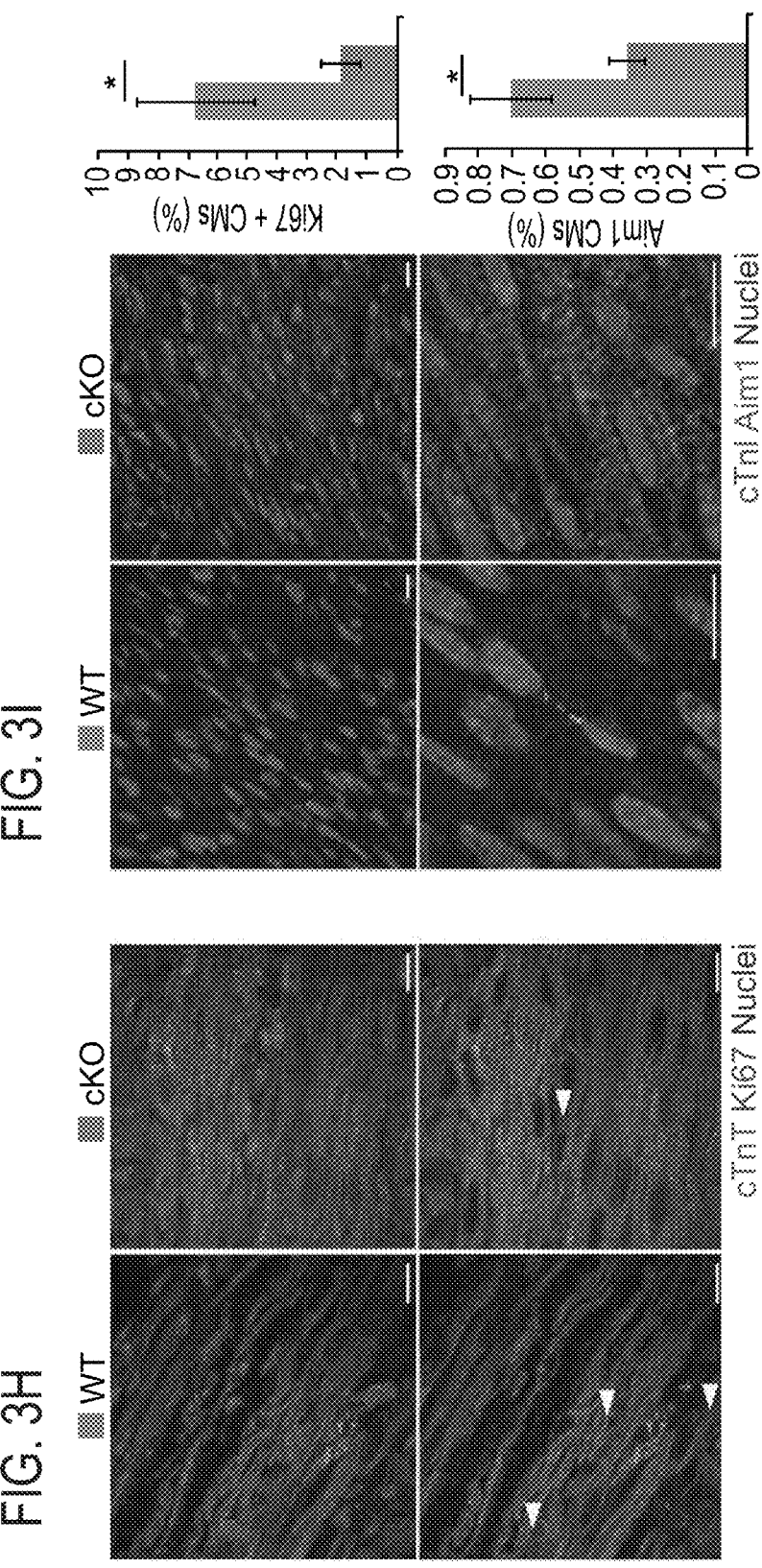
Figures 3J, 3K, 3L, 3M, 3N, 3O:
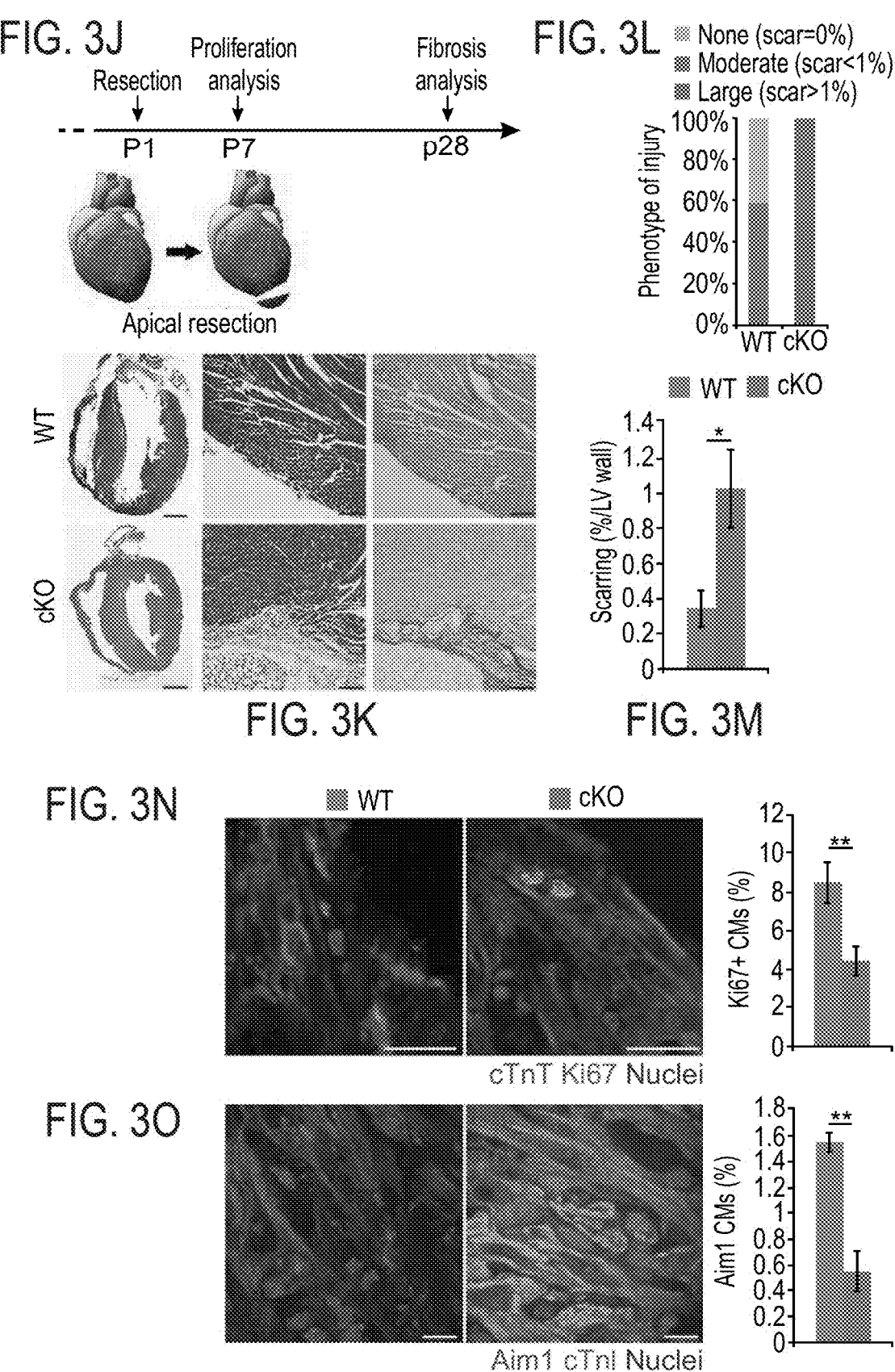

FIGS. 3A-3O show that Agrin is required for P1 cardiac regeneration following surgical resection. (FIG. 3A) A schematic diagram depicting the generation of cardiac restricted Agrin knockout (Agrin-cKO) mice. (FIG. 3B) Western Blot analysis of Agrin and sarcomeric protein levels in P1 WT and Agrin-cKO heart lysates. (FIG. 3C) qPCR of Agrin in P1 WT and Agrin-cKO heart lysates. (FIG. 3D) Immunofluorescence analysis of Agrin in P1 WT and Agrin-cKO. (FIG. 3E) Immunofluorescence analysis of WGA membrane staining in P1 WT and Agrin-cKO depicting changes in cell size (FIG. 3F). (FIG. 3G) qPCR analysis of a pathological hypertrophic marker (i.e., Acta1) in P1 WT and Agrin-cKO heart lysates. In vivo evaluation of P1 CM cell-cycle re-entry (Ki67; FIG. 3H) and cytokinesis (Aim1; FIG. 3I) by immunofluorescence analysis in WT and Agrin-cKO left ventricle heart sections. (FIG. 3J) Scheme of P1 resection experiment. (FIG. 3K) Histological sections of P1 WT and Agrin-cKO stained with Masson's trichrome and Sirius red. (FIGS. 3L-3M) Scar quantification based on Masson's trichrome staining of heart sections of 4 weeks post resection WT and Agrin-cKO. (FIGS. 3N,O) In vivo evaluation of CM cell-cycle re-entry by immunofluorescence analysis of Ki67 (FIG. 3N) or Aim1 (FIG. 3O) in sections taken from resected WT and Agrin-cKO hearts.

FIGS. 4A-4I show that Agrin inoculation is sufficient for cardiac regeneration following MI. (FIG. 4A) A schematic diagram depicting the LAD ligation experiment in both juvenile and adult. (FIG. 4B-4E) In vivo evaluation of CM cell-cycle re-entry by immunofluorescence analysis of Ki67 (FIG. 4 B, D) or Aim1 (FIG. 4C, E) in heart sections 7 days post MI in juvenile (FIG. 4B, C) and adult (FIG. 4D, E) mice. (FIG. 4F, G) Serial echocardiographic measurements of ejection fraction (EF), fractional shortening (FS) and wall thickness of uninjured and injured PBS and Agrin treated juvenile (FIG. 4F) and adult (FIG. 4G) mice following MI, according to the schema in FIG. 4A. (FIG. 4H, 4I) Scar quantification based on Masson's trichrome staining of heart sections of PBS and Agrin treated juvenile (FIG. 4H) and adult (FIG. 4I) mice.

FIGS. 5A-5J show that Agrin promotes CM proliferation through Dag1 and ERK activation. (FIG. 5A) qPCR Of Dag1 gene from P1 and P7 heart lysates. (FIG. 5B) Western blot analysis Dag1 from P1 and P7 heart lysates. (FIG. 5C) qPCR analysis of 6 cell populations (FB, non-FB, CM, non-CM, EC, non-EC) for Dag1. (FIG. 5D) Western blot analysis of phospho-ERK (pERK) and general-ERK (gERK) in P7 control and Agrin treated cultures. (FIG. 5E) CM ERK activation analysis by immunofluorescence staining for pERK of P7 control and Agrin treated cultures. (FIG. 5F) Western blot analysis of pERK and gERK in P7 control, Dag1 inhibition, Agrin and Agrin with Dag1 inhibition treated cultures. (FIG. 5G-5H) CM cell cycle activity analysis by immunofluorescence staining following Agrin treatment with either MEK inhibition (FIG. 5G) or Dag1 inhibition (FIG. 5H). (FIG. 5I) Immunofluorescence evaluation of P7 CM cell cycle activity (Ki67) in response to Agrin administration in WT and mdx in vitro. (FIG. 5J) Serial immunofluorescence counting of tomato labeled CMs treated with various compounds shown to inhibit $Na^+/K^+$ pumps.

FIGS. 6A-6D show that in vitro Agrin administration promotes human iPSC-derived CMs proliferation. (FIG. 6A) Serial Immunofluorescence evaluation of iPSC-CM cell cycle activity (Ki67) in response to Agrin administration. (FIG. 6B) Day 4 Immunofluorescence analysis of cell cycle activity. (FIGS. 6C-6D) Immunofluorescence evaluation of iPSC-CM cell cycle activity either by Ph3 (FIG. 6C) or Aim1 (FIG. 6D) in response to human-Agrin administration in a dose dependent manner.

Figure 7A:
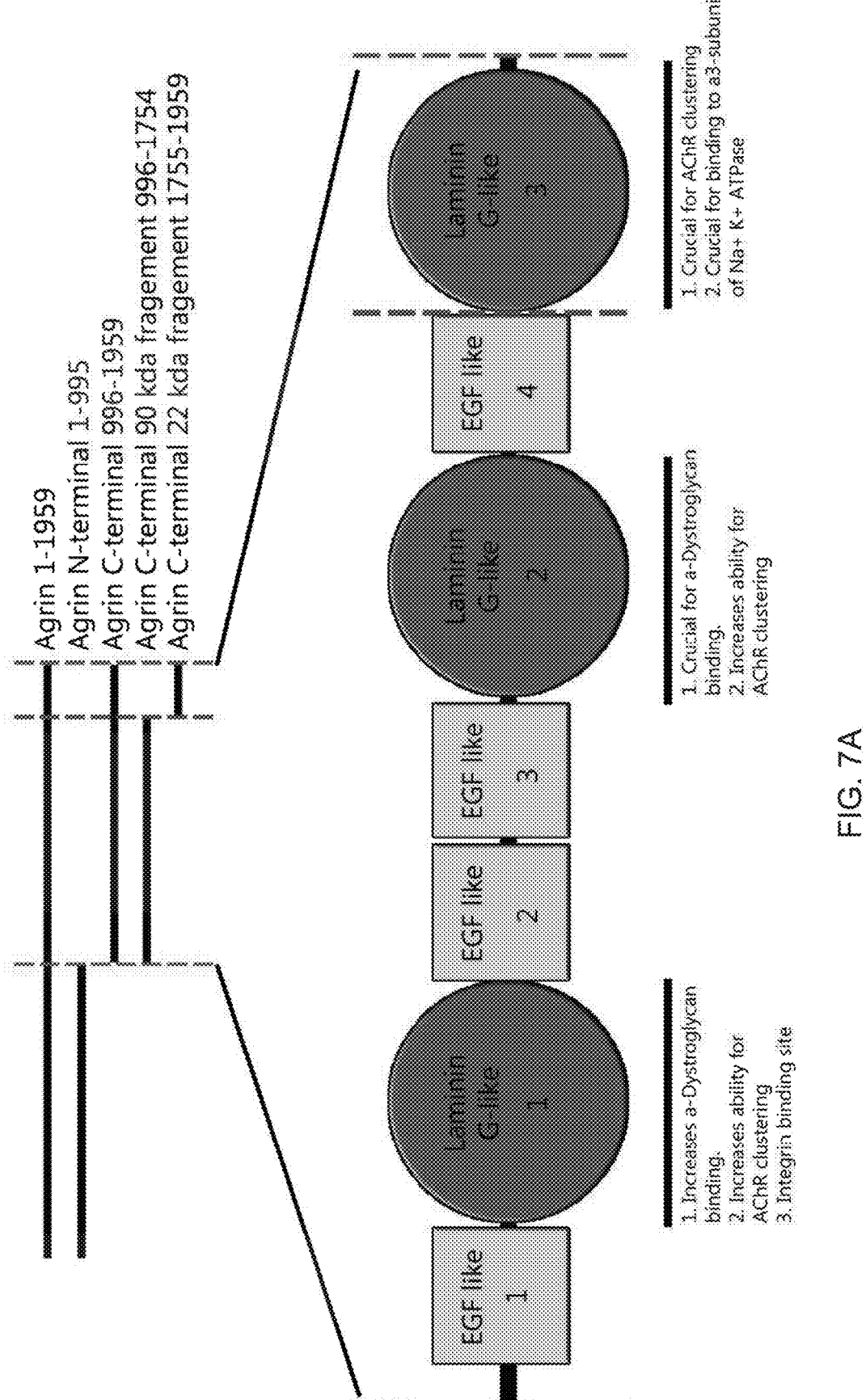

FIGS. 7A-7B illustrate the protein structure of Agrin (based on Singhal and Martin 2011 Develop. Neurol. 982-1005) and its alignment in human, mouse and rat (SEQ ID NOs: 38, 9, 6, respectively).

FIGS. 8A-8H show agrin transcription effects in myoinfarcted (MI) hearts. RNA sequencing was performed on MI hearts treated with Agrin/PBS, to evaluate Agrin transcriptional effects in the infarcted adult heart. (FIG. 8A) Schematic diagram depicting the experimental design: adult hearts were subjected to LAD ligation, and subjected to either PBS or Agrin injection. 3 days post treatment, hearts were collected from Agrin. PBS and sham operated mice, and RNA was purified and subjected to RNA-seq. (FIG. 8B) Volcano plot of differentially expressed genes in infarcted Agrin vs. PBS (MI) treated hearts. Fold expression change against p value is plotted. Significant increased or decreased genes are indicated in red or blue, respectively. Filled circles indicate relevant genes that are known to participate in important pathways in heart regeneration and immune modulation. (FIG. 8C) Heat map depicting differentially expressed genes affected by Agrin. RNA-seq gene expression data was compared to an MI differentially expressed genes data base1. Differentially expressed genes that showed similar pattern in the present MI setting (PBS vs. sham) and in the preexisting database were compared. These genes are referred to as "MI signature". The relative expression of these genes in the data base MI (Ounzain, Left panel), the present MI (Experimental MI, middle panel) and MI treated with Agrin (Agrin MI vs. PBS MI, Experimental MI+Agrin, right panel). (FIGS. 8D-8E) The genes shown in FIG. 8C were analyzed using ingenuity pathway analysis software. Prominent significantly enriched terms are shown for (FIG. 8D) canonical pathways and (8E) upstream regulators. (FIGS. 8F-8G) Heat maps depicting the relative expression of relevant genes in prominent (FIG. 8F) canonical pathways and (FIG. 8G) upstream regulators. (FIG. 8H) Real time validation of several genes shown in (FIG. 8F) and (FIG. 8G).

DESCRIPTION OF SPECIFIC EMBODIMENTS OF THE INVENTION

The present invention, in some embodiments thereof, relates to methods of inducing proliferation of cardiomyocytes and methods of treating heart diseases.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Heart disease, including myocardial infarction (MI), is the leading cause of death in the world. The severity of heart disease is due to the post-mitotic nature of human adult cardiac muscle cells—the cardiomyocytes (CMs) {Bergmann, 2009 #9; Senyo, 2013 #86} and their limited capacity to replenish damaged tissue {Poss, 2007 #30; Ausoni, 2009 #17}. In contrast, the neonatal murine CM turnover is sufficient to repair damaged myocardium following injury; however this ability is greatly diminished during the first week after birth.

Whilst searching for novel treatment modalities that can boost the proliferative nature of juvenile/adult CMs, the present inventors have employed a novel method for identifying murine cardiac ECM compositions that promote CM proliferation and identified Agrin, a proteoglycan expressed by cardiac endothelial cells at birth but its levels decline after 7 days. Treatment with recombinant Agrin induces CM cell cycle reentry and division in-vitro. At birth, Agrin conditional knockout (cKO) CMs display mature and more differentiated phenotype accompanied by reduced proliferation and impaired cardiac regeneration. In contrast, Agrin administration following myocardial infarction (MI) induces CM proliferation that leads to reduced scarring and overall improved cardiac function in both neonatal and adult mice. Mechanistically, the present inventors suggest that Agrin functions via modulation of the Dystroglycan complex by blocking sarcomerogenesis and not through its canonical MuSK related signaling. These findings thus render any agent, which inhibits the dystroglycan complex in CMs a potential therapy for heart diseases. Transcriptional analysis suggests that Agrin promotes heart regeneration not only through cardiomyocyte proliferation by also through immune modulation, which might change cardiomyocyte survival thereby reducing infarct and scar size.

Thus, according to an aspect of the invention there is provided a method of inducing proliferation of CMs, the method comprising contacting the cardiomyocytes with an agent, which inhibits the Dystroglycan complex on the CMs, thereby inducing proliferation of CMs.

According to another aspect of the invention there is provided a method of inducing proliferation of cardiomyocytes, the method comprising contacting the cardiomyocytes with an effective amount of an agrin peptide which induces proliferation of the cardiomyocytes.

As used herein "a cardiomyocyte" or "cardiomyocytes" (abbreviated as, CM, CMs), also known as myocardiocytes or cardiac myocytes, are the muscle cells (myocytes) that make up the cardiac muscle. The term refers to cardiomyocytes of any species including mammalian, e.g., human at any stage of development. According to a specific embodiment, the cardiomyocyte is a neonatal CM (e.g., for human up 6 months after birth). According to a specific embodiment, the cardiomyocyte is an adult cardiomyocyte (e.g., for human at least 16-18 years after birth).

Thus, according to a specific embodiment, the cardiomyocytes are of a subject having a heart disease.

According to a specific embodiment, the cardiomyocytes are of a donor healthy subject.

According to a specific embodiment, the cardiomyocytes may be naturally occurring.

According to a specific embodiment, the CMs have been ex-vivo differentiated into cardiomyocytes (e.g., from pluripotent stem cells e.g., embryonic stem cells (hESCs) and induced pluripotent stem cells (iPSCs)). Methods of differentiating stem cells into CMs are well known in the art. For example, an iPSC can be co-cultured with visceral endoderm-like cells (see, e.g., Mummery et al. (2003) Circulation 107:2733). An iPS cell can also be induced to undergo cardiomyogenesis without co-culture with a feeder cell or other cell. For example, as described in U.S. Pat. No. 7,297,539. The CMs may be fully differentiated when contacted with the agent (e.g., Agrin). According to another embodiment, the cells are committed to the cardiac lineage and the agent (e.g., Agrin) is added to the culture during or following the differentiation process.

According to a specific embodiment, the cardiomyocytes are human CMs.

According to a specific embodiment, the CMs are a cell-line.

According to a specific embodiment, the CMs are primary CMs.

As used herein the term "inducing proliferation" refers to an increase in CM proliferation which is statistically significant (as compared to untreated cells of the same origin and developmental stage) and is a result of contacting the cardiomyocytes with the agent e.g., Agrin.

As mentioned, the cells are contacted with an agent, which inhibits the dystroglycan complex on CMs. Our data suggest that Agrin interacts with the dystroglycan complex since an antibody against this molecule inhibits Agrin-induced effects on CM proliferation and ERK activation. Alternatively or additionally, the agent modulates the structural activity of dystroglycan as a bridging molecule between the CM cytoskeleton and the ECM, thus allowing the CM to proliferate.

As mentioned, the agent described herein is capable of inducing immune modulation (see FIGS. 8A-8H) by which increasing cardiomyocyte survival, anti inflammatory and/or anti fibrotic effects.

As used herein "immune modulation" refers to induced changes in gene expression (e.g., RNA as determined by RNA-Seq) of canonical pathway genes—and/or upstream regulators (see FIGS. 8A-8H which are hereby incorporated).

As used herein, the term "agent" refers to a substance which can be of a biological nature e.g., proteinaceous substance e.g., peptide (e.g., further described hereinbelow) or an antibody, nucleic acid substance e.g., a polynucleotide or an oligonucleotide, or a chemical nature e.g., small molecule.

As used herein the term "polynucleotide" refers to a single or double stranded nucleic acid sequence which is isolated and provided in the form of an RNA sequence, a complementary polynucleotide sequence (cDNA), a genomic polynucleotide sequence and/or a composite polynucleotide sequences (e.g., a combination of the above).

The term "isolated" refers to at least partially separated from the natural environment e.g., from a recombinant host cell.

Other agents which can be used to inhibit the dystroglycan complex can be identified by contacting the agent with cardiomyocytes that express the dystroglycan complex and identifying an agent which binds the dystroglycan complex and optionally induces Erk activation and ultimately CM proliferation or inhibit sarcomerogenesis. Protein binding can be assayed using numerous assays known in the art e.g., ELISA assay, co-immunoprecipitation, membrane binding. FRET, surface Plasmon resonance and the like.

Alternatively or additionally, and as mentioned, the cells are contacted with an "Agrin peptide".

As used herein the term "Agrin" refers to the protein product of the AGRN gene. The term is meant to include polynucleotide sequences encoding Agrin or expression products as RNA or a protein.

An "Agrin peptide" refers to an Agrin peptide which is shorter than the full-length agrin (e.g., in the case of human Agrin shorter than the 2068/2045 amino acids which make up the full length human agrins) and is capable of inducing proliferation of cardiomyocytes. According to a specific embodiment the Agrin peptide is provided in a soluble form.

According to a specific embodiment the agrin peptide is from human Agrin NP_001292204 (SEQ ID NO: 4) or NP_940978 (SEQ ID NO: 5) or Uniprot 000468 SEQ ID NO: 38.

According to a specific embodiment, the Agrin peptide is of a human ortholog e.g., NP_786930 (SEQ ID NO: 6).

It will be appreciated that the present teachings contemplate the treatment of one species (e.g., human) with an Agrin peptide of a second species (e.g., rat) as long as they exhibit the desired activity (i.e., induced CM proliferation) on the treated subject/cells.

According to a specific embodiment, the Agrin peptide comprises a Laminin G-like 2 (G2) domain and optionally a Laminin G-like 1 (G1) domain.

Thus according to a specific embodiment, the Agrin peptide comprises the G2 domain as set forth in SEQ ID NO: 8 or G1 and G2 as set forth in SEQ ID NO: 7.

Accordingly there is provided an isolated peptide comprising Laminin G-like 2 (G2) domain the peptide being no more than 200 amino acids in length.

According to a specific embodiment the peptide is as set forth in SEQ ID NO: 8.

Without being hound by theory, it is suggested that such a configuration which comprises at least the Laminin G-like 2 (G2) and possibly G1 and/or G3 domains is required for alpha-dystroglycan/DAG1 binding.

According to a specific embodiment, such an Agrin peptide promotes sarcomere disassembly and cardiomyocyte proliferation leading to heart regeneration.

According to a specific embodiment, the Agrin peptide does not exert its function via binding to the MuSK receptor. Indeed no MuSK receptor is expressed in the heart as evident from RNA-seg profiles [41].

According to a specific embodiment, the Agrin peptide is 50-500 amino acids long. According to a specific embodiment, the Agrin peptide is 100-400 amino acids long. According to a specific embodiment, the Agrin peptide is 100-300 amino acids long, According to a specific embodiment, the Agrin peptide is 150-200 amino acids long. According to a specific embodiment, the Agrin peptide is 100-200 amino acids long.

According to a specific embodiment, the Agrin peptide is 80-150 kDa. According to a specific embodiment, the Agrin peptide is 80-120 kDa. According to a specific embodiment, the Agrin peptide is 80-110 kDa. According to a specific embodiment, the Agrin peptide is 90-110 kDa.

Agrin peptides are commercially available from R&D systems e.g., 6624-AG, 550-AG or 550-AG/CF.

According to a specific embodiment, the Agrin peptide binds the dystroglycan complex via the Laminin G1-G2 domains [42]. The inventors suggest that Agrin inhibits its activity thereby leading to Erk activation and optionally inhibits sarcromerogenesis.

Methods of determining Erk (also known as extracellular-signal-regulated kinases (ERKs) or classical MAP kinases) activation are well known in the art and include, but are not limited to, in vitro kinase assays and the use of anti-phosphorylated MAPK antibodies.

According to a specific embodiment, the Agrin is not a part of a fusion polypeptide where the Agrin is serving as a targeting moiety for the delivery of a therapeutically effective peptide.

According to another specific embodiment, the Agrin is a part of a fusion polypeptide where the Agrin is serving both as a targeting moiety and an effector moiety (i.e., for inducing CM proliferation).

According to a specific embodiment, the Agrin is provided in a soluble form. Accordingly, the Agrin is not part or attached to an extracellular matrix composition.

Methods of determining CM proliferation are well known in the art, and include, but are not limited to, manual cell counting, MTT assay and a thymidine incorporation assay. According to some embodiments both ascertaining the nature of the cells as well as determining their proliferation are done.

For example, in some embodiments, the presence of proliferative cardiomyocytes is validated by confirming expression of at least one cardiomyocyte-specific marker produced by the cell. For example, the cardiomyocytes express cardiac transcription factors, sarcomere proteins, and gap junction proteins. Suitable cardiomyocyte-specific proteins include, but are not limited to, cardiac troponin 1, cardiac troponin-C, tropomyosin, caveolin-3, GATA-4, myosin heavy chain, myosin light chain-2a, myosin light chain-2v, ryanodine receptor, and atrial natriuretic factor.

As another example, in some embodiments, cardiomyocytes are ascertained by detecting responsiveness to pharmacological agents such as beta-adrenergic agonists (e.g., isoprenaline), adrenergic beta-antagonists (e.g., esmolol), cholinergic agonists (e.g., carbochol), and the like.

Alternatively or additionally, validating the nature of the CMs is done by detecting electrical activity of the cells. Electrical activity can be measured by various methods, including extracellular recording, intracellular recording (e.g., patch clamping), and use of voltage-sensitive dyes. Such methods are well known to those skilled in the art.

The term "peptide" as used herein encompasses native peptides (either degradation products, synthetically synthesized peptides or recombinant peptides) and peptidomimetics (typically, synthetically synthesized peptides), as well as peptoids and semipeptoids which are peptide analogs, which may have, for example, modifications rendering the peptides more stable while in a body or more capable of penetrating into cells. Such modifications include, but are not limited to N terminus modification. C terminus modification, peptide bond modification, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein. Further details in this respect are provided hereinunder. According to a specific embodiment, the peptide (or polypeptide) is a recombinant product (i.e., of recombinant DNA technology). According to a specific embodiment, the agrin is above 95% pure (e.g., no other active ingredient proteins are present in the formulation).

Peptide bonds (—CO—NH—) within the peptide may be substituted, for example, by N-methylated amide bonds (—N(CH3)-CO—), ester bonds (—C(=O)—O—), ketom-ethylene bonds (—CO—CH2-), sulfinylmethylene bonds (—S(=O)—CH2-), α-aza bonds (—NH—N(R)—CO—), wherein R is any alkyl (e.g., methyl), amine bonds (—CH2-

NH—), sulfide bonds (—CH2-S—), ethylene bonds (—CH2-CH2-), hydroxyethylene bonds (—CH(OH)—CH2-), thioamide bonds (—CS—NH—), olefinic double bonds (—CH═CH—), fluorinated olefinic double bonds (—CF═CH—), retro amide bonds (—NH—CO—), peptide derivatives (—N(R)—CH2-CO—), wherein R is the "normal" side chain, naturally present on the carbon atom.

These modifications can occur at any of the bonds along the peptide chain and even at several (2-3) bonds at the same time.

Natural aromatic amino acids, Trp, Tyr and Phe, may be substituted by non-natural aromatic amino acids such as 1,2,3,4-tetrahydroisoquinoline-3-carboxylic acid (Tic), naphthylalanine, ring-methylated derivatives of Phe, halogenated derivatives of Phe or O-methyl-Tyr.

The peptides of some embodiments of the invention may also include one or more modified amino acids or one or more non-amino acid monomers (e.g. fatty acids, complex carbohydrates etc).

The term "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids.

Tables 1 and 2 below list naturally occurring amino acids (Table 1), and non-conventional or modified amino acids (e.g., synthetic, Table 2) which can be used with some embodiments of the invention.

TABLE 1

| Amino Acid | Three-Letter Abbreviation | One-letter Symbol |
| --- | --- | --- |
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic Acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Any amino acid as above | Xaa | X |

TABLE 2

| Non-conventional amino acid | Code | Non-conventional amino acid | Code |
| --- | --- | --- | --- |
| ornithine | Orn | hydroxyproline | Hyp |
| α-aminobutyric acid | Abu | aminonorbornyl-carboxylate | Norb |
| D-alanine | Dala | aminocyclopropane-carboxylate | Cpro |
| D-arginine | Darg | N-(3-guanidinopropyl)glycine | Narg |
| D-asparagine | Dasn | N-(carbamylmethyl)glycine | Nasn |
| D-aspartic acid | Dasp | N-(carboxymethyl)glycine | Nasp |
| D-cysteine | Dcys | N-(thiomethyl)glycine | Ncys |
| D-glutamine | Dgln | N-(2-carbamylethyl)glycine | Ngln |
| D-glutamic acid | Dgln | N-(2-carboxyethyl)glycine | Ngln |
| D-histidine | Dhis | N-(imidazolylethyl)glycine | Nhis |
| D-isoleucine | Dile | N-(1-methylpropyl)glycine | Nile |
| D-leucine | Dleu | N-(2-methylpropyl)glycine | Nleu |
| D-lysine | Dlys | N-(4-aminobutyl)glycine | Nlys |
| D-methionine | Dmet | N-(2-methylthioethyl)glycine | Nmet |
| D-ornithine | Dorn | N-(3-aminopropyl)glycine | Norn |
| D-phenylalanine | Dphe | N-benzylglycine | Nphe |
| D-proline | Dpro | N-(hydroxymethyl)glycine | Nser |
| D-serine | Dser | N-(1-hydroxyethyl)glycine | Nthr |
| D-threonine | Dthr | N-(3-indolylethyl) glycine | Nhtrp |
| D-tryptophan | Dtrp | N-(p-hydroxyphenyl)glycine | Ntyr |
| D-tyrosine | Dtyr | N-(1-methylethyl)glycine | Nval |
| D-valine | Dval | N-methylglycine | Nmgly |
| D-N-methylalanine | Dnmala | L-N-methylalanine | Nmala |
| D-N-methylarginine | Dnmarg | L-N-methylarginine | Nmarg |
| D-N-methylasparagine | Dnmasn | L-N-methylasparagine | Nmasn |
| D-N-methylasparatate | Dnmasp | L-N-methylaspartic acid | Nmasp |
| D.N-methylcysteine | Dnmcys | L-N-methylcysteine | Nmcys |
| D-N-methylglutamine | Dnmgln | L-N-methylglutamine | Nmgln |
| D-N-methylglutamate | Dnmglu | L-N-methylglutamic acid | Nmglu |
| D-N-methylhistidine | Dnmhis | L-N-methylhistidine | Nmhis |
| D-N-methylisoleucine | Dnmile | L-N-methylisolleucine | Nmile |
| D-N-methylleucine | Dnmleu | L-N-methylleucine | Nmleu |
| D-X-methyllysine | Dnmlys | L-N-methyllysine | Nmlys |
| D-N-methylmethionine | Dnmmet | L-N-methylmethionine | Nmmet |
| D-N-methylornithine | Dnmorn | L-A-methylornithine | Nmorn |
| D-N-methylphenylalanine | Dnmphe | L-N-methylphenylalanine | Nmphe |
| D-N-methylproline | Dnmpro | L-N-methylproline | Nmpro |
| D-N-methylserine | Dnmser | L-X-methylserine | Nmser |
| D-N-methylthreonine | Dnmthr | L-N-methylthreonine | Nmthr |
| D-N-methyltryptophan | Dnmtrp | L-N-methyltryptophan | Nmtrp |

TABLE 2-continued

| Non-conventional amino acid | Code | Non-conventional amino acid | Code |
|---|---|---|---|
| D-N-methyltyrosine | Dnmtyr | L-N-methyltyrosine | Nmtyr |
| D-N-methylvaline | Dnmval | L-N-methylvaline | Nmval |
| L-norleucine | Nle | L-N-methylnorleucine | Nmnle |
| L-norvaline | Nva | L-N-methylnorvaline | Nmnva |
| L-ethylglycine | Etg | L-N-methyl-ethylglycine | Nmetg |
| L-t-butylglycine | Tbug | L-N-methyl-t-butylglycine | Nmtbug |
| L-homophenylalanine | Hphe | L-N-methyl-homophenylalanine | Nmhphe |
| α-naphthylalanine | Anap | N-methyl-α-naphthylalanine | Nmanap |
| penicillamine | Pen | N-methylpenicillamine | Nmpen |
| γ-aminobutyric acid | Gabu | N-methyl-γ-aminobutyrate | Nmgabu |
| cyclohexylalanine | Chexa | N-methyl-cyclohexylalanine | Nmchexa |
| cyclopentylalanine | Cpen | N-methyl-cyclopentylalanine | Nmcpen |
| α-amino-α-methylbutyrate | Aabu | N-methyl-α-amino-α-methylbutyrate | Nmaabu |
| α-aminoisobutyric acid | Aib | N-methyl-α-aminoisobutyrate | Nmaib |
| D-α-methylarginine | Dmarg | L-α-methylarginine | Marg |
| D-α-methylasparagine | Dmasn | L-α-methylasparagine | Masn |
| D-α-methylaspartate | Dmasp | L-α-methylaspartate | Masp |
| D-α-methylcysteine | Dmcys | L-α-methylcysteine | Mcys |
| D-α-methylglutamine | Dmgln | L-α-methylglutamine | Mgln |
| D-α-methyl glutamic acid | Dmglu | L-α-methylglutamate | Mglu |
| D-α-methylhistidine | Dmhis | L-α-methylhistidine | Mhis |
| D-α-methylisoleucine | Dmile | L-α-methylisoleucine | Mile |
| D-α-methylleucine | Dmleu | L-α-methylleucine | Mleu |
| D-α-methyllysine | Dmlys | L-α-methyllysine | Mlys |
| D-α-methylmethionine | Dmmet | L-α-methylmethionine | Mmet |
| D-α-methylornithine | Dmorn | L-α-methylornithine | Morn |
| D-α-methylphenylalanine | Dmphe | L-α-methylphenylalanine | Mphe |
| D-α-methylproline | Dmpro | L-α-methylproline | Mpro |
| D-α-methylserine | Dmser | L-α-methylserine | Mser |
| D-α-methylthreonine | Dmthr | L-α-methylthreonine | Mthr |
| D-α-methyltryptophan | Dmtrp | L-α-methyltryptophan | Mtrp |
| D-α-methyltyrosine | Dmtyr | L-α-methyltyrosine | Mtyr |
| D-α-methylvaline | Dmval | L-α-methylvaline | Mval |
| N-cyclobutylglycine | Nebut | L-α-methylnorvaline | Mnva |
| N-cycloheptylglycine | Nchep | L-α-methylethylglycine | Metg |
| N-cyclohexylglycine | Nchex | L-α-methyl-t-butylglycine | Mtbug |
| N-cyclodecylglycine | Ncdec | L-α-methyl-homophenylalanine | Mhphe |
| N-cyclododecylglycine | Ncdod | α-methyl-α-naphthylalanine | Manap |
| N-cyclooctylglycine | Ncoct | α-methylpenicillamine | Mpen |
| N-cyclopropylglycine | Ncpro | α-methyl-γ-aminobutyrate | Mgabu |
| N-cycloundecylglycine | Neund | α-methyl-cyclohexylalanine | Mchexa |
| N-(2-aminoethyl)glycine | Naeg | α-methyl-cyclopentylalanine | Mcpen |
| N-(2,2-diphenylethyl)glycine | Nbhm | N-(N-(2,2-diphenylethyl) carbamylmethvl-glycine | Nnbhm |
| N-(3,3-diphenylpropyl)glycine | Nbhe | N-(N-(3,3-diphenylpropyl) carbamylmethvl-glycine | Nnbhe |
| 1-carboxy-1-(2,2-diphenyl ethylamino)cyclopropane | Nmbe | 1,2,3,4-tetrahydroisoquinoline-3-carboxylic acid | Tic |
| phosphoserine | pSer | phosphothreonine | pThr |
| phosphotyrosine | pTyr | O-methyl-tyrosine | |
| 2-aminoadipic acid | | hydroxylysine | |

The peptides of some embodiments of the invention are preferably utilized in a linear form, although it will be appreciated that in cases where cyclization does not severely interfere with peptide characteristics, cyclic forms of the peptide can also be utilized.

Since the present peptides are preferably utilized in therapeutics or diagnostics which require the peptides to be in soluble form, the peptides of some embodiments of the invention preferably include one or more non-natural or natural polar amino acids, including but not limited to serine and threonine which are capable of increasing peptide solubility due to their hydroxyl-containing side chain.

The peptides of some embodiments of the invention are preferably utilized in a linear form, although it will be appreciated that in cases where cyclization does not severely interfere with peptide characteristics, cyclic forms of the peptide can also be utilized.

It will be appreciated that the proteinaceous agents of some embodiments of the invention, can also utilize functional homologues which exhibit the desired activity (i.e., induced proliferation of CMs). Such homologues can be, for example, at least, 60%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identical to the human sequence e.g., human Agrin e.g., SEQ ID NO: 4, 5, 7 or 8, as determined using the BestFit software of the Wisconsin sequence analysis package, utilizing the Smith and Waterman algorithm, where gap weight equals 50, length weight equals 3, average match equals 10 and average mismatch equals −9.

The peptides of some embodiments of the invention may be synthesized by any techniques that are known to those skilled in the art of peptide synthesis. For solid phase peptide synthesis, a summary of the many techniques may be found in J. M. Stewart and J. D. Young, Solid Phase Peptide Synthesis, W. H. Freeman Co. (San Francisco), 1963 and J. Meienhofer, Hormonal Proteins and Peptides, vol. 2, p. 46. Academic Press (New York), 1973. For classical solution synthesis see G. Schroder and K. Lupke. The Peptides, vol. 1, Academic Press (New York), 1965.

In general, these methods comprise the sequential addition of one or more amino acids or suitably protected amino acids to a growing peptide chain. Normally, either the amino or carboxyl group of the first amino acid is protected by a suitable protecting group. The protected or derivatized amino acid can then either be attached to an inert solid support or utilized in solution by adding the next amino acid in the sequence having the complimentary (amino or carboxyl) group suitably protected, under conditions suitable for forming the amide linkage. The protecting group is then removed from this newly added amino acid residue and the next amino acid (suitably protected) is then added, and so forth. After all the desired amino acids have been linked in the proper sequence, any remaining protecting groups (and any solid support) are removed sequentially or concurrently, to afford the final peptide compound.

Alternatively, the peptides am produced using recombinant DNA technology.

A variety of prokaryotic or eukaryotic cells can be used as host-expression systems to express the polypeptides/peptides of some embodiments of the invention. These include, but are not limited to, microorganisms, such as bacteria transformed with a recombinant bacteriophage DNA, plasmid DNA or cosmid DNA expression vector containing the coding sequence; yeast transformed with recombinant yeast expression vectors containing the coding sequence; plant cell systems infected with recombinant virus expression vectors (e.g., cauliflower mosaic virus, CaMV; tobacco mosaic virus, TMV) or transformed with recombinant plasmid expression vectors, such as Ti plasmid, containing the coding sequence. Mammalian expression systems can also be used to express the polypeptides of some embodiments of the invention.

For the sake of simplicity agrin and the agent are collectively referred to herein as "an agent" or "agents" although it should be appreciated that each possibility of an agent represents a separate embodiment of the present invention.

According to a specific embodiment, the proteinaceous agent can be attached (or conjugated) to non-proteinaceous moieties which increase their bioavailability and half-life in the circulation.

The phrase "non-proteinaceous moiety" as used herein refers to a molecule not including peptide bonded amino acids that is attached to the above-described proteinaceous agents. Exemplary non-proteinaceous and preferably non-toxic moieties which may be used according to the present teachings include, but are not limited to, polyethylene glycol (PEG), Polyvinyl pyrrolidone (PVP), poly(styrene comaleic anhydride) (SMA), and divinyl ether and maleic anhydride copolymer (DIVEMA).

Such a molecule is highly stable (resistant to in-vivo proteolytic activity probably due to steric hindrance conferred by the non-proteinaceous moiety) and may be produced using common solid phase synthesis methods which are inexpensive and highly efficient, as further described hereinbelow. However, it will be appreciated that recombinant techniques may still be used, whereby the recombinant peptide product is subjected to in-vitro modification (e.g., PEGylation).

Thus, such non-proteinaceous non-toxic moieties may also be attached to the above mentioned agents to promote stability and possibly solubility of the molecules.

Bioconjugation of such a non-proteinaceous moiety (such as PEGylation) can confer the proteins amino acid sequence with stability (e.g., against protease activities) and/or solubility (e.g., within a biological fluid such as blood, digestive fluid) while preserving its biological activity and prolonging its half-life.

Bioconjugation is advantageous particularly in cases of therapeutic proteins which exhibit short half-life and rapid clearance from the blood. The increased half-lives of bioconjugated proteins in the plasma results from increased size of protein conjugates (which limits their glomerular filtration) and decreased proteolysis due to polymer steric hindrance. Generally, the more polymer chains attached per peptide, the greater the extension of half-life. However, measures are taken not to reduce the specific activity of the protein of the present invention (e.g., CM proliferation).

Bioconjugation of the proteinaceous agent with PEG (i.e., PEGylation) can be effected using PEG derivatives such as N-hydroxysuccinimide (NHS) esters of PEG carboxylic acids, monomethoxyPEG$_2$-NHS, succinimidyl ester of carboxymethylated PEG (SCM-PEG), benzotriazole carbonate derivatives of PEG, glycidyl ethers of PEG, PEG p-nitrophenyl carbonates (PEG-NPC, such as methoxy PEG-NPC), PEG aldehydes. PEG-orthopyridyl-disulfide, carbonyldimidazol-activated PEGs, PEG-thiol, PEG-maleimide. Such PEG derivatives are commercially available at various molecular weights [See, e.g., Catalog, Polyethylene Glycol and Derivatives, 2000 (Shearwater Polymers, Inc., Huntsville, Ala.)]. If desired, many of the above derivatives are available in a monofunctional monomethoxyPEG (mPEG) form. In general, the PEG added to the anti HER3 antibody amino acid sequence of the present invention should range from a molecular weight (MW) of several hundred Daltons to about 100 kDa (e.g., between 3-30 kDa). Larger MW PEG may be used, but may result in some loss of yield of PEGylated peptides. The purity of larger PEG molecules should be also watched, as it may be difficult to obtain larger MW PEG of purity as high as that obtainable for lower MW PEG. It is preferable to use PEG of at least 85% purity, and more preferably of at least 90% purity, 95% purity, or higher. PEGylation of molecules is further discussed in, e.g., Hermanson, Bioconjugate Techniques, Academic Press San Diego, Calif. (1996), at Chapter 15 and in Zalipsky et al., "Succinimidyl Carbonates of Polyethylene Glycol," in Dunn and Ottenbrite, eds., Polymeric Drugs and Drug Delivery Systems, American Chemical Society, Washington, D.C. (1991).

According to a specific embodiment, the methods described herein for inducing CM proliferation are effected in vivo.

According to a specific embodiment, the methods described herein for inducing CM proliferation are effected in vitro.

According to a specific embodiment, the methods described herein for inducing CM proliferation are effected ex vivo.

According to a specific embodiment the cardiomyocytes are comprised in a tissue (a vascularized tissue).

The ability to induce CM proliferation renders the present teachings particularly suitable for the treatment of heart diseases where there is damage to the cardiac tissue or there is a risk for such damage.

Thus, according to an aspect of the invention there is provided a use of a therapeutically effective amount of an Agrin peptide which induces proliferation of cardiomyocytes in the manufacture of a medicament for treating a heart disease.

Alternatively, according to an aspect of the invention there is provided a use of a therapeutically effective amount of an Agrin peptide which induces proliferation of cardiomyocytes in the manufacture of a medicament for treating a heart disease.

Alternatively, according to an aspect of the invention there is provided a use of an agent which inhibits the Dystroglycan complex on cardiomyocytes in the manufacture of a medicament for treating a heart disease.

Alternatively, according to an aspect of the invention there is provided a method of treating a heart disease in a subject in need thereof, the method comprising administering to the subject a therapeutically effective amount of an Agrin peptide which induces proliferation of cardiomyocytes, thereby treating the heart disease.

Alternatively, according to an aspect of the invention there is provided a method of treating a heart disease in a subject in need thereof, the method comprising administering to the subject a therapeutically effective amount of an agent which inhibits the Dystroglycan complex on cardiomyocytes, thereby treating the heart disease.

The term "treating" refers to inhibiting, preventing or arresting the development of a pathology (i.e., heart disease, disorder or condition, e.g., ischemic heart disease) and/or causing the reduction, remission, or regression of a pathology. Those of skill in the art will understand that various methodologies and assays can be used to assess the development of a pathology, and similarly, various methodologies and assays may be used to assess the reduction, remission or regression of a pathology.

As used herein, the term "preventing" refers to keeping a disease, disorder or condition from occurring in a subject who may be at risk for the disease, but has not yet been diagnosed as having the disease.

As used herein, the term "subject" includes mammals, preferably human beings at any age that suffer from the pathology. Preferably, this term encompasses individuals who are at risk to develop the pathology.

According to a specific embodiment, the heart disease is an ischemic heart disease.

An ischemic heart disease refers to a lack of oxygen flow to the heart or portion thereof, resulting in myocardial ischemic damage. As used herein, the phrase myocardial ischemic damage includes damage caused by reduced blood flow to the myocardium. Non-limiting examples of causes of an ischemic heart disease and myocardial ischemic damage include: decreased aortic diastolic pressure, increased intraventricular pressure and myocardial contraction, coronary artery stenosis (e.g., coronary ligation, fixed coronary stenosis, acute plaque change (e.g., rupture, hemorrhage), coronary artery thrombosis, vasoconstriction), aortic valve stenosis and regurgitation, and increased right atrial pressure. Non-limiting examples of adverse effects of myocardial ischemia and myocardial ischemic damage include myocyte damage (e.g., myocyte cell loss, myocyte hypertrophy, myocyte cellular hyperplasia), angina (e.g., stable angina, variant angina, unstable angina, sudden cardiac death), myocardial infarction, and congestive heart failure. Damage due to myocardial ischemia may be acute or chronic, and consequences may include scar formation, cardiac remodeling, cardiac hypertrophy, wall thinning, dilatation, and associated functional changes. The existence and etiology of acute or chronic myocardial damage and/or myocardial ischemia may be diagnosed using any of a variety of methods and techniques well known in the art including, e.g., non-invasive imaging (e.g., MRI, echocardiography), angiography, stress testing, assays for cardiac-specific proteins such as cardiac troponin, and evaluation of clinical symptoms. These methods and techniques as well as other appropriate techniques may be used to determine which subjects are suitable candidates for the treatment methods described herein.

According to a specific embodiment, the ischemic heart disease in the present invention includes, for example, coronary arteriosclerosis, acute myocardial infarction (AMI), myocardial infarction (MI), old MI, angina pectoris (AP) including stable angina, unstable angina, and effort angina, ischemic cardiomyopathy, heart failure, and other disease which causes necrosis of heart muscle that results from prolonged ischemia. As necrosis of heart muscle progresses, the damaged myocardiac tissue are replaced with fibrous tissue, thickness of the myocardial wall in the infarct zone gets thinner, and the cardiac inner cavity dilates, therefore cardiac function such as contractility deteriorates and results in heart failure.

Coronary arteriosclerosis is characterized by arteriosclerosis in the coronary artery that supplies nutrients to the heart. Angina pectoris is characterized by attacks of chest pain caused by impaired blood flow in the coronary artery. Myocardial infarction is characterized by myocardial necrosis caused by impaired blood flow in the coronary artery and by fatal complications coming therewith such as arrhythmia, cardiac failure, cardiac rupture, and pump failure. Impaired blood flow to the heart, a vital organ, is an essential characteristic of these ischemic heart diseases.

"Post-infarction myocardial remodeling" refers to a series of changes such as the hypertrophy of myocardial cells at non-infarction sites, increase in interstitial tissue (extracellular matrix), and the dilation of cardiac lumens, which occur in compensation for reduced cardiac function caused by thickening at infarction sites after myocardial infarction. Since long-term prognosis after myocardial infarction is correlated with the degree of left ventricular dysfunction, the suppression of myocardial remodeling is important for maintaining and conserving the function of the left ventricle.

The agents (e.g., Agrin peptide) of some embodiments of the invention can be administered to an organism per se, or in a pharmaceutical composition where it is mixed with suitable carriers or excipients.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the agent (e.g., Agrin peptide) accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, PA, latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, intravenous, intraperitoneal, intranasal, or intraocular injections.

Alternately, one may administer the pharmaceutical composition in a local rather than systemic manner, for example, via injection of the pharmaceutical composition directly into a tissue region of a patient. For example by direct intraventricular, intracardiac, e.g., into the right or left ventricular cavity, into the common coronary artery. Also contemplated is administration of the composition directly to the myocardium e.g., either during open heart surgery or guided by imaging e.g., ultrasound.

Pharmaceutical compositions of some embodiments of the invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with some embodiments of the invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for In example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to some embodiments of the invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of some embodiments of the invention may also be formulated in rectal compositions such as suppositories or retention enemas, using, e.g., conventional suppository bases such as cocoa butter or other glycerides.

Pharmaceutical compositions suitable for use in context of some embodiments of the invention include compositions wherein the active ingredients are contained in an amount effective to achieve the intended purpose. More specifically, a therapeutically effective amount means an amount of active ingredients (e.g., Agrin peptide) effective to prevent, alleviate or ameliorate symptoms of a disorder (e.g., ischemic heart disease) or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide for example, a cardiac tissue levels of the active ingredient that are sufficient to induce or suppress the biological effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

The agent is delivered by an appropriate means to the site of defect (e.g., as described above). The site and subject are observed and tested for regeneration of the defective myocardium to determine that an effective amount of the composition has been delivered, particularly to observe new tissue growth, and also to determine that the new tissue has the contractility necessary for it to function usefully as myocardium. Tissue growth and contractility can be tested and observed by standard means, for example as described in Badylak et al, The Heart Surgery Forum, Extracellular Matrix for Myocardial Repair 6(2) E20-E26 (2003).

Compositions of some embodiments of the invention may, if desired, be presented in a pack or dispenser device, such as an FDA approved kit, which may contain one or more unit dosage forms containing the active ingredient. The pack may, in for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed above.

The agents as described herein can also be immobilized to an implant (e.g., stent) where they can be slowly released therefrom.

The agent as described herein can be combined with other treatment modalities. These other treatments include medication (e.g., blood pressure medication, calcium channel blockers, digitalis, anti-arrhythmics, ACE inhibitors, anticoagulants, immunosuppressants, pain relievers, vasodilators, etc.), angioplasty, stent placement, coronary artery bypass graft, cardiac assist device (e.g., left ventricular assist device, balloon pump), pacemaker placement, heart transplantation, etc. In certain embodiments, the agent provides a bridge to recover for a subject waiting to undergo heart transplantation.

The terms "comprises", "comprising", "includes", "including" "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

When reference is made to particular sequence listings, such reference is to be understood to also encompass sequences that substantially correspond to its complementary sequence as including minor sequence variations, resulting from, e.g., sequencing errors, cloning errors, or other alterations resulting in base substitution, base deletion or base addition, provided that the frequency of such variations is less than 1 in 50 nucleotides, alternatively, less than 1 in 100 nucleotides, alternatively, less than 1 in 200 nucleotides, alternatively, less than 1 in 500 nucleotides, alternatively, less than 1 in 1000 nucleotides, alternatively, less than 1 in 5,000 nucleotides, alternatively, less than 1 in 10,000 nucleotides.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Maryland (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Sterics", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, CT (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839, 153; 3,850,752; 3,850,578; 3,853,987; 3,867,517; 3,879, 262; 3,901,654; 3,935,074; 3,984,533; 3,996,345; 4,034, 074; 4,098,876; 4,879,219; 5,011,771 and 5,281,521; "Oligonucleotide Synthesis" Gait, M. J., ed. (1984): "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. L., ed. (1986); "Immobilized Cells and Enzymes" IRL Press, (1986); "A Practical Guide to Molecular Cloning" Perbal, B., (1984) and "Methods in Enzymology" Vol. 1-317. Academic Press; "PCR Protocols: A Guide To Methods And Applications". Academic Press, San Diego, CA (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Materials and Methods

Isolation of Cardiac Cells

Primary cardiac cells were isolated from ICR 1-day-old (P1) and 7-day-old (P7) mice using a neonatal dissociation kit (gentleMACS), according to the manufacturer's instructions, and cultured in gelatin-coated (0.02%, G1393, Sigma) wells with DMEM/F12 medium supplemented with L-glutamine, Na-pyruvate, non-essential amino acids, penicillin, streptomycin, 5% horse scrum and 10% FBS at 37° C. and 5% $CO_2$. In experiments involving administration of either c-terminal recombinant Agrin (550-AG) (R&D Systems), ECM fragments or broad MMP inhibitors (GM6001, Marimastat), the cells were allowed to adhere for 48 h prior to treatment. Subsequently, the medium was replaced with FBS-free medium containing 5% horse scrum and the indicated treatment doses for 72 h. Cells were fixed in 4% paraformaldehyde (PFA) and stained for markers of interest.

Preparation of Heart Derived ECM

Hearts were taken from ICR mice (1 and 7 day old), and were washed with phosphate-buffered saline (PBS). Hearts were embedded in optimal cutting temperature solution (OCT, tissue-tek) and frozen in −20° C. Hearts were cut transversely into 100 μm fragments using a cryostat. Organ fragments were immersed in 2% Triton X-100 and 20 mM EDTA solution in double distilled water (DDW) overnight at room temperature. The matrixes were then washed with PBS and subsequently placed in 10% Penicillin-Streptomycin Amphotericin B Solution (Biological industries) for sterilization until placement with cells. Prior to matrix administration, fragments were washed with a cell culture medium without FBS (as previously described) and homogenized using gentleMACS M tubes (Miltenyi Biotec Inc). The matrix was then added to cell cultures.

Tissue Culture Immunostaining

Adherent cells were grown on a gelatin-coated 96 well plate. The cells were fixed with 4% PFA in PBS for 10 minutes and permeabilized with 0.2% Triton X-100 in PBS for 5 minutes. The cells were blocked by incubation in PBS containing 0.1% Triton and 3% BSA for 1 hour at room temperature. For immunostaining, the cells were incubated for 2 hours with the following monoclonal antibodies diluted in the blocking solution: Anti-cTnT (1:200, ab33589. Abcam) and anti-cTn1 (1:200, ab47003. Abcam) antibodies were used to identify CMs. Anti-Ki67 antibody (1:200, 275R, Cell Marque), anti-phosphorylated-histone3 (pH3) (1:200, SC-8656-R, Santa Cruz Biotechnology) and anti-aurora B (Aim1, 1:100, 611082. BD Transduction Laboratories) antibodies were used to analyse cell-cycle re-entry, DNA synthesis, karyokinesis and cytokinesis, respectively. Cells were then washed 3 times with PBS and stained for 45 minutes at room temperature with a suitable secondary antibody. This was followed by 5 minutes of DAPI (4,6- diamidino-2-phenylindole dihydrochloride) staining. The cells were viewed under a Nikon fluorescence microscope.

Quantitative Real Time RT-PCR

Total RNA was isolated using the nucleospin RNA II kit (Macherey Nagel) according to the manufacturer's protocol. cDNA was synthesized by using the High Capacity cDNA Reverse Transcription Kit (Applied Biosystems) according to the manufacturer's protocol. qRT-PCR was performed using SYBR Green PCR Master Mix (Applied Biosystems) on Steponeplus Real-Time PCR system (Applied Biosystems). Values for the specific genes were normalized to HPRT housekeeping control. Primer sequences are provided in Table 3 below.

(1:200, sc-374117, Santa Cruz), anti phospho-ERK2 (1:200, M8159, Sigma Aldrich). After three washes with PBS, 10 min each, samples were stained for 1 h at room temperature with fluorescent secondary antibodies (Abcam) followed by 10 min of DAPI (4',6-diamidino-2-phenylindole dihydrochloride) staining for nuclei visualization. Slides were mounted with Immu-mount (9990412, Thermo Scientific) and viewed under a fluorescence microscope (Nikon Intensilight or Nikon eclipse 90i, Nikon) or spinning-disc confocal microscope (Carl Zeiss).

Mouse Experiments

Experiments were approved by the Animal Care and Use Committee of the Weizmann Institute of Science. To track

TABLE 3

| Gene | Forward primer | Reverse primer |
|---|---|---|
| hprt | TGGCCGGCAGCGTTTCTGAG/37 | GTCGGCTCGCGGCAAAAAGC/10 |
| Acta1 | GACATCAAAGAGAAGCTGTG/11 | ACTCCATACCGATAAAGGAAG/12 |
| Pecam | CCAGAAACATCATCATAACCG/17 | CATCGCCACCTTAATAGTTG/18 |
| C090 | GTCAGGCTGGTCACCTTCTG/19 | AACTCTTGGCACCATGAACC/20 |
| aMHC | GCTGGGCTCCCTGGACATTGAC/21 | CCTGGGCCTGGATTCTGGTGAT/22 |
| Vcan | CCAGTGTGAACTTGATTTTGATGAA/23 | AACATAACTTGGGAGACAGAGACATCT/24 |
| Tgfbi | CATCGACGCCCAGATGAAGA/25 | TGGTGAACAGGGTCCCAAAC/26 |
| Dag1 | CGGAGGAGCGAACACCTG/27 | GTTGGATCCTCACCCTCTGC/28 |
| Agrn | TTCGATGGTCCTTGTGACCC/29 | AGATAGGTGTGTGTTGGGCG/30 |
| Col1861 | GTGCCCATCGTCAACCTGAA/31 | AGTTGACCCTGGGAGCCAGA/32 |
| Dcn | CCTTCTGGCACAAGTCTCTTGG/33 | TCGAAGATGACACTGGCATCGG/34 |
| Lum | TCGAGCTTGATCTCTCCTAT/35 | TGGTCCCAGGTCTTACAGAA/36 |

Western Blot Analysis

Western blotting was performed with the SDS-PAGE Electrophoresis System. Total heart tissue extracts were prepared, and transferred to PVDF membranes. The following primary antibodies were used: anti-Agrn (sc-374117, Santa Cruz), anti alpha-dystroglycan (05-298, Millipore), anti-Gapdh (2118, Cell signaling technologies), Anti-cTnT (ab33589, Abcam) and anti-cTn1 (ab47003, Abcam), anti-ERK2 (sc-154, Santa Cruz), anti-phospho-ERK (no. 4370, Cell Signaling), anti alpha-tubulin (T5168, Sigma-Aldrich). A horseradish peroxidase anti-mouse, anti-rabbit or anti-goat (Sigma) was used as the secondary antibody.

Immunofluorescence Analysis

Heart sections underwent deparaffinization and microwave antigen retrieval in EDTA or citric acid buffer, followed by gradual chilling. Samples were permeabilized with 0.5% Triton X-100 in PBS for 5 min and blocked with 5% bovine serum albumin (BSA) in PBS containing 0.1% Triton for 1 h at room temperature. Then samples were incubated overnight at 4° C. with the following antibodies diluted in 3% BSA blocking solution and 1% horse serum. Anti-cTnT (1:200, ab33589, Abcam) and anti-cTn1 (1:200, ab47003, Abcam) antibodies were used to identify CMs. Anti-Ki67 antibody (1:200, 275R, Cell Marque), anti-phosphorylated-histone3 (pH3) (1:200, SC-8656-R, Santa Cruz Biotechnology) and anti-aurora B (Aim1, 1:100, 611082, BD Transduction Laboratories) antibodies were used to analyse cell-cycle re-entry, DNA synthesis, karyokinesis and cytokinesis, respectively. Other antibodies used in the study: anti-Agrn the cardiac muscle cell lineage. αMHC-Cre and ROSA426-tdTomato mice were intercrossed. αMHC-Cre mice carry the Cre coding sequence inserted after the alpha myosin heavy chain promoter (αMHC), which can drive high-efficiency gene recombination in CMs. ROSA26-tdTomato indicator mice harbor a conditional red fluorescent protein variant allele that requires CRE-mediated recombination for expression. This system allowed clear visualization of RFP-labeled CMs in culture. ROSA26-tdTomato and αMHC-Cre mice were maintained on a C57BL/6 background. To test the effect of Agrin in cardiac regeneration Agrn$^{flox/flox}$ (43) were intercrossed to Agrn$^{flox/flox}$; Mesp1-Cre mice (44). Mesp1 is expressed in the nascent mesoderm during early gastrulation and it marks the most cardiac progenitor populations which include the majority of heart cells (CMs, Fibroblasts and endothelial cells). The conditional knockout mouse allowed to understand the contribution of Agrin to cardiac regeneration in neonatal pups (P1).

Myocardial Infarction

Myocardial infarction at P7 or adult stages were induced by ligation of the left anterior descending coronary artery, P7 mice were anaesthetized by cooling on an ice bed for 4 min, whereas adult mice were sedated with isoflurane (Abbott Laboratories) and, following tracheal intubation, were artificially ventilated. Lateral thoracotomy at the third intercostal space was performed by blunt dissection of the intercostal muscles following skin incision. Following ligation of the left anterior descending coronary artery. Intramyocardial injections of Agrin (50 μl at 20 μg/ml) or PBS were administered. Following treatment, thoracic wall incisions were sutured with 6.0 non-absorbable silk sutures, and the skin wound closed using a skin adhesive. Mice were then warmed for several minutes until recovery.

Echocardiography

Heart function was evaluated by transthoracic echocardiography performed on sedated mice (isoflurane, Abbott Laboratories) using a Vevo 770 VisualSonics device.

Histology

Mouse heart tissues were fixed in 4% paraformaldehyde (PFA) and sectioned. For analysis of juvenile and adult cardiac regeneration following myocardial infarction procedure, paraffin sections were cut through the entire ventricle from apex to base into serial sections with intervals of 0.4 mm. For analysis of neonatal cardiac regeneration following resection, paraffin sections were cut frontally to include base to apex in each section. Haematoxylin-cosin (H&E). Masson's trichrome and Sirius red staining were performed according to standard procedures and used to for detection of fibrosis. Scar size was quantified in the section containing the papillary muscle region using ImageJ software based on Masson's trichrome staining. Adult and juvenile scar size was calculated as scar size relative to total section size, whereas neonatal scar size was calculated as scar size relative to LV size.

Example 2

P1 Cardiac ECM Increases CM Proliferation in a MMP Dependent Manner

The effect of the cardiac ECM on CM turnover during the regenerative timeframe in mice was determined {Porrello, 2011 #11}. For that purpose P1 and P7 hearts underwent decellularization (FIG. 1A) to produce cell free ECM fragments as confirmed by DAPI staining and scanning electron microscopy (FIGS. 1B-1C). In vitro administration of P1 ECM fragments promoted an increase in both P1 and P7 CM cell-cycle activity, whereas P7 ECM fragments reduced cell cycle re-entry (FIGS. 1D-1F).

To gain further insights into the mechanism by which P1 ECM induces CM proliferation, a broad MMP inhibitor (Marimastat) was administered to the culture. Addition of the inhibitor to CM cultures containing ECM fragments derived from P1 hearts abolished the activation of CM proliferation by the P1 ECM explants (FIGS. 1G-1H). Addition of the inhibitor to either control cultures or to cultures with ECM fragments derived from P7 hearts, did not influence CM proliferation rate (FIGS. 1G-1H).

In order to validate the involvement of MMP2/9 in releasing ECM-related peptides that induce CM proliferation, in situ zymography (ISZ) assay that measures the cleavage of substrates, collagen type 1 (Col1), collagen type 4 (Col4) or gelatin into a fluorescent signal in the presence of ECM fragments was used (FIG. 1N). The highest change observed amongst the three substrates was for Col4 and gelatins, suggesting an involvement of the Gelatinase family of MMPs, MMP2/9 (FIGS. 1O-1P).

Next, in order to test if a specific ligand/peptide in the P1 ECM cleaved by MMP2/9 is sufficient to promote CM proliferation, P1 ECM was incubated with MMP2, MMP9, or MMP12 (FIG. 1I). P1 ECM explants digested with MMP2/9 resulted in a striking increase in CM proliferation of either P1 (FIG. 1J) or P7 (FIG. 1K) cells, whereas MMP12 cleaved ligands resulted in increase in CM proliferation, albeit lower.

To identify unique P1 ECM associated proteins that contribute to the enhanced CM proliferation, MMP9 cleaved P1 and P7 ECM related proteins were analyzed by mass spectroscopy (LC/MS) (FIG. 1L). This technique identified a previously reported contribution of Tgfbi, a paralog of Periostin that was shown to promote CM proliferation [12,45]. Other ECM proteins which were enriched in P1 vs. P7 include Col18a1 (Endostatin) and Vcan (FIG. 1M). In addition, Agrin, an ECM HSPG, was identified as enriched in P1 relative to P7 ECM explants (FIG. 1M). Finally, the observed changes in expression levels were validated by qRT-PCR in P1 and P7 whole hearts, which are consistent with the results of the proteomic analysis (FIG. 1M). Taken together a novel methodology to dissect ECM related CM proliferation-promoting molecules was demonstrated and MMP2/9 remodeling of P1 but not P7 cardiac ECM can lead to subsequent release of these ligands that promote CM proliferation in vitro.

Example 3

Endocardial/Endothelial Derived Agrin Promotes CM Proliferation

The expression levels of Agrin in the heart were then tested {Moll, 2001 #111; McKee, 2009 #112}. Immunofluorescence analysis validated previous finding showing the downregulation of Agrin expression (RNA and protein) at P7 hearts, compared to P1 (FIGS. 2A-2C). Next, the cell population which produces Agrin was identified. To do so, P1 cardiac cells were separated to 3 different populations: CMs, fibroblasts (FBs) and endothelial cells (ECs). Enrichment of CMs, FBs and ECs cell populations was confirmed using qPCR for known markers of each cell population (αMHC, CD90 and CD31, respectively, FIG. 2I). Agrin mRNA expression was significantly enriched in the EC population relative to all other cell types (FIG. 2D). The reduction of Agrin expression during the first week of life correlates with the loss of cardiac regenerative response in mice, therefore, it may suggest a role for Agrin during the regeneration process (as shown in FIGS. 3A-3O).

The ability of Agrin to induce CM proliferation in culture was then determined. Agrin treatment resulted in a dose-dependent increase in CM proliferation, as measured by immunofluorescence staining for markers of cell-cycle activity (Ki67), mitosis (phospho-Histone H3) and cytokinesis (Aurora B kinase), and by counting the number of newly formed CMs at P1 and P7 (FIGS. 2E-2H).

Example 4

Agrin is Required for Cardiac Regeneration in Neonatal Mice

In order to understand whether Agrin is required for cardiac regeneration at birth following the surgical resection technique {Porrello, 2011 #11; Porrello, 2012 #38}, Agrin was conditionally deleted in the majority of heart cell populations by crossing Mesp1-Cre$^{+/-}$; Agrin$^{flox/+}$ {Harvey, #113; Kitajima, 2006 #114} with Agrin$^{flox/flox}$ mice (FIG. 3A). Analyses of Agrin protein and mRNA expression in Mesp1-Cre$^{+/-}$; Agrin$^{flox/flox}$ (Agrin-cKO) hearts confirmed that the Agrin flox allele was efficiently deleted in the heart (FIGS. 3B-3D). Interestingly, at P1 Agrin-cKO mice expressed to elevated sarcomeric proteins (cTnT and cTn1) (FIG. 3C) with a marked increase in sarcomeric organization as seen by cTnT staining (FIG. 3H). WGA membrane staining revealed a small increase in cardiac cell size (FIGS. 3E-3F) which was consistent with elevated pathological hypertrophy {Houweling, 2005 #115:Yc, 2003 #116} {Baum, 2011 #12} Marker, skeletal-actin (Acta1) {Black, 1991 #117}

(FIG. 3G). Moreover, CM cell cycle activity was significantly reduced in Agrin-cKO mice after birth (FIGS. 3H-3I). These findings suggest that Agrin suppresses CM maturation processes and in the absence of Agrin, CMs display a compensatory mechanism for cardiac hypertrophy and increased differentiation.

Next, the question whether cardiac regeneration is impaired in Agrin-cKO mice was investigated. For that P1 mice underwent cardiac resection and cardiac regeneration was assessed after 1 and 4 weeks (by proliferation or by fibrosis respectfully) (FIG. 3J). Histological examination using Mason's trichrome and Sirius red stain displayed elevated fibrosis in the Agrin-cKO mice relative to wild-type littermate (FIGS. 3K-3M). In line with these findings. CM proliferation was significantly reduced in Agrin cKO mice (FIG. 3N). Taken together, the present results suggest Agrin as a crucial component during cardiac regeneration and suggest it may play a role as an inhibitor of CM differentiation during the first postnatal week.

Example 5

Agrin Treatment Promotes Cardiac Regeneration Following MI

Figures 4A, 4B, 4C:
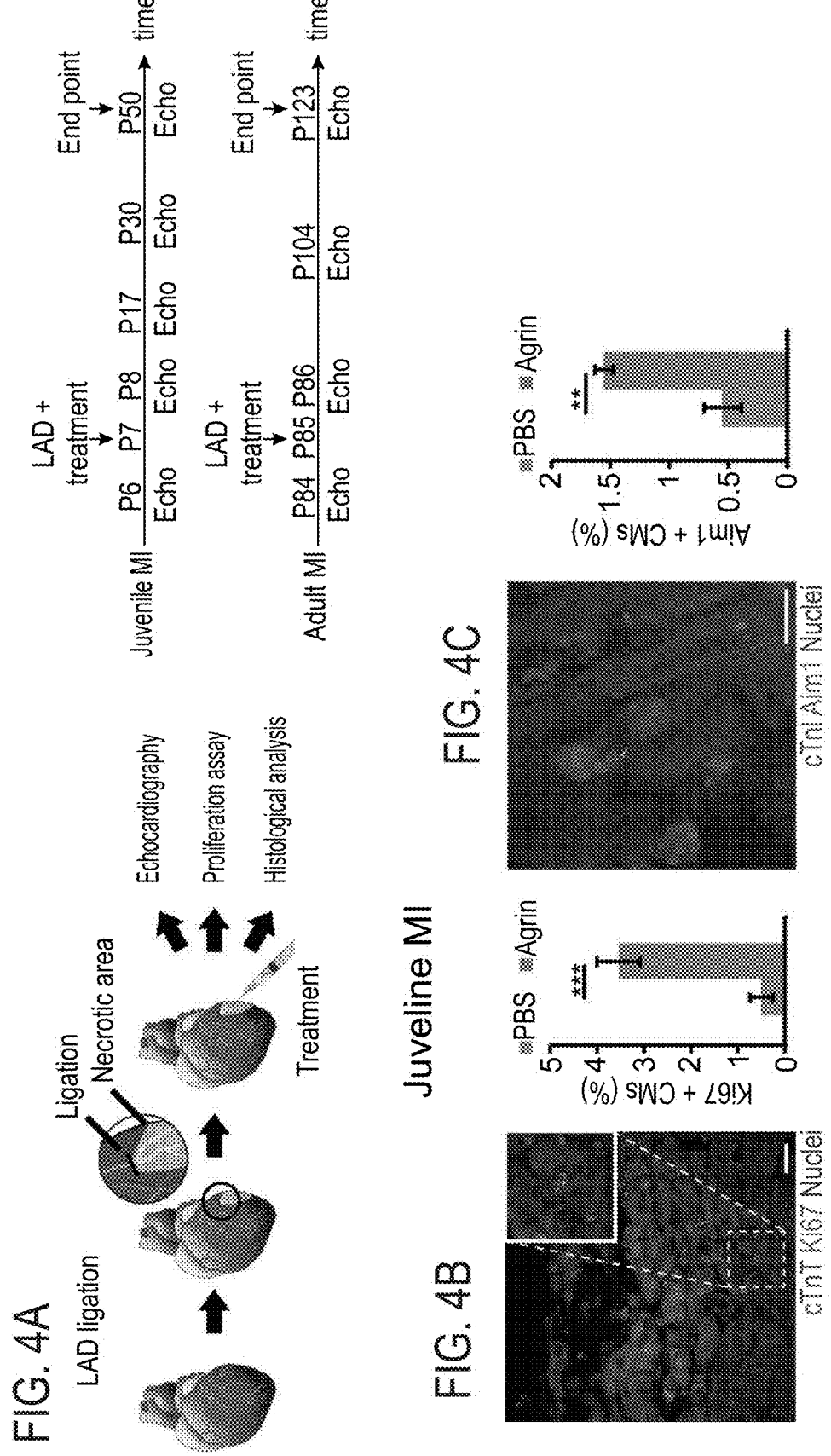
Figures 4D, 4E, 4F:
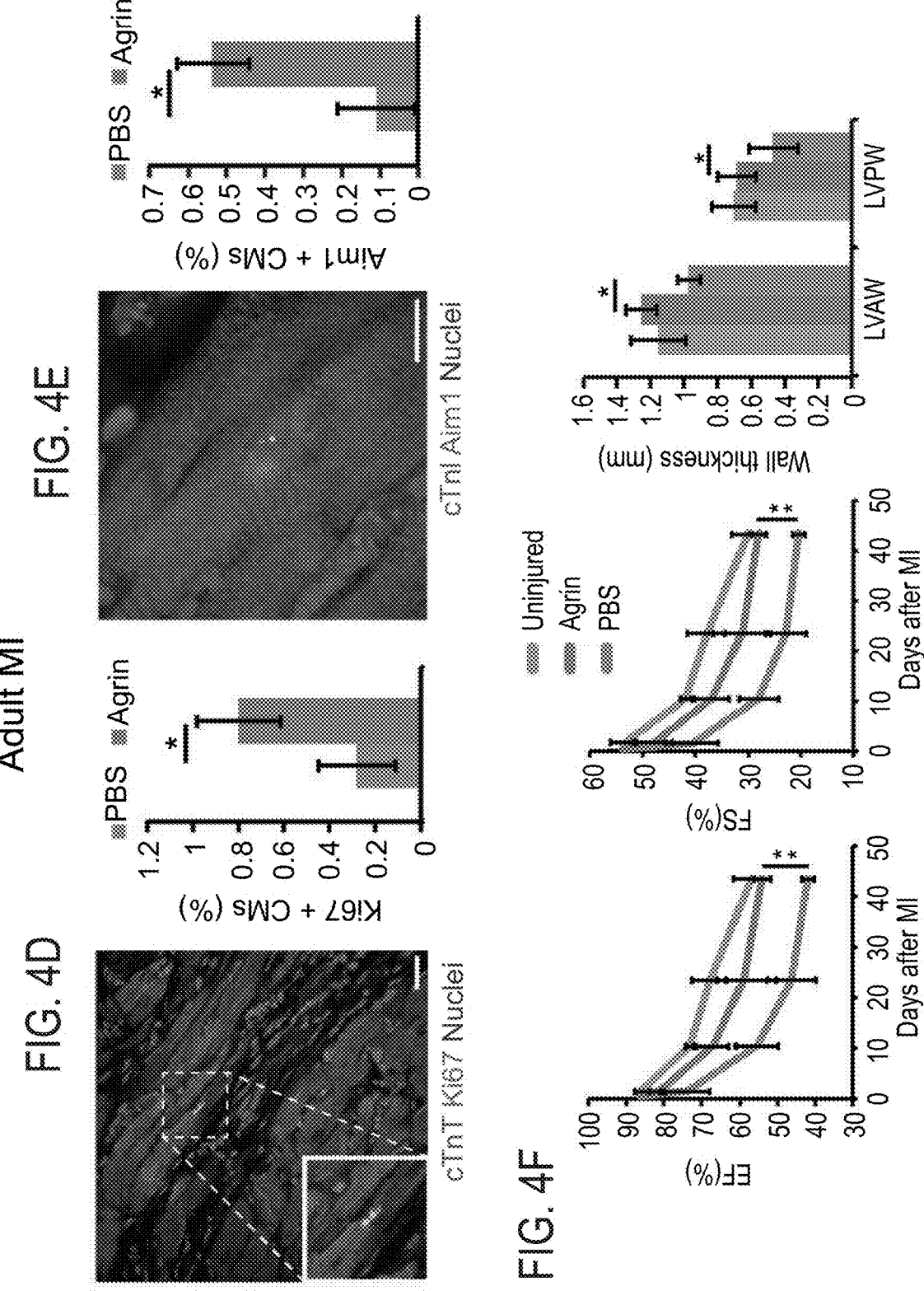

Next, the question whether Agrin could similarly promote CM proliferation and cardiac regeneration in juvenile and adult stages was investigated. Accordingly, P7 and P85 mice were subjected to permanent ligation of the left anterior descending artery (LAD) that were treated with either Agrin or PBS (FIG. 4A). Intramyocardial injection of Agrin (1 μg in 50 μl) induced CM cell cycle re-entry in the healthy myocardium adjacent to the infarcted region of both juvenile and adult hearts (FIGS. 4B-4E). A single Agrin injection following MI was sufficient to improve recovery of cardiac function as evident by echocardiography, in both juvenile and adult models (FIGS. 4F-4G). Moreover, both juvenile and adult Agrin treated mice showed a significant retention of wall thickness and protection from dilated cardiomyopathy, in contrast to PBS treated mice (FIGS. 4F-4G). Histological analyses in both juvenile and adult, revealed significant reduction in fibrosis, albeit fibrotic tissue was present in both treatments (FIGS. 4H-4I). Taken together, the present results demonstrate that re-introduction of Agrin to failing hearts facilitates cardiac regeneration as a result of increased CM cell cycle activity and cytokinesis and subsequent reduction of scaring and better cardiac function.

Example 6

Agrin Promotes CM Proliferation Through Dag1 and ERK Activation

Previous reports on Agrin signaling have implicated inhibition of $Na^+/K^+$ pumps. Lrp4-Musk or α-Dystroglycan as possible receptors modulating its activity. Earlier work focusing on cardiac regeneration in mice following MI has established that cardiac mRNA transcript levels of Lrp4 and MuSK are very low {Haubner, 2012 #130}. Furthermore, it has been shown that Agrin can inhibit $Na^+/K^+$ pumps via direct interaction with CAF22 fragment and therefore affect CM beating {Hilgenberg, 2009 #103}. Improvement in cardiac function can be attributed to several aspects, one of which is synchronization of the beating of the myocardium {Abraham, 2002 #118; Sullivan, 1989 #119}, as well as adult CM proliferation. No increase in CM proliferation by inhibiting the pump was observed (FIG. 5J). Thus it is suggested that Agrin signaling is mediated by Dag1 in CMs. Thus it was hypothesized that Agrin signaling is mediated by Dag1 in CMs. For that, the present inventors aimed to identify the cell population expressing Dag1 which potentially interact with Agrin. Using qPCR for Dag1 revealed expression in all cell types isolated from P1 hearts, however its expression was particularly enriched in CMs, this enrichment became more striking in P8 heart cultures (FIGS. 5A-5C). Agrin activity has been associated with ERK activation during monocyte maturation {Aurora, 2014 #125}. Similarly, the present inventors observed transient ERK activation following Agrin treatment in vitro, peaking at 5 minutes with sustained activation up to 15 minutes post treatment in cardiac cell culture as measured by western blot and immunofluorescence (FIGS. 5D-5E). Next, the question of the interaction of Agrin with Dag1 and its requirement for ERK activation was examined. Indeed addition of a blocking antibody (IIH6C4) directed against Dag1-Agrin binding site {Aurora, 2014 #125} diminished Agrin-induced ERK activation (FIG. 5F). Furthermore, in order to understand whether the interaction of Agrin with Dag1 and subsequent ERK activation was required for Agrin induced proliferation; IIH6C4 antibody and MEK inhibitor (PD0325901) were added to P7 CM cell cultures and CM proliferation was analyzed (FIGS. 5G-5H). As expected, inhibition of either ERK activation or the Dag1-Agrin interaction suppressed Agrin induced CM proliferation.

Following this, the present inventors wanted to examine whether Agrin-Dystroglycan signal was propagated through dystrophin, for that mdx mice 1551 in which dystrophin expression is abolished were used.

Cardiac cells from control and Mdx mice were cultured and treated with Agrin, CM proliferation induced by Agrin was not changed between the two types of mice (FIG. 5I). Taken together, Agrin induced CM proliferation via interaction with Dag1 and subsequent ERK activation, in a dystrophin-independent manner.

Example 7

In-Vitro Agrin Administration Promotes Human iPSC-Derived CMs Proliferation

To understand whether Agrin could promote CM proliferation in cells derived from human tissues. Agrin was added to human iPSC derived CMs (hiPSC-CM) and examined by proliferation markers. In vitro administration of Agrin promoted a dose-dependent increase of hiPSC-CM cell-cycle activity (FIGS. 6A-6B). Likewise, in vitro administration of human Agrin promoted a dose-dependent increase of hiPSC-CM cell-cycle activity (FIGS. 6C-6D).

Example 8

RNA-Seq of Agrin Treated Hearts Revels Implications to Agrin Immune-Related Mechanism To asses Agrin genome wide transcriptional effect in the infarcted hearts, RNA-seq analysis of Agrin treated MI hearts was performed. Adult (3 months) mice were subjected to LAD ligation or sham operation (sec FIG. 4A). The LAD ligated animals were injected with either Agrin or PBS (vehicle) epimyocardialy immediately after MI (FIG. 8A). Hearts were collected 3 days post treatment, and RNA samples were purified and subjected to RNA-seq. Genome wide expression of infarcted hearts treated with either PBS or Agrin was compared. 175 genes were differentially expressed (threshold of fold change >1.5, p-value <0.05, see FIG. 8B). To focus on the relevant transcriptional effect, present data was compared to a former established RNA-seq of wild type infarcted hearts, performed by Ounzain et al.

Genome-wide profiling of the cardiac transcriptome after myocardial infarction identifies novel heart-specific long non-coding RNAs. Eur Heart J 36, 353-368a, doi:10.1093/eurheartj/ehu180 (2015).

This comparison allowed defining the common genes that are differentially expressed in infracted untreated hearts, serving as an "MI signature". It was found that 558 genes were differentially expressed (mostly up regulated) in infarcted hearts compared to sham operated hearts, both in the present settings and in Ounzain's datasets (FIG. 8C). Looking at these genes in the infarcted hearts treated with Agrin, it was found that most of them showed the opposite trend in Agrin treated hearts compared to PBS treated hearts (FIG. 8C), indicating that these genes comprise the Agrin-affected transcriptional network.

To gain insight into the cellular and molecular processes this gene set portrays, the gene set was analyzed using ingenuity pathway analysis (IPA) software. Interestingly, looking at both canonical pathways (FIG. 8D) and upstream regulators (FIG. 8E), it was found that many relate to modulation of the MI-related immune response; i.e., 116 is known to promote cardiomyocytes apoptosis. Tgf-beta is well established as a fibrosis promoter and several canonical pathways regulating immune cells migration and maturation (Leukocytes extravasation signaling. Dendritic cell maturation) were also implicated. Examples for genes involved in the different enriched terms are given in FIGS. 8F-8H. Taken together, this data suggested that Agrin promotes heart regeneration not only through cardiomyocyte proliferation by also by immune modulation, which might change cardiomyocyte survival thereby reducing infarct and scar size.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

REFERENCES

Other References are Cited Throughout the Application

1 Bergmann, O., et al., *Evidence for Cardiomyocyte Renewal in Humans*. Science, 2009. 324(5923): p. 98-102.

2 Senyo, S. E., et al., *Mammalian heart renewal by pre-existing cardiomyocytes*. Nature, 2013. 493(7432): p. 433-436.

3 Poss, K. D., *Getting to the heart of regeneration in zebrafish*. Seminars in Cell & Developmental Biology, 2007. 18(1): p. 36-45.

4 Ausoni, S. and S. Sartore, *From fish to amphibians to mammals: in search of novel strategies to optimize cardiac regeneration*. The Journal of Cell Biology, 2009. 184(3): p. 357-364.

5 Jopling, C., et al., *Zebrafish heart regeneration occurs by cardiomyocyte dedifferentiation and proliferation*. Nature, 2010. 464(7288): p. 606-609.

6 Porrello, E. R., et al., *Transient Regenerative Potential of the Neonatal Mouse Heart*. Science, 2011. 331(6020): p. 1078-1080.

7 Porrello, E. R., et al., *Regulation of neonatal and adult mammalian heart regeneration by the miR-15family*. Proceedings of the National Academy of Sciences, 2012.

8 Li, F., et al., *Rapid Transition of Cardiac Myocytes from Hyperplasia to Hypertrophy During Postnatal Development*. Journal of Molecular and Cellular Cardiology, 1996. 28(8): p. 1737-1746.

9 Soonpaa, M. H. and L. J. Field, *Survey of Studies Examining Mammalian Cardiomyocyte DNA Synthesis*. Circulation Research, 1998. 83(1): p. 15-26.

10 Weisman, H. F., et al., *Cellular mechanisms of myocardial infarct expansion*. Circulation, 1988. 78(1): p. 186-201.

11 Engel, F. B., et al., *FGF1/p38 MAP kinase inhibitor therapy induces cardiomyocyte mitosis, reduces scarring, and rescues function after myocardial infarction*. Proceedings of the National Academy of Sciences, 2006. 103(42): p. 15546-15551.

12 Kuhn, B., et al., *Periostin induces proliferation of differentiated cardiomyocytes and promotes cardiac repair*. Nat Med, 2007. 13(8): p. 962-969.

13 D'Uva, G., et al., *ERB2 triggers mammalian heart regeneration by promoting cardiomyocyte dedifferentiation and proliferation*. Nat Cell Biol, 2015. 17(5): p. 627-638.

14 Bersell, K., et al., *Neuregulin1/Erb84 Signaling Induces Cardiomyocyte Proliferation and Repair of Heart Injury*, Cell, 2009. 138(2): p. 257-270.

15 Heallen, T., et al., *Hippo signaling impedes adult heart regeneration*. Development, 2013. 140(23): p. 4683-4690.

16 Mahmoud, A. L., et al., *Meis1 regulates postnatal cardiomyocyte cell cycle arrest*. Nature, 2013. 497(7448): p. 249-253.

17 Baum, J. and H. S. Duffy, *Fibroblasts and Myofibroblasts: What Are We Talking About?* Journal of Cardiovascular Pharmacology, 2011. 57(4): p. 376-379 10.10/97FJC.0b013c3182116c39.

18 Bayomy, A. F., et al., *Regeneration in heart disease—Is ECM the key?* Life Sciences, 2012. 91(17-18): p. 823-827.

19 Phatharajaree, W., A. Phrommintikul, and N. Chattipakorn, *Matrix metalloproteinases and myocardial infarction*. The Canadian Journal of Cardiology, 2007. 23(9): p. 727-733.

20 DeCoux, A., et al., *Myocardial matrix metalloproteinase-2: inside out and upside down*. Journal of Molecular and Cellular Cardiology, 2014. 77: p. 64-72.

21 Hayashidani, S., et al., *Targeted deletion of MMP-2 attenuates early LV rupture and late remodeling after experimental myocardial infarction*. American Journal of Physiology—Heart and Circulatory Physiology, 2003. 285(3): p. H1229-H1235.

22 Ducharme, A., et al., *Targeted deletion of matrix metalloproteinase-9 attenuates left ventricular enlargement and collagen accumulation after experimental myocardial infarction*. Journal of Clinical Investigation, 2000. 106(1): p. 55-62.

23 Ridley, A. J., et al., *Cell Migration: Integrating Signals from Front to Back*. Science, 2003. 302(5651): p. 1704-1709.

24 Berk, B. C., K. Fujiwara, and S. Lehoux, *ECM remodeling in hypertensive heart disease*. Journal of Clinical Investigation, 2007. 117(3): p. 568-575.

25 Shamis, Y., et al., *Organ specific scaffolds for in vitro expansion, differentiation and organization of primary lung cells*. Tissue Engineering Part C—Methods, 2011. 17(8): p. 861-870.

26 Streuli, C., *Extracellular matrix remodelling and cellular differentiation*. Current Opinion in Cell Biology, 1999. 11(5): p. 634-640.

27 Williams, C., et al., *Young developmental age cardiac extracellular matrix promotes the expansion of neonatal cardiomyocytes in vitro*. Acta Biomaterialia, 2014. 10(1): p. 194-204.

28 Williams, S., C. Ryan, and C. Jacobson, *Agrin and neuregulin, expanding roles and implications for therapeutics*. Biotechnology Advances, 2008. 26(3): p. 187-201.

29 Burden, S. J., N. Yumoto, and W. Zhang, *The Role of MuSK in Synapse Formation and Neuromuscular Disease*. Cold Spring Harbor Perspectives in Biology, 2013. 5(5.

30 Theocharis, A. D., et al., *Proteoglycans in health and disease: novel roles for proteoglycans in malignancy and their pharmacological targeting*. FEBS Journal, 2010. 277(19): p. 3904-3923.

31 Chakraborty, S., et al., *An oncogenic role of Agrin in regulating focal adhesion integrity in hepatocellular carcinoma*. Nat Commun, 2015. 6.

32 Hilgenberg, L. G. W., et al., *Agrin Regulation of α3 Sodium-Potassium ATPase Activity Modulates Cardiac Myocyte Contraction*. Journal of Biological Chemistry, 2009. 284(25): p. 16956-16965.

33 Schwinger, R. H. G., et al., *The Na, K-ATPase in the failing human heart*. Cardiovascular Research, 2003. 57(4): p. 913-920.

34 Mazzon, C., et al., *Agrin is required for survival and function of monocytic cells*. Blood, 2012. 119(23): p. 5502-5511.

35 Henry, M. D. and K. P. Campbell, *Dystroglycan: an extracellular matrix receptor linked to the cytoskeleton*. Current Opinion in Cell Biology, 1996. 8(5): p. 625-631.

36 Davies, K. E. and K. J. Nowak, *Molecular mechanisms of muscular dystrophies: old and new players*. Nat Rev Mol Cell Biol, 2006. 7(10): p. 762-773.

37 Ervasti, J. M., et al., *Deficiency of a glycoprotein component of the dystrophin complex in dystrophic muscle*. Nature, 1990. 345(6273): p. 315-319.

38 Campbell, K. P. and S. D. Kahli, *Association of dystrophin and an integral membrane glycoprotein*. Nature, 1989. 338(6212): p. 259-262.

39 Richardson, G. D., S. Laval, and W. A. Owens, *Cardiomyocyte Regeneration in the mdx Mouse Model of Nonischemic Cardiomyopathy*. Stem Cells and Development, 2015: p. 1672-1679.

40 Morikawa, Y., et al., *Actin cytoskeletal remodeling with protrusion formation is essential for heart regeneration in Hippo-deficient mice*. Science Signaling, 2015. 8(375): p. ra41-ra41.

41 Haubner, B. J., et al., *Complete cardiac regeneration in a mouse model of myocardial infarction*. Aging (Albany NY), 2012. 4(12): p. 966-977.

42 Singhal, N. and P. T. Martin, *Role of extracellular matrix proteins and their receptors in the development of the vertebrate neuromuscular junction*. Developmental Neurobiology, 2011. 71(11): p. 982-1005.

43 Harvey, S. J., et al., *Disruption of Glomerular Basement Membrane Charge through Podocyte-Specific Mutation of Agrin Does Not Alter Glomerular Permselectivity*. The American Journal of Pathology, 2007. 171(1): p. 139-152.

44 Saga. Y., et al., *MesP1 is expressed in the heart precursor cells and required for the information of a single heart tube*. Development, 1999. 126(15): p. 3437-3447.

45 Hoersch, S. and M. Andrade-Navarro, *Periostin shows increased evolutionary plasticity in its alternatively spliced region*. BMC Evolutionary Biology, 2010. 10(1): p. 30.

46 Moll, J., et al., *An agrin minigene rescues dystrophic symptoms in a mouse model for congenital muscular dystrophy*. Nature, 2001. 413(6853): p. 302-307.

47 McKee, K. K., S. Capizzi, and P. D. Yurchenco, *Scaffold-forming and Adhesive Contributions of Synthetic Laminin-binding Proteins to Basement Membrane Assembly*. The Journal of Biological Chemistry, 2009. 284:(13) p. 8984-8994.

48 Kitajima, S., et al., *Mesp1-nonexpressing cells contribute to the ventricular cardiac conduction system*. Developmental Dynamics, 2006. 235(2): p. 395-402.

49 Houweling, A. C., et al., *Expression and regulation of the atrial natriuretic factor encoding gene Nppa during development and disease*. Cardiovascular Research, 2005. 67(4): p. 583-593.

50 Ye, P. and M. J. West, *Cosegregation analysis of natriuretic peptide genes and blood pressure in the spontaneously hypertensive rat*. Clinical and Experimental Pharmacology and Physiology, 2003. 30(12): p. 930-936.

51 Black, F. M., et al., *The vascular smooth muscle alpha-actin gene is reactivated during cardiac hypertrophy provoked by load*. The Journal of Clinical Investigation, 1991. 88(5: (p. 1581-1588.

52 Abraham, W. T., et al., *Cardiac Resynchronization in Chronic Heart Failure*. New England Journal of Medicine, 2002. 346(24): p. 1845-1853.

53 Sullivan, M., et al., *Increased exercise capacity after digoxin administration in patients with heart failure*. Journal of the American College of Cardiology, 1989. 13(5): p. 1138-1143.

54 Aurora, A. B., et al., *Macrophages are required for neonatal heart regeneration*. The Journal of Clinical Investigation, 2014. 124(3): p. 1382-1392.

55 Im, W. B., et al., *Differential Expression of Dystrophin Isoforms in Strains of mdx Mice with Different Mutations*. Human Molecular Genetics, 1996. 5(8): p. 1149-1153.

---

What is claimed is:

1. A method of inducing proliferation of cardiomyocytes, the method comprising contacting the cardiomyocytes with an effective amount of an agrin peptide comprising a fragment of SEQ ID NO: 5, wherein the agrin peptide is 80-100 kDA.

2. The method of claim 1, wherein the agrin peptide induces immune modulation.

3. The method of claim 1, wherein the agrin peptide induces Erk activation.

4. The method of claim 1, wherein the agrin peptide inhibits sarcomerogenesis.

5. The method of claim 1, wherein the fragment of SEQ ID NO: 5 comprises amino acids 1260-2045 of SEQ ID NO: 5.

6. The method of claim 1, wherein the agrin peptide is not part of a fusion polypeptide.

7. The method of claim 1, wherein the agrin peptide comprises a Laminin G-like 1 domain (G1) and Laminin G-like domain (G2).

8. A method of treating a heart disease in a subject in need thereof, comprising administering to the subject an agrin peptide comprising a fragment of SEQ ID NO: 5, wherein the agrin peptide is 80-110 kDA.

9. The method of claim 8, wherein the agrin peptide induces immune modulation.

10. The method of claim 8, wherein the agrin peptide induces Erk activation.

11. The method of claim 8, wherein the agrin peptide inhibits sarcomerogenesis.

12. The method of claim 8, wherein the fragment of SEQ ID NO: 5 comprises amino acids 1360-2045 of SEQ ID NO: 5.

13. The method of claim 8, wherein the agrin peptide is not part of a fusion polypeptide.

14. The method of claim 8, wherein the agrin peptide comprises a Laminin G-like 1 domain (G1) and a Laminin G-like 2 domain (G2).

15. The method of claim 8, wherein the heart disease is an ischemic heart disease.

16. The method of claim 8, wherein the heart disease is selected from the group consisting of coronary arteriosclerosis, acute myocardial infarction (AMI), myocardial infarction (MI), old MI, angina pectoris (AP), ischemic cardiomyopathy and heart failure.

17. A method of inducing Erk activation in a cardiomyocyte, comprising contacting the cardiomyocyte with an agrin peptide comprising a fragment of SEQ ID NO. 5, wherein the agrin peptide is 80-100 kDA.

18. The method of claim 17, wherein the fragment of SEQ ID NO: 5 comprises amino acids 1260-2045 of SEQ ID NO: 5.

19. The method of claim 17, wherein the agrin peptide comprises a Laminin G-like 1 domain (G1) and a Laminin G-like 2 domain (G2), and wherein the agrin peptide is not part of a fusion polypeptide.

* * * * *

SEQUENCE LISTING

```
Sequence total quantity: 38
SEQ ID NO: 1            moltype = AA  length = 4392
FEATURE                Location/Qualifiers
source                 1..4392
                       mol_type = protein
```

```
                                organism = Homo sapiens
SEQUENCE: 1
MGWRAAGALL LALLLHGRLL AVTHGLRAYD GLSLPEDIET VTASQMRWTH SYLSDDEDML    60
ADSISGDDLG SGDLGSGDFQ MVYFRALVNF TRSIEYSPQL EDAGSREFRE VSEAVVDTLE   120
SEYLKIPGDQ VVSVVFIKEL DGWVFVELDV GSEGNADGAQ IQEMLLRVIS SGSVASYVTS   180
PQGFQFRRLG TVPQFPRACT EAEFACHSYN ECVALEYRCD RRPDCRDMSD ELNCEEPVLG   240
ISPTFSLLVE TTSLPPRPET TIMRQPPVTH APQPLLPGSV RPLPCGPQEA ACRNGHCIPR   300
DYLCDGQEDC EDGSDELDCG PPPPCEPNEF PCGNGHCALK LWRCDGDFDC EDRTDEANCP   360
TKRPEEVCGP TQFRCVSTNM CIPASFHCDE ESDCPDRSDE FGCMPPQVVT PPRESIQASR   420
GQTVTFTCVA IGVPTPIINW RLNWGHIPSH PRVTVTSEGG RGTLIIRDVK ESDQGAYTCE   480
AMNARGMVFG IPDGVLELVP QRAGPCPDGH FYLEHSAACL PCFCFGITSV CQSTRRFRDQ   540
IRLRFDQPDD FKGVNVTMPA QPGTPPLSST QLQIDPSLHE FQLVDLSRRF LVHDSFWALP   600
EQFLGNKVDS YGGSLRYNVR YELARGMLEP VQRPDVVLMG AGYRLLSRGH TPTQPGALNQ   660
RQVQFSEEHW VHESGRPVQR AELLQVLQSL EAVLIQTVYN TKMASVGLSD IAMDTTVTHA   720
TSHGRAHSVE ECRCPIGYSG LSCESCDAHF TRVPGGPYLG TCSGCNCNGH ASSCDPVYGH   780
CLNCQHNTEG PQCNKCKAGF FGDAMKATAT SCRPCPCPYI DASRRFSDTC FLDTDGQATC   840
DACAPGYTGR RCESCAPGYE GNPIQPGGKC RPVNQEIVRC DERGSMGTSG EACRCKNNVV   900
GRLCNECADG SFHLSTRNPD GCLKCFCMGV SRHCTSSSWS RAQLHGASEE PGHFSLTNAA   960
STHTTNEGIF SPTPGELGFS SFHRLLSGPY FWSLPSRFLG DKVTSYGGEL RFTVTQRSQP  1020
GSTPLHGQPL VVLQGNNIIL EHHVAQEPSP GQPSTFIVPF REQAWQRPDG QPATREHLLM  1080
ALAGIDTLLI RASYAQQPAE SRVSGISMDV AVPEETGQDP ALEVEQCSCP PGYRGPSCQD  1140
CDTGYTRTPS GLYLGTCERC SCHGHSEACE PETGACQGCQ HHTEGPRCEQ CQPGYYGDAQ  1200
RGTPQDCQLC PCYGDPAAGQ AAHTCFLDTD GHPTCDACSP GHSGRHCERC APGYYGNPSQ  1260
GQPCQRDSQV PGPIGCNCDP QGSVSSQCDA AGQCQCKAQV EGLTCSHCRP HHFHLSASNP  1320
DGCLPCFCMG ITQQCASSAY TRHLISTHFA PGDFQGFALV NPQRNSRLTG EFTVEPVPEG  1380
AQLSFGNFAQ LGHESFYWQL PETYQGDKVA AYGGKLRYTL SYTAGPQGSP LSDPDVQITG  1440
NNIMLVASQP ALQGPERRSY EIMFREEFWR RPDGQPATRE HLLMALADLD ELLIRATFSS  1500
VPLAASISAV SLEVAQPGPS NRPRALEVEE CRCPPGYIGL SCQDCAPGYT RTGSGLYLGH  1560
CELCECNGHS DLCHPETGAC SQCQHNAAGE FCELCAPGYY GDATAGTPED CQPCACPLTN  1620
PENMFSRTCE SLGAGGYRCT ACEPGYTGQY CEQCGPGYVG NPSVQGGQCL PETNQAPLVV  1680
EVHPARSIVP QGGSHSLRCQ VSGSPPHYFY WSREDGRPVP SGTQQRHQGS ELHFPSVQPS  1740
DAGVYICTCR NLHQSNTSRA ELLVTEAPSK PITVTVEEQR SQSVRPGADV TFICTAKSKS  1800
PAYTLVWTRL HNGKLPTRAM DFNGILTIRN VQLSDAGTYV CTGSNMFAMD QGTATLHVQA  1860
SGTLSAPVVS IHPPQLTVQP GQLAEFRCSA TGSPTPTLEW TGGPGGQLPA KAQIHGGILR  1920
LPAVEPTDQA QYLCRAHSSA GQQVARAVLH VHGGGGPRVQ VSPERTQVHA GRTVRLYCRA  1980
AGVPSATITW RKEGGSLPPQ ARSERTDIAT LLIPAITTAD AGFYLCVATS PAGTAQARIQ  2040
VVVLSASDAS PPPVKIESSS PSVTEGQTLD LNCVVAGSAH AQVTWYRRGG SLPPHTQVHG  2100
SRLRLPQVSP ADSGEYVCRV ENGSGPKEAS ITVSVLHGTH GSPSYTPVPG STRPIRIEPS  2160
SSHVAEGQTL DLNCVVPGQA HAQVTWHKRG GSLPARHQTH GSLLRLHQVT PADSGEYVCH  2220
VVGTSGPLEA SVLVTIEASV IPGPIPPVRI ESSSSTVAEG QTLDLSCVVA GQAHAQVTWY  2280
KRGGSLPARH QVRGSRLYIF QASPADAGQY VCRASNGMEA SITVTVTGTQ GANLAYPAGS  2340
TQPIRIEPSS SQVAEGQTLD LNCVVPGQSH AQVTWHKRGG SLPVRHQTHG SLLRLYQASP  2400
ADSGEYVCRV LGSSVPLEAS VLVTIEPAGS VPALGVTPTV RIESSSSQVA EGQTLDLNCL  2460
VAGQAHAQVT WHKRGGSLPA RHQVHGSRLR LLQVTPADSG EYVCRVVGSS GTQEASVLVT  2520
IQQRLSGSHS QGVAYPVRIE SSSASLANGH TLDDLNCLVAS QAPHTITWYK RGGSLPSRHQ  2580
IVGSRLRIPQ VTPADSGEYV CHVSNGAGSR ETSLIVTIQG SGSSHVPSVS PPIRIESSSP  2640
TVVEGQTLDL NCVVARQPQA IITWYKRGGS LPSRHQTHGS HLRLHQMSVA DSGEYVCRAN  2700
NNIDALEASI VISVSPSAGS PSAPGSSMPI RIESSSSHVA EGETLDLNCV VPGQAHAQVT  2760
WHKRGGSLPS HHQTRGSRLR LHHVSPADSG EYVCRVMGSS GPLEASVLVT IEASGSSAVH  2820
VPAPGGAPPI RIEPSSSRVA EGQTLDLKCV VPGQAHAQVT WHKRGGNLPA RHQVHGPLLR  2880
LNQVSPADSG EYSCQVTGSS GTLEASVLVT IEPSSPGPIP APGLAQPIYI EASSSHVTEG  2940
QTLDLNCVVP GQAHAQVTWY KRGGSLPARH QTHGSQLRLH LVSPADSGEY VCRAASGPGP  3000
EQEASFTVTV PPSEGSSYRL RSPVISIDPP SSTVQQGQDA SFKCLIHDGA APISLEWKTR  3060
NQELEDNVHI SPNGSIITIV GTRPSNHGTY RCVASNAYGV AQSVVNLSVH GPPTVSVLPE  3120
GPVWVKVGKA VTLECVSAGE PRSSARWTRI SSTPAKLEQR TYGLMDSHAV LQISSAKPSD  3180
AGTYVCLAQN ALGTAQKQVE VIVDTGAMAP GAPQVQAEEA ELTVEAGHTA TLRCSATGSP  3240
APTIHWSKLR SPLPWQHRLE GDTLIIPRVA QQDSGQYICN ATSPAGHAEA TIILHVESPP  3300
YATTVPEHAS VQAGETVQLQ CLAHGTPPLT FQWSRVGSSL PGRATARNEL LHFERAAPED  3360
SGRYRCRVTN KVGSAEAFAQ LLVQGPPGSL PATSIPAGST PTVQVTPQLE TKSIGASVEF  3420
HCAVPSDRGT QLRWFKEGGQ LPPGHSVQDG VLRIQNLDQS CQGTYICQAH GPWGKAQASA  3480
QLVIQALPSV LINIRTSVQT VVVGHAVEFE CLALGDPKPQ VTWSKVGGHL RPGIVQSGGV  3540
VRIAHVELAD AGQYRCTATN AAGTTQSHVL LLVQALPQIS MPQEVRVPAG SAAVFPCIAS  3600
GYPTPDISWS KLDGSLPPDS RLENNMLMLP SVRPQDAGTY VCTATNRQGK VKAFAHLQVP  3660
ERVVPYFTQT PYSFLPLPTI KDAYRKFEIK ITFRPDSADG MLLYNGQKRV PGSPTNLANR  3720
QPDFISFGLV GGRPEFRFDA GSGMATIRHP TPLALGHFHT VTLLRSLTQG SLIVGDLAPV  3780
NGTSQGKFQG LDLNEELYLG GYPDYGAIPK AGLSSGFIGC VRELRIQGEE IVFHDLNLTA  3840
HGISHCPTCR DRPCQNGGQC HDSESSSYVC VCPAGFTGSR CEHSQALHCH PEACGPDATC  3900
VNRPDGRGYT CRCHLGRSGL RCEEGVTVTT PSLSGAGSYL ALPALTNTHH ELRLDVEFKP  3960
LAPDGVLLFS GGKSGPVEDF VSLAMVGGHL EFRYELGSGL AVLRSAEPLA LGRWHRVSAE  4020
RLNKDGSLRV NGGRPVLRSS PGKSQGLNLH TLLYLGGVEP SVPLSPATNM SAHFRGCVGE  4080
VSVNGKRLDL TYSFLGSQGI GQCYDSSPCE RQPCQHGATC MPAGEYEFQC LCRDGFKGDL  4140
CEHEENPCQL REPCLHGGTC QGTRCLCLPG FSGPRCQQGS GHGIAESDWH LEGSGGNDAP  4200
GQYGAYFHDD GFLAFPGHVF SRSLPEVPET IELEVRTSTA SLLLWQGVE VGEAGQGKDF  4260
ISLGLQDGHL VFRYQLGSGE ARLVSEDPIN DGEWHRVTAL REGRRGSIQV DGEELVSGRS  4320
PGPNVAVNAK GSVYIGGAPD VATLTGGRFS SGITGCVKNL VLHSARPGAP PPQPLDLQHR  4380
AQAGANTRPC PS                                                     4392

SEQ ID NO: 2        moltype = AA  length = 4391
FEATURE             Location/Qualifiers
```

-continued

```
source                1..4391
                      mol_type = protein
                      organism = Homo sapiens
SEQUENCE: 2
MGWRAAGALL LALLLHGRLL AVTHGLRAYD GLSLPEDIET VTASQMRWTH SYLSDDEDML   60
ADSISGDDLG SGDLGSGDFQ MVYFRALVNF TRSIEYSPQL EDAGSREFRE VSEAVVDTLE   120
SEYLKIPGDQ VVSVVFIKEL DGWVFVELDV GSEGNADGAQ IQEMLLRVIS SGSVASYVTS   180
PQGFQFRRLG TVPQFPPRACT EAEFACHSYN ECVALEYRCD RRPDCRDMSD ELNCEEPVLG   240
ISPTFSLLVE TTSLPPRPET TIMRQPPVTH APQPLLPGVS RPLPCGPQEA ACRNGHCIPR   300
DYLCDGQEDC EDGSDELDCG PPPPCEPNEF PCGNGHCALK LWRCDGDFDC EDRTDEANCP   360
TKRPEEVCGP TQFRCVSTNM CIPASFHCDE ESDCPDRSDE FGCMPPQVVT PPRESIQASR   420
GQTVTFTCVA IGVPTPIINW RLNWGHIPSH PRVTVTSEGG RGTLIIRDVK ESDQGAYTCE   480
AMNARGMVFG IPDGVLELVP QRGPCPDGHF YLEHSAACLP CFCFGITSVC QSTRRFRDQI   540
RLRFDQPDDF KGVNVTMPAQ PGTPPLSSTQ LQIDPSLHEF QLVDLSRRFL VHDSFWALPE   600
QPFLGNKVDSY GGSLRYNVRY ELARGMLEPV QRPDVVLMGA GYRLLSRGHT PTQPGALNQR   660
QVQFSEEHWV HESGRPVQRA ELLQVLQSLE AVLIQTVYNT KMASVGLSDI AMDTTVTHAT   720
SHGRAHSVEE CRCPIGYSGL SCESCDAHFT RVPGGPYLGT CSGCNCNGHA SSCDPVYGHC   780
LNCQHNTEGP QCNKCKAGFF GDAMKATATS CRPCPCPYID ASRRFSDTCF LDTDGQATCD   840
ACAPGYTGRR CESCAPGYEG NPIQPGGKCR PVNQEIVRCD ERGSMGTSGE ACRCKNNVVG   900
RLCNECADGS FHLSTRNPDG CLKCFCMGVS RHCTSSSWSR AQLHGASEEP GHFSLTNAAS   960
THTTNEGIFS PTPGELGFSS FHRLLSGPYF WSLPSRFLGD KVTSYGGELR FTVTQRSQPG   1020
STPLHGQPLV VLQGNNIILE HHVAQEPSPG QPSTFIVPFR EQAWQRPDGQ PATREHLLMA   1080
LAGIDTLLIR ASYAQQPAES RVSGISMDVA VPEETGQDPA LEVEQCSCPP GYRGPSCQDC   1140
DTGYTRTPSG LYLGTCERCS CHGHSEACEP ETGACQGCQH HTEGPRCEQC QPGYYGDAQR   1200
GTPQDCQLCP CYGDPAAGQA AHTCFLDTDG HPTCDACSPG HSGRHCERCA PGYYGNPSQG   1260
QPCQRDSQVP GPIGCNCDPQ GSVSSQCDAA GQCQCKAQVE GLTCSHCRPH HFHLSASNPD   1320
GCLPCFCMGI TQQCASSAYT RHLISTHFAP GDFQGFALVN PQRNSRLTGE FTVPEVPEGA   1380
QLSFGNFAQL GHESFYWQLP ETYQGDKVAA YGGKLRYTLS YTAGPQGSPL SDPDVQITGN   1440
NIMLVASQPA LQGPERRSYE IMFREEFWRR PDGQPATREH LLMALADLDE LLIRATFSSV   1500
PLAASISAVS LEVAQPGPSN RPRALEVEEC RCPPGYIGLS CQDCAPGYTR TGSGLYLGHC   1560
ELCECNGHSD LCHPETGACS QCQHNAAGEF CELCAPGYYG DATAGTPEDC QPCACPLTNP   1620
ENMFSRTCES LGAGGYRCTA CEPGYTGQYC EQCGPGYVGN PSVQGGQCLP ETNQAPLVVE   1680
VHPARSIVPQ GGSHSLRCQV SGSPPHYFYW SREDGRPVPS GTQQRHQGSE LHFPSVQPSD   1740
AGVYICTCRN LHQSNTSRAE LLVTEAPSKP ITVTVEEQRS QSVRPGADVT FICTAKSKSP   1800
AYTLVWTRLH NGKLPTRAMD FNGILTIRNV QLSDAGTYVC TGSNMFAMDQ GTATLHVQAS   1860
GTLSAPVVSI HPPQLTVQPG QLAEFRCSAT GSPTPTLEWT GGPGGQLPAK AQIHGGILRL   1920
PAVEPTDQAQ YLCRAHSSAG QQVARAVLHV HGGGGPRVQV SPERTQVHAG RTVRLYCRAA   1980
GVPSATITWR KEGGSLPPQA RSERTDIATL LIPAITTADA GFYLCVATSP AGTAQARIQV   2040
VVLSASDASP PPVKIESSSP SVTEGQTLDL NCVVAGSAHA QVTWYRRGGS LPPHTQVHGS   2100
RLRLPQVSPA DSGEYVCRVE NGSGPKEASI TVSVLHGTHS GPSYTPVPGS TRPIRIEPSS   2160
SHVAEGQTLD LNCVVPGQAH AQVTWHKRGG SLPARHQTHG SLLRLHQVTP ADSGEYVCHV   2220
VGTSGPLEAS VLVTIEASVI PGPIPPVRIE SSSSTVAEGQ TLDLSCVVAG QAHAQVTWYK   2280
RGGSLPARHQ VRGSRLYIFQ ASPADAGQYV CRASNGMEAS ITVTVTGTGQ ANLAYPAGST   2340
QPIRIEPSSS QVAEGQTLDL NCVVPGQSHA QVTWHKRGGS LPVRHQTHGS LLRLYQASPA   2400
DSGEYVCRVL GSSVPLEASV LVTIEPAGSV PALGVTPTVR IESSSSQVAE GQTLDLNCLV   2460
AGQAHAQVTW HKRGGSLPAR HQVHGSRLRL LQVTPADSGE YVCRVVGSSG TQEASVLVTI   2520
QQRLSGSHSQ GVAYPVRIES SSASLANGHT LDLNCLVASQ APHTITWYKR GGSLPSRHQI   2580
VGSRLRIPQV TPADSGEYVC HVSNGAGSRE TSLIVTIQGS GSSHVPSVSP PIRIESSSPT   2640
VVEGQTLDLN CVVARQPQAI ITWYKRGGSL PSRHQTHGSH LRLHQMSVAD SGEYVCRANN   2700
NIDALEASIV ISVSPSAGSP SAPGSSMPIR IESSSRVAEG ETLDLNCVV PGQAHAQVTW   2760
HKRGGSLPSH HQTRGSRLRL HHVSPADSGE YVCRVMGSSG PLEASVLVTI EASGSSAHVV   2820
PAPGGAPPIR IEPSSSRVAE GQTLDLKCVV PGQAHAQVTW HKRGGNLPAR HQVHGPLLRL   2880
NQVSPADSGE YSCQVTGSSG TLEASVLVTI EPSSPGPIPA PGLAQPIYIE ASSSHVTEGQ   2940
TLDLNCVVPG QAHAQVTWYK RGGSLPARHQ THGSQLRLHL VSPADSGEYV CRAASGPGPE   3000
QEASFTVTVP PSEGSSYRLR SPVISIDPPS STVQQGQDAS FKCLIHDGAA PISLEWKTRN   3060
QELEDNVHIS PNGSIITIVG TRPSNHGTYR CVASNAYGVA QSVVNLSVHG PPTVSVLPEG   3120
PVWVKVGKAV TLECVSAGEP RSSARWTRIS STPAKLEQRT YGLMDSHAVL QISSAKPSDA   3180
GTYVCLAQNA LGTAQKQVEV IVDTGAMAPG APQVQAEEAE LTVEAGHTAT LRCSATGSPA   3240
PTIHWSKLRS PLPWQHRLEG DTLIIPRVAQ QDSGQYICNA TSPAGHAEAT IILHVESPPY   3300
ATTVPEHASV QAGETVQLQC LAHGTPPLTF QWSRVGSSLP GRATARNELL HFERAAPEDS   3360
GRYRCRVTNK VGSAEAFAQL LVQGPPGSLP ATSIPAGSTP TVQVTPQLET KSIGASVEFH   3420
CAVPSDRGTQ LRWFKEGGQL PPGHSVQDGV LRIQNLDQSC QGTYICQAHG PWGKAQASAQ   3480
LVIQALPSVL INIRTSVQTV VVGHAVEFEC LALGDPKPQV TWSKVGGHLR PGIVQSGGVS   3540
RIAHVELADA GQYRCTATNA AGTTQSHVLL LVQALPQISM PQEVRVPAGS AAVFPCIASG   3600
YPTPDISWSK LDGSLPPDSR LENNMLMLPS VRPQDAGTYV CTATNRQGKV KAFAHLQVPE   3660
RVVPYFTQTP YSFLPLPTIK DAYRKFEIKI TFRPDSADGM LLYNGQKRVP GSPTNLANRQ   3720
PDFISFGLVG GRPEFRFDAG SGMATIRHPT PLALGHFHTV TLLRSLTQGS LIVGDLAPVN   3780
GTSQGKFQGL DLNEELYLGG YPDYGAIPKA GLSSGFIGCV RELRIQGEEI VFHDLNLTAH   3840
GISHCPTCRD RPCQNGGQCH DSESSSYVCV CPAGFTGSRC EHSQALHCHP EACGPDATCV   3900
NRPDGRGYTC RCHLGRSGLR CEEGVTVTTP SLSGAGSYLA LPALTNTHHE LRLDVEFKPL   3960
APDGVLLFSG GKSGPVEDFV SLAMVGGHLE FRYELGSGLA VLRSAEPLAL GRWHRVSAER   4020
LNKDGSLRVN GGRPVLRSSP GKSQGLNLHT LLYLGGVEPS VPLSPATNMS AHFRGCVGEV   4080
SVNGKRLDLT YSFLGSQGIG QCYDSSPCER QPCQHGATCM PAGEYEFQCL CRDGFKGDLC   4140
EHEENPCQLR EPCLHGGTCQ GTRCLCLPGF SGPRCQQGSG HGIAESDWHL EGSGGNDAPG   4200
QYGAYFHDDG FLAFPGHVFS RSLPEVPETI ELEVRTSTAS GLLLWQGVEV GEAGQGKDFI   4260
SLGLQDGHLV FRYQLGSGEA RLVSEDPIND GEWHRVTALR EGRRGSIQVD GEELVSGRSP   4320
GPNVAVNAKG SVYIGGAPDV ATLTGGRFSS GITGCVKNLV LHSARPGAPP PQPLDLQHRA   4380
QAGANTRPCP S                                                         4391
```

```
SEQ ID NO: 3             moltype = AA   length = 4383
FEATURE                  Location/Qualifiers
source                   1..4383
                         mol_type = protein
                         organism = Mus musculus
SEQUENCE: 3
MGQRAVGSLL LGLLLHARLL AVTHGLRAYD GLSLPEDTET VTASRYGWTY SYLSDDEDLL  60
ADDASGDGLG SGDVGSGDFQ MVYFRALVNF TRSIEYSPQL EDASAKEFRE VSEAVVEKLE  120
PEYRKIPGDQ IVSVVFIKEL DGWVPVELDV GSEGNADGSQ IQEVLHTVVS SGSIGPYVTS  180
PWGFKFRRLG TVPQFPRVCT ETEFACHSYN ECVALEYRCD RRPDCRDMSD ELNCEEPVPE  240
LSSSTPAVGK VSPLPLWPEA ATTPPPPVTH GPQFLLPSVP GPSACGPQEA SCHSGHCIPR  300
DYLCDGQEDC RDGSDELGCA SPPPCEPNEF ACENGHCALK LWRCDGDFDC EDRTDEANCS  360
VKQPGEVCGP THFQCVSTNR CIPASFHCDE ESDCPDRSDE FGCMPPQVVT PPQQSIQASR  420
GQTVTFTCVA TGVPTPIINW RLNWGHIPAH PRVTMTSEGG RGTLIIRDVK EADQGAYTCE  480
AMNSRGMVFG IPDGVLELVP QRGPCPDGHF YLEDSASCLP CFCFGVTNVC QSSLRFRDQI  540
RLSFDQPNDF KGVNVTMPSQ PGVPPLSSTQ LQIDPALQEF QLVDLSRRFL VHDAFWALPK  600
QFLGNKVDSY GGFLRYKVRY ELARGMLEPV QKPDVILVGA GYRLHSRGHT PTHPGTLNQR  660
QVQLSEEHWV HESGRPVQRA EMLQALASLE AVLLQTVYNT KMASVGLSDI VMDTTVTHTT  720
IHGRAHSVEE CRCPIGYSGL SCESCDAHFT RVPGGPYLGT CSGCNCNGHA SSCDPVYGHC  780
LNCQHNTEGP QCDKCKPGFF GDATKATATA CRPCPCPYID ASRRFSDTCF LDTDGQATCD  840
ACAPGYTGRR CESCAPGYEG NPIQPGGKCR PTTQEIVRCD ERGSLGTSGE TCRCKNNVVG  900
RLCNECSDGS FHLSKQNPDG CLKCFCMGVS RQCSSSSWSR AQVLGASEQP SQFSLSNAAG  960
THTTSEGVSS PAPGELSFSS FHNLLSEPYF WSLPASFRGD KVTSYGGELR FTVTQRPRPS  1020
SAPLHRQPLV VLQGNNIVLE HHASRDPSPG QPSNFIVPFQ EQAWQRPDGQ PATREHLLMA  1080
LAGIDALLIQ ASYTQQPAES RVSGISMDVA VPENTGQDSA REVEQCTCPP GYRGPSCQDC  1140
DTGYTRVPSG LYLGTCERCN CHGHSETCEP ETGACQSCQH HTEGASCEQC QPGYYGDAQR  1200
GTPQDCQPCP CYGAPAAGQA AHTCFLDTDG HPTCDSCSPG HSGRHCERCA PGYYGNPSQG  1260
QPCHRDGQVP EVLGCGCDPH GSISSQCDAA GQCQCKAQVE GRTCSHCRPH HFHLSASNPE  1320
GCLPCFCMGV TQQCASSSYS RQLISTHFAP GDFQGFALVN PQRNSQLTGG FTVEPVHDGA  1380
RLSFSNFAHL GQESFYWQLP EIYQGDKVAA YGGKLRYTLS YTAGPQGSPL LDPDIQITGN  1440
NIMLVASQPA LQGPERRSYE IIFREEFWRR PDGQPATREH LLMALADLDE LLVRATFSSV  1500
PRAASISAVS LEVAQPGPSS GPRALEVEEC RCPPGYVGLS CQDCAPGYTR TGSGLYLGQC  1560
ELCECNGHSD LCHPETGACS RCQHNTAGEF CELCATGYYG DATAGTPEDC QPCACPLTNP  1620
ENMFSRTCES LGAGGYRCTA CEPGYTGQYC EQCAPGYEQD PNVQGGRCQP LTKESLEVQI  1680
HPSRSVVPQG GPHSLRCQVS GSPPHYFYWS REDGRPLPSS AQQRHQGSEL HFPSVQPSDA  1740
GVYICTCRNL IHTSNSRAEL LVAEAPSKPI TVTVEEQRSQ SVRPGADVTF ICTAKSKSPA  1800
YTLVVWTRLHN GKLPSRAMDF NGILTIRNVQ PSDAGTYVCT GSNMFAMDQG TATLHVQVSG  1860
TSTAPVASIH PPQLTVQPGQ QAEFRCSATG NPTPMLEWIG GPSGQLPAKA QIHNGILRLP  1920
AIEPSDQGQY LCRALSSAGQ HVARAMLQVH GGSGPRVQVS PERTQVHEGR TVRLYCRAAG  1980
VPSASITWRK EGGSLPPQAR SENTDIPTLL IPAITAADAG FYLCVATSPT GTAQARIQVV  2040
VLSASGANSV PVRIESSSPS VTEGQTLDLN CAVMGLTYTQ VTWYKRGGSL PPHAQVHGSR  2100
LRLPQVSPAD SGDYVCRVES DVGPKEASIV VSVLHSPHSG PSYTPATSIT PPIRIESSSS  2160
HVAEGQTLDL NCVVPGQAQV TWRKRGGSLP ARHQTHGSLL RLHQVSPADS GEYVCHVVLG  2220
SEHTETSVLV TIEPAESIPA PGPAPPVRIE ASSSTVTEGH MLDLNCVVAG QAHAQVTWYK  2280
RGGSLPARHQ VRGSRLYILQ ASPADAGEYV CRAGNGQEAT ITVTVTRNHG ANLAYPPGST  2340
SPIRIESSSS HVAEGQTLDL NCVVQGQAHA QVTWHKRGGS LPARHQTHGS LLRLHQVSPV  2400
DSGEYVCRVE GGAVPLESSV LVTIEPAGTA PGVIPPVRIE SSSSHVSEGQ SLDLNCLVSG  2460
QTHPQISWHK RGGSLPARHQ VHGSRLRLLQ VTPTDSGEYV CRVVSGSGTQ EASILVTIQQ  2520
TLSPSHSQSV VHPVRIESSS PSLANGHTLD LNCLVASLTP HTITWYKRGG SLPSRHQIVG  2580
SRLRIPQVTP ADSGEYVCHV SNGAGSQETS LIVTIESRGP SHVPSVSPPM RIETSSPTVT  2640
EGQTLDLNCV VVGRPQATIT WYKRGGSLPF RHQAHGSRLR LHHMSVADSG EYVCRANNNI  2700
DAQETSIMIS VSPSTNSPPA PASPAPIRIE SSSSRVAEGQ TLDLNCVVPG HAHAQVTWHK  2760
RGGSLPTHHQ THGSRLRLYQ VSSADSGEYV CSVLSSSGPL EASVLVSITP AAANVHIPGE  2820
VPFPPIRIET SSSRVAEGQT LDLSCVVPGQ AHAQVTWHKR GGSLPAGHQV HGHMLRLNRV  2880
SPADSGEYSC QVTGSSGTLE ASVLVTIEAS EPSPIPAPGL AQPVYIESSS SHLTEGQTVD  2940
LKCVVPGQAH AQVTWHKRGS SLPARHQTHG SLLRLYQLSP ADSGEYVCQV AGSSHPEHEA  3000
SPKLTVPSSQ NSSFRLRSPV ISIEPPSSTV QQGQDASFKC LIHEGATPIK VEWKIRDQEL  3060
EDNVHISPNG SIITIVGTRP SNHGAYRCVA SNVYGMAQSV VNLSVHGPPT VSVLPEGPVH  3120
VKMGKDITLE CISSGEPRSS PRWTRLGIPV KLEPRMFGLM NSHAMLKIAS VKPSDAGTYV  3180
CQAQNALGTA QKQVELIVDT GTVAPGAPQV QVEESELTLE AGHTATLHCS ATGNPPPTIH  3240
WSKLRAPLPW QHRIEGNTLV IPRVAQQDSG QYICNATNSA GHTEATVVLH VESPPYATII  3300
PEHTSAQPGN LVQLQCLAHG TPPLTYQWSL VGGVLPEKAV ARNQVLRLEP TVPEDSGRYR  3360
CQVSNRVGSA EAFAQVLVQG SSSNLPDTSI PGGSTPTVQV TPQLETRNIG ASVEFHCAVP  3420
NERGTHLRWL KEGGQLPPGH SVQDGVLRIQ NLDQSCQGTY VCQAHGPWGQ AQATAQLIVQ  3480
ALPSVLINVR TSVHSVVVGH SVEFECLALG DPKPQVTWSK VGGHLRPGIV QSGSIIRIAH  3540
VELADAGQYR CAATNAAGTT QSHVLLLVQA LPQISTPPEI RVPAGSAAVF PCMASGYPTP  3600
AITWSKVDGD LPPDSRLENN MLMLPSVRPE DAGTYVCTAT NRQGKVKAFA YLQVPERVIP  3660
YFTQTPYSFL PLPTIKDAYR KFEIKITFRP DSADGMLLYN GQKRSPTNLA NRQPDFISFG  3720
LVGGRPEFRF DAGSGMATIR HPTPLALGQF HTVTLLRSLT QGSLIVGNLA PVNGTSQGKF  3780
QGLDLNEELY LGGYPDYGAI PKAGLSSGFV GCVRELRIQG EEVVFHDVNL TTHGISHCPT  3840
CQDRPCQNGG QCQDSESSSY TCVCPAGFTG SRCEHSQALH CHPEACGPDA TCVNRPDGRG  3900
YTCRCHLGRS GVRCEEGVTV TTPSMSGAGS YLALPALTNM HHELRLDVEF KPLEPNGILL  3960
FSGGKSGPVE DFVSLAMVGG HLEFRYELGS GLAVLRSHEP LTLGRWHRVS AERLNKDGSL  4020
RVDGGRPVLR SSPGKSQGLN LHTLLYLGGV EPSVQLSPAT NMSAHFHGCV GEVSVNGKRL  4080
DLTYSFLGSQ GVGQCYDSSP CERQPCQNGA TCMPAGEYEF QCLCQDGFKG DLCEHEENPC  4140
QLHEPCLNGG TCRGARCLCL PGFSGPRCQQ GAGYGVVESD WHPEGSGGND APGQYGAYFY  4200
DNGFLGLPGN SFSRSLPEVP ETIEFEVRTS TADGLLLWQG VVREASRSKD FISLGLQDGH  4260
LVFSYQLGSG EARLVSEDPI NDGEWHRITA LREGQRGSIQ VDGEDLVTGR SPGPNVAVNT  4320
KDIIYIGGAP DVATLTRGKF SSGITGCIKN LVLHTARPGA PPPQPLDLQH RAQAGANTRP  4380
```

-continued

```
CPS                                                                        4383

SEQ ID NO: 4              moltype = AA  length = 2068
FEATURE                   Location/Qualifiers
source                    1..2068
                          mol_type = protein
                          organism = Homo sapiens
SEQUENCE: 4
MAGRSHPGPL RPLLPLLVVA ACVLPGAGGT CPERALERRE EEANVVLTGT VEEILNVDPV    60
QHTYSCKVRV WRYLKGKDLV ARESLLDGGN KVVISGFGDP LICDNQVSTG DTRIFFVNPA   120
PPYLWPAHKN ELMLNSSLMR ITLRNLEEVE FCVEDKPGTH FTPVPPTPPD ACRGMLCGFG   180
AVCEPNAEGP GRASCVCKKS PCPSVVAPVC GSDASTYSNE CELQRAQCSQ QRRIRLLSRG   240
PCGSRDPCSN VTCSFGSTCA RSADGLTASC LCPATCRGAP EGTVCGSDGA DYPGECQLLR   300
RACARQENVF KKFDGPCDPC QGALPDPSRS CRVNPRTRRP EMLLRPESCP ARQAPVCGDD   360
GVTYENDCVM GRSGAARGLL LQKVRSGQCQ GRDQCPEPCR FNAVCLSRRG RPRCSCDRVT   420
CDGAYRPVCA QDGRTYDSDC WRQQAECRQQ RAIPSKHQGP CDQAPSPCLG VQCAFGATCA   480
VKNGQAACEC LQACSSLYDP VCGSDGVTYG SACELEATAC TLGREIQVAR KGPCDRCGQC   540
RFGALCEAET GRCVCPSECV ALAQPVCGSD GHTYPSECML HVHACTHQIS LHVASAGPCE   600
TCGDAVCAFG AVCSAGQCVC PRCEHPPPGP VCGSDGVTYG SACELREAAC LQQTQIEEAR   660
AGPCEQAECG SGGSGSGEDG DCEQELCRQR GGIWDEDSED GPCVCDFSCQ SVPGSPVCGS   720
DGVTYSTECE LKKARCESQR GLYVAAQGAC RGPTFAPLPP VAPLHCAQTP YGCCQDNITA   780
ARGVGLAGCP SACQCNPHGS YGGTCDPATG QCSCRPGVGG LRCDRCEPGF WNFRGIVTDG   840
RSGCTPCSCD PQGAVRDDCE QMTGLCSCKP GVAGPKCGQC PDGRALGPAG CEADASAPAT   900
CAEMRCEFGA RCVEESGSAH CVCPMLTCPE ANATKVCGSD GVTYGNECQL KTIACRQGLQ   960
ISIQSLGPCQ EAVAPSTHPT SASVTVTTPG LLLSQALPAP PGALPLAPSS TAHSQTTPPP  1020
SSRPRTTASV PRTTVWPVLT VPPTAPSPAP SLVASAFGES GSTDGSSDEE LSGDQEASGG  1080
GSGGLEPLEG SSVATPGPPV ERASCYNSAL GCCSDGKTPS LDAEGSNCPA TKVFQGVLEL  1140
EGVEGQELFY TPEMADPKSE LFGETARSIE STLDDLFRNS DVKKDFRSVR LRDLGPGKSV  1200
RAIVDVHFDP TTAFRAPDVA RALLRQIQVS RRRSLGVRRP LQEHVRFMDF DWFPAFITGA  1260
TSGAIAAGAT ARATTASRLP SSAVTPRAPH PSHTSQPVAH TTAAPTTRRP PTTAPSRVPG  1320
RRPPAPQQPP KPCDSQPCFH GGTCQDWALG GGFTCSCPAG RGGAVCEKVL GAPVPAFEGR  1380
SFLAFPTLRA YHTLRLALEF RALEPQGLLL YNGNARGKDF LALALLDGRV QLRFDTGSGP  1440
AVLTSAVPVE PGQWHRLELS RHWRRGTLSV DGETPVLGES PSGTDGLNLD TDLFVGGVPE  1500
DQAAVALERT FVGAGLRGCI RLLLDVNNQRL ELGIGPGAAT RGSGVGECGD HPCLPNPCHG  1560
GAPCQNLEAG RFHCQCPPGR VGPTCADEKS PCQPNPCHGA APCRVLPEGG AQCECPLGRE  1620
GTFCQTASGQ DGSGPPLADF NGFSHLELRG LHTFARDLGE KMALEVVFLA RGPSGLLLYN  1680
GQKTDGKGDF VSLALRDRRL EFRYDLGKGA AVIRSREPVT LGAWTRVSLE RNGRKGALRV  1740
GDGPRVLGES PKSRKVPHTV LNLKEPLYVG GAPDFSKLAR AAAVSSGFDG AIQLVSLGGR  1800
QLLTPEHVLR QVDVTSFAGH PCTRASGHPC LNGASCVPRE AAYVCLCPGG FSGPHCEKGL  1860
VEKSAGDVDT LAFDGRTFVE YLNAVTESEL ANEIPVPETL DSGALHSEKA LQSNHFELSL  1920
RTEATQGLVL WSGKATERAD YVALAIVDGH LQLSYNLGSQ PVVLRSTVPV NTNRWLRVVA  1980
HREQREGSLQ VGNEAPVTGS SPLGATQLDT DGALWLGGLP ELPVGPALPK AYGTGFVGCL  2040
RDVVVGRHPL HLLEDAVTKP ELRPCPTP                                     2068

SEQ ID NO: 5              moltype = AA  length = 2045
FEATURE                   Location/Qualifiers
source                    1..2045
                          mol_type = protein
                          organism = Homo sapiens
SEQUENCE: 5
MAGRSHPGPL RPLLPLLVVA ACVLPGAGGT CPERALERRE EEANVVLTGT VEEILNVDPV    60
QHTYSCKVRV WRYLKGKDLV ARESLLDGGN KVVISGFGDP LICDNQVSTG DTRIFFVNPA   120
PPYLWPAHKN ELMLNSSLMR ITLRNLEEVE FCVEDKPGTH FTPVPPTPPD ACRGMLCGFG   180
AVCEPNAEGP GRASCVCKKS PCPSVVAPVC GSDASTYSNE CELQRAQCSQ QRRIRLLSRG   240
PCGSRDPCSN VTCSFGSTCA RSADGLTASC LCPATCRGAP EGTVCGSDGA DYPGECQLLR   300
RACARQENVF KKFDGPCDPC QGALPDPSRS CRVNPRTRRP EMLLRPESCP ARQAPVCGDD   360
GVTYENDCVM GRSGAARGLL LQKVRSGQCQ GRDQCPEPCR FNAVCLSRRG RPRCSCDRVT   420
CDGAYRPVCA QDGRTYDSDC WRQQAECRQQ RAIPSKHQGP CDQAPSPCLG VQCAFGATCA   480
VKNGQAACEC LQACSSLYDP VCGSDGVTYG SACELEATAC TLGREIQVAR KGPCDRCGQC   540
RFGALCEAET GRCVCPSECV ALAQPVCGSD GHTYPSECML HVHACTHQIS LHVASAGPCE   600
TCGDAVCAFG AVCSAGQCVC PRCEHPPPGP VCGSDGVTYG SACELREAAC LQQTQIEEAR   660
AGPCEQAECG SGGSGSGEDG DCEQELCRQR GGIWDEDSED GPCVCDFSCQ SVPGSPVCGS   720
DGVTYSTECE LKKARCESQR GLYVAAQGAC RGPTFAPLPP VAPLHCAQTP YGCCQDNITA   780
ARGVGLAGCP SACQCNPHGS YGGTCDPATG QCSCRPGVGG LRCDRCEPGF WNFRGIVTDG   840
RSGCTPCSCD PQGAVRDDCE QMTGLCSCKP GVAGPKCGQC PDGRALGPAG CEADASAPAT   900
CAEMRCEFGA RCVEESGSAH CVCPMLTCPE ANATKVCGSD GVTYGNECQL KTIACRQGLQ   960
ISIQSLGPCQ EAVAPSTHPT SASVTVTTPG LLLSQALPAP PGALPLAPSS TAHSQTTPPP  1020
SSRPRTTASV PRTTVWPVLT VPPTAPSPAP SLVASAFGES GSTDGSSDEE LSGDQEASGG  1080
GSGGLEPLEG SSVATPGPPV ERASCYNSAL GCCSDGKTPS LDAEGSNCPA TKVFQGVLEL  1140
EGVEGQELFY TPEMADPKSE LFGETARSIE STLDDLFRNS DVKKDFRSVR LRDLGPGKSV  1200
RAIVDVHFDP TTAFRAPDVA RALLRQIQVS RRRSLGVRRP LQEHVRFMDF DWFPAFITGA  1260
TSGAIAAGAT ARATTASRLP SSAVTPRAPH PSHTSQPVAK TTAAPTTRRP PTTAPSRVPG  1320
RRPPAPQQPP KPCDSQPCFH GGTCQDWALG GGFTCSCPAG RGGAVCEKVL GAPVPAFEGR  1380
SFLAFPTLRA YHTLRLALEF RALEPQGLLL YNGNARGKDF LALALLDGRV QLRFDTGSGP  1440
AVLTSAVPVE PGQWHRLELS RHWRRGTLSV DGETPVLGES PSGTDGLNLD TDLFVGGVPE  1500
DQAAVALERT FVGAGLRGCI RLLLDVNNQRL ELGIGPGAAT RGSGVGECGD HPCLPNPCHG  1560
GAPCQNLEAG RFHCQCPPGR VGPTCADEKS PCQPNPCHGA APCRVLPEGG AQCECPLGRE  1620
GTFCQTASGQ DGSGPPLADF NGFSHLELRG LHTFARDLGE KMALEVVFLA RGPSGLLLYN  1680
GQKTDGKGDF VSLALRDRRL EFRYDLGKGA AVIRSREPVT LGAWTRVSLE RNGRKGALRV  1740
```

```
GDGPRVLGES PVPHTVLNLK EPLYVGGAPD FSKLARAAAV SSGFDGAIQL VSLGGRQLLT    1800
PEHVLRQVDV TSFAGHPCTR ASGHPCLNGA SCVPREAAYV CLCPGGFSGP HCEKGLVEKS    1860
AGDVDTLAFD GRTFVEYLNA VTESEKALQS NHFELSLRTE ATQGLVLWSG KATERADYVA    1920
LAIVDGHLQL SYNLGSQPVV LRSTVPVNTN RWLRVVAHRE QREGSLQVGN EAPVTGSSPL    1980
GATQLDTDGA LWLGGLPELP VGPALPKAYG TGFVGCLRDV VVGRHPLHLL EDAVTKPELR    2040
PCPTP                                                                2045

SEQ ID NO: 6            moltype = AA  length = 1940
FEATURE                 Location/Qualifiers
source                  1..1940
                        mol_type = protein
                        organism = Rattus norvegicus
SEQUENCE: 6
MPPLPLEHRP RQEPGASMLV RYFMIPCNIC LILLATSTLG FAVLLFLSNY KPGIHFTPAP    60
PTPPDVCRGM LCGFGAVCEP SVEDPGRASC VCKKNACPAT VAPVCGSDAS TYSNECELQR    120
AQCNQQRRIR LLRQGPCGSR DPCANVTCSF GSTCVPSADG QTASCLCPTT CFGAPDGTVC    180
GSDGVDYPSE CQLLSHACAS QEHIFKKFNG PCDPCQGSMS DLNHICRVNP RTRHPEMLLR    240
PENCPAQHTP ICGDDGVTYE NDCVMSRIGA TRGLLLQKVR SGQCQTRDQC PETCQFNSVC    300
LSRRGRPHCS CDRVTCDGSY RPVCAQDGHT YNNDCWRQQA ECRQQRAIPP KHQGPCDQTP    360
SPCHGVQCAF GAVCTVKNGK AECECQRVCS GIYDPVCGSD GVTYGSVCEL ESMACTLGRE    420
IQVARRGPCD PCGQCRFGSL CEVETGRCVC PSECVESAQP VCGSDGHTYA SECELHVHAC    480
THQISLYVAS AGHCQTCGEK VCTFGAVCSA GQCVCPRCEH PPPGPVCGSD GVTYLSACEL    540
REAACQQQVQ IEEAHAGPCE PAECGSGGSG SGEDDECEQE LCRQRGGIWD EDSEDGPCVC    600
DFSCQSVPRS PVCGSDGVTY GTECDLKKAR CESQQELYVA AQGACRGPTL APLLPVAFPH    660
CAQTPYGCCQ DNFTAAQGVG LAGCPSTCHC NPHGSYSGTC DPATGQCSCR PGVGGLRCDR    720
CEPGFWNFRG IVTDGHSGCT PCSCDPRGAV RDDCEQMTGL CSCRPGVAGP KCGQCPDGQV    780
LGHLGCEADP MTPVTCVEIH CEFGASCVEK AGFAQCICPT LTCPEANSTK VCGSDGVTYG    840
NECQLKAIAC RQRLDISTQS LGPCQESVTP GASPTSASMT TPRHILSKTL PPPHNSLPLS    900
PGSTTHDWPT PLPISPHTTV SIPRSTAWPV LTVPPTAAAS DVTSLATSIF SESGSANGSG    960
DEELSGDEEA SGGGSGGLEP PVGSIVVTHG PPIERASCYN SPLGCCSDGK TPSLDSEGSN    1020
CPATKAFQGV LELEGVEGQE LFYTPEMADP KSELFGETAR SIESTLDDLF RNSDVKKDFW    1080
SVRLRELGPG KLVRAIVDVH FDPTTAFQAS DVGQALLRQI QVSRPWALAV RRPLQEHVRF    1140
LDFDWFPTFF TGAATGTTAA MATARATTVS RLPASSVTPR VYPSHTSRPV GRTTAPPTTR    1200
RPPTTATNMD RPRTPGHQQP SKSCDSQPCL HGGTCQDQDS GKGFTCSCTA GRGGSVCEKV    1260
QPPSMPAFKG HSFLAFPTLR AYHTLRLALE FRALETEGLL LYNGNARGKD FLALALLDGR    1320
VQFRFDTGSG PAVLTSLVPV EPGRWHRLEL SRHWRQGTLS VDGETPVVGE SPSGTDGLNL    1380
DTNLYVGGIP EEQVAMVLDR TSVGVGLKGC IRMLDINNQQ LELSDWQRAA VQSSGVGECG    1440
DHPCLPNPCH GGALCQALEA GMFLCQCPPG RFGPTCADES SPCQPNPCHG AAPCRVLSSG    1500
GAKCECPLGR SGTFCQTVLE TAGSRPFLAD FNGFSYLELK GLHTFERDLG EKMALEMVFL    1560
ARGPSGLLLY NGQKTDGKGD FVSLALHNRH LEFCYDLGKG AAVIRSKEPI ALGTWVRVFL    1620
ERNGRKGALQ VGDGPRVLGE SPKSRKVPHT MLNLKEPLYI GGAPDFSKLA RGAAVSSGFS    1680
GVIQLVSLRG HQLLTQEHVL RAVDVSPFAD HPCTQALGNP CLNGGSCVPR EATYECLCPG    1740
GFSGLHCEKG LVEKSVGDLE TLAFDGRTYI EYLNAVIESE KALQSNHFEL SLRTEATQGL    1800
VLWIGKAAER ADYMALAIVD GHLQLSYDLG SQPVVLRSTV KVNTNRWLRI RAHREHREGS    1860
LQVGNEAPVT GSSPLGATQL DTDGALWLGG LQKLPVGQAL PKAYGTGFVG CLRDVVVGHR    1920
QLHLLEDAVT KPELRPCPTP                                                1940

SEQ ID NO: 7            moltype = AA  length = 452
FEATURE                 Location/Qualifiers
REGION                  1..452
                        note = Amino acid sequence encoding Minimal human Agrin
                         human sequence - G1 + G2
source                  1..452
                        mol_type = protein
                        organism = synthetic construct
SEQUENCE: 7
GAPVPAFEGR SFLAFPTLRA YHTLRLALEF RALEPQGLLL YNGNARGKDF LALALLDGRV    60
QLRFDTGSGP AVLTSAVPVE PGQWHRLELS RHWRRGTLSV DGETPVLGES PSGTDGLNLD    120
TDLFVGGVPE DQAAVALERT FVGAGLRGCI RLLDVNNQRL ELGIGPGAAT RGSGVGECGD    180
HPCLPNPCHG GAPCQNLEAG RFHCQCPPGR VGPTCADEKS PCQPNPCHGA APCRVLPEGG    240
AQCECPLGRE GTFCQTASGQ DGSGPFLADF NGFSHLELRG LHTFARDLGE KMALEVVFLA    300
RGPSGLLLYN GQKTDGKGDF VSLALRDRRL EFRYDLGKGA AVIRSREPVT LGAWTRVSLE    360
RNGRKGALRV GDGPRVLGES PKSRKVPHTV LNLKEPLYVG GAPDFSKLAR AAAVSSGFDG    420
AIQLVSLGGR QLLTPEHVLR QVDVTSFAGH PC                                  452

SEQ ID NO: 8            moltype = AA  length = 188
FEATURE                 Location/Qualifiers
REGION                  1..188
                        note = Amino acid sequence encoding Minimal human Agrin
                         human sequence - G2 only
source                  1..188
                        mol_type = protein
                        organism = synthetic construct
SEQUENCE: 8
PFLADFNGFS HLELRGLHTF ARDLGEKMAL EVVFLARGPS GLLLYNGQKT DGKGDFVSLA    60
LRDRRLEFRY DLGKGAAVIR SREPVTLGAW TRVSLERNGR KGALRVGDGP RVLGESPKSR    120
KVPHTVLNLK EPLYVGGAPD FSKLARAAAV SSGFDGAIQL VSLGGRQLLT PEHVLRQVDV    180
TSFAGHPC                                                             188
```

-continued

```
SEQ ID NO: 9               moltype = AA   length = 2034
FEATURE                    Location/Qualifiers
source                     1..2034
                           mol_type = protein
                           organism = Mus musculus
SEQUENCE: 9
MVRPRLSFPA PLLPLLLLLA AAAPAVPGAS GTCPERALER REEEANVVLT GTVEEILNVD     60
PVQHTYSCKV RVWRYLKGKD VVAQESLLDG GNKVVIGGFG DPLICDNQVS TGDTRIFFVN    120
PAPPYLWPAH KNELMLNSSL MRITLRNLEE VEFCVEDKPG IHFTAAPSMP PDVCRGMLCG    180
FGAVCEPSVE DPGRASCVCK KNVCPAMVAP VCGSDASTYS NECELQRAQC NQQRRIRLLR    240
QGPCGSRDPC ANVTCSFGST CVPSADGQTA SCLCPTTCFG APDGTVCGSD GVDYPSECQL    300
LRHACANQEH IFKKFDGPCD PCQGSMSDLN HICRVNPRTR HPEMLLRPEN CPAQHTPICG    360
DDGVTYENDC VMSRIGAARG LLLQKVRSGQ CQTRDQCPET CQFNSVCLSR RGRPHCSCDR    420
VTCDGAYRPV CAQDGHTYDN DCWRQQAECR QQQTIPPKHQ GPCDQTPSPC RGAQCAFGAT    480
CTVKNGKAVC ECQRVCSGGY DPVCGSDGVT YGSVCELESM ACTLGREIRV ARRGPCDRCG    540
QCRFGSLCEV ETGRCVCPSE CVESAQPVCG SDGHTYASEC ELHVHACTHQ ISLYVASAGH    600
CQTCGETVCT FGAVCSAGQC VCPRCEHPPP GPVCGSDGVT YLSACELREA ACQQQVQIEE    660
ARAGPCEPAE CGSGGSGSGE DNACEQELCR QHGGVWDEDS EDGPCVCDFS CQSVLKSPVC    720
GSDGVTYSTE CHLKKARCEA RQELYVAAQG ACRGPTLAPL LPMASPHCAQ TPYGCCQDNV    780
TAAQGVGLAG CPSTCHCNPH GSYSGTCDPV TGQCSCRPGV GGLRCDRCEP GFWNFRGIVT    840
DGHSGCTPCS CDPRGAVRDD CEQMTGLCSC RPGVAGPKCG QCPDGQALGH LGCEADPTTP    900
VTCVEMHCEF GASCVEEAGF AQCVCPTLTC PEANSTKVCG SDGVTYGNEC QLKTIACRQR    960
LDISIQSLGP CRESVAPGVS PTSASMTTPR HILSRTLASP HSSLPLSPST TAHDWPTPLP   1020
TSPQTVVGTP RSTAATPSDV ASLATAIFRE SGSTNGSGDE ELSGDEEASG GGSGGLEPPV   1080
GSVVVTHGPP IERASCYNSP LGCCSDGKTP SLDSEGSNCP ATKAFQGVLE LEGVEGQELF   1140
YTPEMADPKS ELFGETARSI ESTLDDLFRN SDVKKDFWSI RLRELGPGKL VRAIVDVHFD   1200
PTTAFQAPDV GQALLQQIQV SRPWALAVRR PLREHVRFLD FDWFPTFFTG AATGTTAAVA   1260
TARATTVSRL SASSVTPRVY PSYTSRPVGR TTAPLTTRRP PTTTASIDRP RTPGPQRPPK   1320
SCDSQPCLHG GTCQDLDSGK GFSCSCTAGR AGTVCEKVQL PSVPAFKGHS FLAFPTLRAY   1380
HTLRLALEFR ALETEGLLLY NGNARGKDFL ALALLDGHVQ FRFDTGSGPA VLTSLVPVEP   1440
GRWHRLELSR HWRQGTLSVD GEAPVVGESP SGTDGLNLDT KLYVGGLPEE QVATVLDRTS   1500
VGIGLKGCIR MLDINNQQLE LSDWQRAVVQ SSGVGECGDH PCSPNPCHGG ALCQALEAGV   1560
FLCQCPPGRF GPTCADEKNP CQPNPCHGSA PCHVLSRGGA KCACPLGRSG SFCETVLENA   1620
GSRPFLADFN GFSYLELKGL HTFERDLGEK MALEMVFLAR GPSGLLLYNG QKTDGKGDFV   1680
SLALHNRHLE FRYDLGKGAA IIRSKEPIAL GTWVRVFLER NGRKGALQVG DGPRVLGESP   1740
VPHTMLNLKE PLYVGGAPDF SKLARGAAVA SGFDGAIQLV SLRGHQLLTQ EHVLRAVDVA   1800
PFAGHPCTQA VDNPCLNGGS CIPREATYEC LCPGGFSGLH CEKGIVEKSV GDLETLAFDG   1860
RTYIEYLNAV TESEKALQSN HFELSLRTEA TQGLVLWIGK VGERADYMAL AIVDGHLQLS   1920
YDLGSQPVVL RSTVKVNTNR WLRVRAHREH REGSLQVGNE APVTGSSPLG ATQLDTDGAL   1980
WLGGLQKLPV GQALPKAYGT GFVGCLRDVV VGHRQLHLLE DAVTKPELRP CPTL          2034

SEQ ID NO: 10              moltype = DNA   length = 20
FEATURE                    Location/Qualifiers
misc_feature               1..20
                           note = Single strand DNA oligonucleotide
source                     1..20
                           mol_type = other DNA
                           organism = synthetic construct
SEQUENCE: 10
gtcggctcgc ggcaaaaagc                                                 20

SEQ ID NO: 11              moltype = DNA   length = 20
FEATURE                    Location/Qualifiers
misc_feature               1..20
                           note = Single strand DNA oligonucleotide
source                     1..20
                           mol_type = other DNA
                           organism = synthetic construct
SEQUENCE: 11
gacatcaaag agaagctgtg                                                 20

SEQ ID NO: 12              moltype = DNA   length = 21
FEATURE                    Location/Qualifiers
misc_feature               1..21
                           note = Single strand DNA oligonucleotide
source                     1..21
                           mol_type = other DNA
                           organism = synthetic construct
SEQUENCE: 12
actccatacc gataaaggaa g                                               21

SEQ ID NO: 13              moltype = DNA   length = 20
FEATURE                    Location/Qualifiers
misc_feature               1..20
                           note = Single strand DNA oligonucleotide
source                     1..20
                           mol_type = other DNA
                           organism = synthetic construct
SEQUENCE: 13
```

-continued

```
gagagaaaga aaccagagtg                                           20

SEQ ID NO: 14            moltype = DNA   length = 21
FEATURE                  Location/Qualifiers
misc_feature             1..21
                         note = Single strand DNA oligonucleotide
source                   1..21
                         mol_type = other DNA
                         organism = synthetic construct
SEQUENCE: 14
gtctagcagg ttcttgaaat c                                         21

SEQ ID NO: 15            moltype = DNA   length = 20
FEATURE                  Location/Qualifiers
misc_feature             1..20
                         note = Single strand DNA oligonucleotide
source                   1..20
                         mol_type = other DNA
                         organism = synthetic construct
SEQUENCE: 15
aattcaagat gcagaagctg                                           20

SEQ ID NO: 16            moltype = DNA   length = 20
FEATURE                  Location/Qualifiers
misc_feature             1..20
                         note = Single strand DNA oligonucleotide
source                   1..20
                         mol_type = other DNA
                         organism = synthetic construct
SEQUENCE: 16
gaattttgag gtctctgctg                                           20

SEQ ID NO: 17            moltype = DNA   length = 21
FEATURE                  Location/Qualifiers
misc_feature             1..21
                         note = Single strand DNA oligonucleotide
source                   1..21
                         mol_type = other DNA
                         organism = synthetic construct
SEQUENCE: 17
ccagaaacat catcataacc g                                         21

SEQ ID NO: 18            moltype = DNA   length = 20
FEATURE                  Location/Qualifiers
misc_feature             1..20
                         note = Single strand DNA oligonucleotide
source                   1..20
                         mol_type = other DNA
                         organism = synthetic construct
SEQUENCE: 18
catcgccacc ttaatagttg                                           20

SEQ ID NO: 19            moltype = DNA   length = 20
FEATURE                  Location/Qualifiers
misc_feature             1..20
                         note = Single strand DNA oligonucleotide
source                   1..20
                         mol_type = other DNA
                         organism = synthetic construct
SEQUENCE: 19
gtcaggctgg tcaccttctg                                           20

SEQ ID NO: 20            moltype = DNA   length = 20
FEATURE                  Location/Qualifiers
misc_feature             1..20
                         note = Single strand DNA oligonucleotide
source                   1..20
                         mol_type = other DNA
                         organism = synthetic construct
SEQUENCE: 20
aactcttggc accatgaacc                                           20

SEQ ID NO: 21            moltype = DNA   length = 22
FEATURE                  Location/Qualifiers
misc_feature             1..22
                         note = Single strand DNA oligonucleotide
source                   1..22
                         mol_type = other DNA
                         organism = synthetic construct
```

-continued

```
SEQUENCE: 21
gctgggctcc ctggacattg ac                                              22

SEQ ID NO: 22          moltype = DNA   length = 22
FEATURE                Location/Qualifiers
misc_feature           1..22
                       note = Single strand DNA oligonucleotide
source                 1..22
                       mol_type = other DNA
                       organism = synthetic construct
SEQUENCE: 22
cctgggcctg gattctggtg at                                              22

SEQ ID NO: 23          moltype = DNA   length = 25
FEATURE                Location/Qualifiers
misc_feature           1..25
                       note = Single strand DNA oligonucleotide
source                 1..25
                       mol_type = other DNA
                       organism = synthetic construct
SEQUENCE: 23
ccagtgtgaa cttgattttg atgaa                                           25

SEQ ID NO: 24          moltype = DNA   length = 27
FEATURE                Location/Qualifiers
misc_feature           1..27
                       note = Single strand DNA oligonucleotide
source                 1..27
                       mol_type = other DNA
                       organism = synthetic construct
SEQUENCE: 24
aacataactt gggagacaga gacatct                                         27

SEQ ID NO: 25          moltype = DNA   length = 20
FEATURE                Location/Qualifiers
misc_feature           1..20
                       note = Single strand DNA oligonucleotide
source                 1..20
                       mol_type = other DNA
                       organism = synthetic construct
SEQUENCE: 25
catcgacgcc cagatgaaga                                                 20

SEQ ID NO: 26          moltype = DNA   length = 20
FEATURE                Location/Qualifiers
misc_feature           1..20
                       note = Single strand DNA oligonucleotide
source                 1..20
                       mol_type = other DNA
                       organism = synthetic construct
SEQUENCE: 26
tggtgaacag ggtcccaaac                                                 20

SEQ ID NO: 27          moltype = DNA   length = 18
FEATURE                Location/Qualifiers
misc_feature           1..18
                       note = Single strand DNA oligonucleotide
source                 1..18
                       mol_type = other DNA
                       organism = synthetic construct
SEQUENCE: 27
cggaggagcg aacacctg                                                   18

SEQ ID NO: 28          moltype = DNA   length = 20
FEATURE                Location/Qualifiers
misc_feature           1..20
                       note = Single strand DNA oligonucleotide
source                 1..20
                       mol_type = other DNA
                       organism = synthetic construct
SEQUENCE: 28
gttggatcct caccctctgc                                                 20

SEQ ID NO: 29          moltype = DNA   length = 20
FEATURE                Location/Qualifiers
misc_feature           1..20
                       note = Single strand DNA oligonucleotide
source                 1..20
                       mol_type = other DNA
```

```
                                  organism = synthetic construct
SEQUENCE: 29
ttcgatggtc cttgtgaccc                                                               20

SEQ ID NO: 30          moltype = DNA   length = 20
FEATURE                Location/Qualifiers
misc_feature           1..20
                       note = Single strand DNA oligonucleotide
source                 1..20
                       mol_type = other DNA
                       organism = synthetic construct
SEQUENCE: 30
agataggtgt gtgttgggcg                                                               20

SEQ ID NO: 31          moltype = DNA   length = 20
FEATURE                Location/Qualifiers
misc_feature           1..20
                       note = Single strand DNA oligonucleotide
source                 1..20
                       mol_type = other DNA
                       organism = synthetic construct
SEQUENCE: 31
gtgcccatcg tcaacctgaa                                                               20

SEQ ID NO: 32          moltype = DNA   length = 20
FEATURE                Location/Qualifiers
misc_feature           1..20
                       note = Single strand DNA oligonucleotide
source                 1..20
                       mol_type = other DNA
                       organism = synthetic construct
SEQUENCE: 32
agttgaccct gggagccaga                                                               20

SEQ ID NO: 33          moltype = DNA   length = 22
FEATURE                Location/Qualifiers
misc_feature           1..22
                       note = Single strand DNA oligonucleotide
source                 1..22
                       mol_type = other DNA
                       organism = synthetic construct
SEQUENCE: 33
ccttctggca caagtctctt gg                                                            22

SEQ ID NO: 34          moltype = DNA   length = 22
FEATURE                Location/Qualifiers
misc_feature           1..22
                       note = Single strand DNA oligonucleotide
source                 1..22
                       mol_type = other DNA
                       organism = synthetic construct
SEQUENCE: 34
tcgaagatga cactggcatc gg                                                            22

SEQ ID NO: 35          moltype = DNA   length = 20
FEATURE                Location/Qualifiers
misc_feature           1..20
                       note = Single strand DNA oligonucleotide
source                 1..20
                       mol_type = other DNA
                       organism = synthetic construct
SEQUENCE: 35
tcgagcttga tctctcctat                                                               20

SEQ ID NO: 36          moltype = DNA   length = 20
FEATURE                Location/Qualifiers
misc_feature           1..20
                       note = Single strand DNA oligonucleotide
source                 1..20
                       mol_type = other DNA
                       organism = synthetic construct
SEQUENCE: 36
tggtcccagg tcttacagaa                                                               20

SEQ ID NO: 37          moltype = DNA   length = 20
FEATURE                Location/Qualifiers
misc_feature           1..20
                       note = Single strand DNA oligonucleotide
source                 1..20
```

-continued

```
                          mol_type = other DNA
                          organism = synthetic construct
SEQUENCE: 37
tggccggcag cgtttctgag                                              20

SEQ ID NO: 38          moltype = AA  length = 4380
FEATURE                Location/Qualifiers
source                 1..4380
                       mol_type = protein
                       organism = Homo sapiens
SEQUENCE: 38
MGWRAAGALL LALLLHGRLL AVTHGLRAYD GLSLPEDIET VTASQMRWTH SYLSDDEDML    60
ADSISGDDLG SGDLGSGDFQ MVYFRALVNF TRSIEYSPQL EDAGSREFRE VSEAVVDTLE   120
SEYLKIPGDQ VVSVVFIKEL DGWVFVELDV GSEGNADGAQ IQEMLLRVIS SGSVASYVTS   180
PQGFQFRRLG TVPQFPPRACT EAEFACHSYN ECVALEYRCD RRPDCRDMSD ELNCEEPVLG   240
ISPTFSLLVE TTSLPPRPET TIMRQPPVTH APQPLLPGSV RPLPCGPQEA ACRNGHCIPR   300
DYLCDGQEDC EDGSDELDCG PPPPCEPNEF PCGNGHCALK LWRCDGDFDC EDRTDEANCP   360
TKRPEEVCGP TQFRCVSTNM CIPASFHCDE ESDCPDRSDE FGCMPPQVVT PPRESIQASR   420
GQTVTFTCVA IGVPTPIINW RLNWGHIPSH PRVTVTSEGG RGTLIIRDVK ESDQGAYTCE   480
AMNARGMVFG IPDGVLELVP QRGPCPDGHF YLEHSAACLP CFCFGITSVC QSTRRFRDQI   540
RLRFDQPDDF KGVNVTMPAQ PGTPPLSSTQ LQIDPSLHEF QLVDLSRRFL VHDSFWALPE   600
QFLGNKVDSY GGSLRYNVRY ELARGMLEPV QRPDVVLMGA GYRLLSRGHT PTQPGALNQR   660
QVQFSEEHWV HESGRPVQRA ELLQVLQSLE AVLIQTVYNT KMASVGLSDI AMDTTVTHAT   720
SHGRAHSVEE CRCPIGYSGL SCESCDAHFT RVPGGPYLGT CSGCNCNGHA SSCDPVYGHC   780
LNCQHNTEGP QCNKCKAGFF GDAMKATATS CRPCPCPYID ASRRFSDTCF LDTDGQATCD   840
ACAPGYTGRR CESCAPGYEG NPIQPGGKCR PVNQEIVRCD ERGSMGTSGE ACRCKNNVVG   900
RLCNECADGS FHLSTRNPDG CLKCFCMGVS RHCTSSSWSR AQLHGASEEP GHFSLTNAAS   960
THTTNEGIFS PTPGELGFSS FHRLLSGPYF WSLPSRFLGD KVTSYGGELR FTVTQRSQPG  1020
STPLHGQPLV VLQGNNIILE HHVAQEPSPG QPSTFIVPFR EQAWQRPDGQ PATREHLLMA  1080
LAGIDTLLIR ASYAQQPAES RVSGISMDVA VPEETGQDPA LEVEQCSCPP GYRGPSCQDC  1140
DTGYTRTPSG LYLGTCERCS CHGHSEACEP ETGACQGCQH HTEGPRCEQC QPGYYGDAQR  1200
GTPQDCQLCP CYGDPAAGQA AHTCFLDTDG HPTCDACSPG HSGRHCERCA PGYYGNPSQG  1260
QPCQRDSQVP GPIGCNCDPQ GSVSSQCDAA GQCQCKAQVE GLTCSHCRPH HFHLSASNPD  1320
GCLPCFCMGI TQQCASSAYT RHLISTHFAP GDFQGFALVN PQRNSRLTGE FTVEPVPEGA  1380
QLSFGNFAQL GHESFYWQLP ETYQGDKVAA YGGKLRYTLS YTAGPQGSPL SDPDVQITGN  1440
NIMLVASQPA LQGPERRSYE IMFREEFWRR PDGQPATREH LLMALADLDE LLIRATFSSV  1500
PLAASISAVS LEVAQPGPSN RPRALEVEEC RCPPGYIGLS CQDCAPGYTR TGSGLYLGHC  1560
ELCECNGHSD LCHPETGACS QCQHNAAGEF CELCAPGYYG DATAGTPEDC QPCACPLTNP  1620
ENMFSRTCES LGAGGYRCTA CEPGYTGQYC EQCGPGYVGN PSVQGGQCLP ETNQAPLVVE  1680
VHPARSIVPQ GGSHSLRCQV SGSPPHYFYW SREDGRPVPS GTQQRHQGSE LHFPSVQPSD  1740
AGVYICTCRN LHQSNTSRAE LLVTEAPSKP ITVTVEEQRS QSVRPGADVT FICTAKSKSP  1800
AYTLVWTRLH NGKLPTRAMD FNGILTIRNV QLSDAGTYVC TGSNMFAMDQ GTATLHVQAS  1860
GTLSAPVVSI HPPQLTVQPG QLAEFRCSAT GSPTPTLEWT GGPGGQLPAK AQIHGGILRL  1920
PAVEPTDQAQ YLCRAHSSAG QQVARAVLHV HGGGGPRVQV SPERTQVHAG RTVRLYCRAA  1980
GVPSATITWR KEGGSLPPQA RSERTDIATL LIPAITTADA GFYLCVATSP AGTAQARIQV  2040
VVLSASDASP PPVKIESSSP SVTEGQTLDL NCVVAGSAHA QVTWYRRGGS LPPHTQVHGS  2100
RLRLPQVSPA DSGEYVCRVE NGSGPKEASI TVSVLHGTHS GPSYTPVPGS TRPIRIEPSS  2160
SHVAEGQTLD LNCVVPGQAH AQVTWHKRGG SLPARHQTHG SLLRLHQVTP ADSGEYVCHV  2220
VGTSGPLEAS VLVTIEASVI PGPIPPVRIE SSSSTVAEGQ TLDLSCVVAG QAHAQVTWYK  2280
RGGSLPARHQ VRGSRLYIFQ ASPADAGQYV CRASNGMEAS ITVTVTGTQG ANLAYPAGST  2340
QPIRIEPSSS QVAEGQTLDL NCVVPGQSHA QVTWHKRGGS QVTWHQTHGS LLRLYQASPA  2400
DSGEYVCRVL GSSVPLEASV LVTIEPAGSV PALGVTPTVR IESSSSQVAE GQTLDLNCLV  2460
AGQAHAQVTW HKRGGSLPAR HQVHGSRLRL LQVTPADSGE YVCRVVGSSG TQEASVLVTI  2520
QQRLSGSHSQ GVAYPVRIES SSASLANGHT LDLNCLVASQ APHTITWYKR GGSLPSRHQI  2580
VGSRLRIPQV TPADSGEYVC HVSNGAGSRE TSLIVTIQGS GSSHVPSVSP PIRIESSSPT  2640
VVEGQTLDLN CVVARQPQAI ITWYKRGGSL PSRHQTHGSH LRLHQMSVAD SGEYVCRANN  2700
NIDALEASIV ISVSPSAGSP SAPGSSMPIR IESSSSHVAE GETLDLNCVV PGQAHAQVTW  2760
HKRGGSLPSH HQTRGSRLRL HHVSPADSGE YVCRVMGSSG PLEASVLVTI EASGSSAVHV  2820
PAPGGAPPIR IEPSSSRVAE GQTLDLKCVV PGQAHAQVTW HKRGGNLPAR HQVHGPLLRL  2880
NQVSPADSGE YSCQVTGSSG TLEASVLVTI EPSSPGPIPA PGLAQPIYIE ASSSHVTEGQ  2940
TLDLNCVVPG QAHAQVTWYK RGGSLPARHQ THGSQLRLHL VSPADSGEYV CRAASGPGPE  3000
QEASFTVTVP PSEGSSYRLR SPVISIDPPS STVQQGQDAS FKCLIHDGAA PISLEWKTRN  3060
QELEDNVHIS PNGSIITIVG TRPSNHGTYR CVASNAYGVA QSVVNLSVHG PPTVSVLPEG  3120
PVWVKVGKAV TLECVSAGEP RSSARWTRIS STPAKLEQRT YGLMDSHAVL QISSAKPSDA  3180
GTYVCLAQNA LGTAQKQVEV IVDTGAMAPG APQVQAEEAE LTVEAGHTAT LRCSATGSPA  3240
PTIHWSKLRS PLPWQHRLEG DTLIIPRVAQ QDSGQYICNA TSPAGHAEAT IILHVESPPY  3300
ATTVPEHASV QAGETVQLQC LAHGTPPLTF QWSRVGSSLP GRATARNELL HFERAAPEDS  3360
GRYRCRVTNK VGSAEAFAQL LVQGPPGSLP ATSIPAGSTP YQVTPQLET KSIGASVEFH  3420
CAVPSDRGTQ LRWFKEGGQL PPGHSVQDGV LRIQNLDQSC QGTYICQAHG PWGKAQASAQ  3480
LVIQALPSVL INIRTSVQTV VVGHAVEFEC LALGDPKPQV TWSKVGGHLR PGIVQSGGVV  3540
RIAHVELADA GQYRCTATNA AGTTQSHVLL LVQALPQISM PQEVRVPAGS AAVFPCIASG  3600
YPTPDISWSK LDGSLPPDSR LENNMLMLPS VRPQDAGTYV CTATNRQGKV KAFAHLQVPE  3660
RVVPYFTQTP YSFLPLPTIK DAYRKFEIKI TFRPDSADGM LLYNGQKRVP GSPTNLANRQ  3720
PDFISFGLVG GRPEFRFDAG SGMATIRHPT PLALGHFHTV TLLRSLTQGS LIVGDLAPVN  3780
GTSQGKFQGL DLNEELYLGG YPDYGAIPKA GLSSGFIGCV RELRIQGEEI VFHDLNLTAH  3840
GISHCPTCRD RPCQNGGQCH DSESSSYVCV CPAGFTGSRC EHSQALHCHP EACGPDATCV  3900
NRPDGRGYTC RCHLGRSGLR CEEGVTVTTP SLSGAGSYLA LPALTNTHHE LRLDVEFKPL  3960
APDGVLLFSG KKSGPVEDFV SLAMVGGHLE FRYELGSGLA VLRSAEPLAL GRWHRVSAER  4020
LNKDGSLRVN GGRPVLRSSP GKSQGLNLHT LLYLGGVEPS VPLSPATNMS AHFRGCVGEV  4080
```

-continued

```
SVNGKRLDLT YSFLGSQGIG QCYDSSPCER QPCQHGATCM PAGEYEFQCL CRDGFKGDLC  4140
EHEENPCQLR EPCLHGGTCQ GTRCLCLPGF SGPRCQQGSG HGIAESDWHL EGSGGNDAPG  4200
QYGAYFHDDG FLAFPGHVFS RSLPEVPETI ELEVRTSTAS GLLLWQGVEV GEAGQGKDFI  4260
SLGLQDGHLV FRYQLGSGEA RLVSEDPIND GEWHRVTALR EGRRGSIQVD GEELVSGRSP  4320
GPNVAVNAKG SVYIGGAPDV ATLTGGRFSS GITGCVKNLV LHSARPGAPP PQPLDLQHRA  4380
```